(12) United States Patent
Isab et al.

(10) Patent No.: US 12,103,939 B2
(45) Date of Patent: *Oct. 1, 2024

(54) SOLID PHARMACEUTICAL GOLD-BASED COMPOSITION

(71) Applicant: KING FAHD UNIVERSITY OF PETROLEUM AND MINERALS, Dhahran (SA)

(72) Inventors: Anvarhusein A. Isab, Dhahran (SA); Adam Ahmed Abdullah Sulaiman, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/606,260

(22) Filed: Mar. 15, 2024

(65) Prior Publication Data

US 2024/0279242 A1 Aug. 22, 2024

Related U.S. Application Data

(63) Continuation of application No. 17/825,009, filed on May 26, 2022, now Pat. No. 11,958,867, which is a continuation of application No. 16/554,224, filed on Aug. 28, 2019, now Pat. No. 11,384,100.

(51) Int. Cl.
*A61P 35/00* (2006.01)
*C07F 1/00* (2006.01)

(52) U.S. Cl.
CPC ............ *C07F 1/005* (2013.01); *A61P 35/00* (2018.01)

(58) Field of Classification Search
CPC ..................................................... A61P 35/00
See application file for complete search history.

(56) References Cited

U.S. PATENT DOCUMENTS 11,384,100 B2 7/2022 Isab et al.
2022/0281897 A1 9/2022 Isab et al.

OTHER PUBLICATIONS

Konnick, et al. ; A Mechanistic Change Results in 100 Times Faster CH Functionalization for Ethane versus Methane by a Homogeneous Pt Catalyst ; Journal of The American Chemical Society ; pp. 10085-10094 ; Jun. 13, 2014 ; 10 Pages.
Koutsouri, et al. ; Combining photosensitizers: The case of [Cl Pt(bpym)Re (CO) Cl] and its dithiolate analogs ; Polyhedron vol. 52 ; pp. 234-245 ; Mar. 22, 2013 ; Abstract Only ; 3 Pages.
Ha ; (2,2'-Bipyrimidine-κ N ,N )bis(thiocyanato-κN)platinum(II) ; Acta Crystallographia Scetion E, Structure Reports Online ; May 1, 2012 ; 12 pages.
Ha ; Dipotassium tetrakis(thiocyanato-jS)-palladate(II)-(2,20-bipyrimidinej 2N1,N10)bis(thiocyanato-jS)-palladium(II) (1/2) ; Acta Crystallographica Section E, Structure Reports Online ; Apr. 8, 2012 ; 14 Pages.
De Munno, et al. ; Low-temperature structures of catena-(bipyrimidine-N,N')bis(thiocyanato)copper(II) and poly-(??-bipyrimidine-N,N',N'',N''')tetrakis(thiocyanato)dicopper(II) ; Acta Crystallographica Section C Crystal Structure Communications ; Mar. 1993 ; 5 Pages.
Julve , et al. ; Synthesis, crystal structure, and magnetic properties of (.mu.-bipyrimidine)(cyanato)copper(II) and—(thiocyanato) copper(II) complexes ; Inorganic Chemistry ; 1993 ; pp. 795-802 ; 7 Pages.

(Continued)

*Primary Examiner* — Paul V Ward
(74) *Attorney, Agent, or Firm* — Oblon, McClelland, Maier & Neustadt, L.L.P.

(57) ABSTRACT

A gold(III) complex of formula (I) or formula (II)

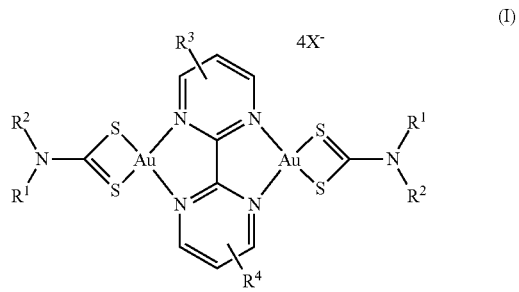

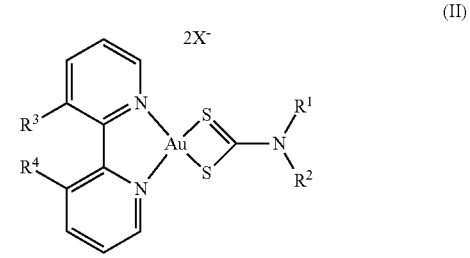

wherein $R^1$ and $R^2$ are each independently a hydrogen, an optionally substituted alkyl, an optionally substituted cycloalkyl, an optionally substituted arylalkyl, or an optionally substituted aryl; $R^3$ and $R^4$ are each independently a hydrogen, an optionally substituted alkyl, an optionally substituted cycloalkyl, an optionally substituted arylalkyl, an optionally substituted aryl, an optionally substituted heterocyclyl, an optionally substituted alkoxy, a hydroxyl, a halo, a nitro, a cyano, a N-monosubstituted amino group, or a N,N-disubstituted amino group; and X is Cl, Br, or I. A pharmaceutical composition containing the gold(III) complex of formula (I) or (II), and a method of treating cancer are included.

5 Claims, 36 Drawing Sheets

(56) References Cited

OTHER PUBLICATIONS

Ankianiec, et al. ; Synthesis and spectroscopic characteristics of bis-[dimethyl(phenyl)silylmethyl]platinum(II) complexes with nitrogen donor ligands ; Polyhedron vol. 8, Issue 1 ; pp. 57-69 ; 1989 ; Abstract Only ; 2 Pages.

Matsubayashi, et al. ; X-Ray crystal structure of (2'2-bipyrimidine)[1,2-dicyanoethylene-1,2-dithiolato(2-)] platinum(II)-N,N-dimethyloformamide and properties of PtS2N2-type complexes ; Journal of the Chemical Society, Dalton Transactions, Issue 8 ; 1988; Abstract Only ; 5 Pages.

Scott , et al. ; Comparison of the reactivities toward oxidative addition of the dimethylplatinum(II) units in mononuclear and binuclear complexes with bis(diimine) ligands ; Organometallics ; pp. 2522-2529 ; 1986 ; 7 Pages.

Bochmann, et al. ; Preparation and properties of 1-adamantylmethyl and adamantly complexes of transition metals ; Journal of the Chemical Society, Dalton Transaction, Issu 10 ; 1980 ; Abstract Only ; 4 Pages.

Pinedo et al. (2000).

McMahon et al. (2000).

C3 [Au(BPYH)(DEDTC)]Cl₂

C4 [Au(BPYH)(DBDTC)]Cl₂

C5 [Au₂(BPM)(Cl)₄]Cl₂

C6 [Au₂(BPM)(DMDTC)₂]Cl₄

SOLID PHARMACEUTICAL GOLD-BASED COMPOSITION

CROSS-REFERENCE TO RELATED APPLICATIONS

The present application is a Continuation of U.S. application Ser. No. 17/825,009, now allowed, having a filing date of May 26, 2022, which is a continuation of U.S. application Ser. No. 16/554,224, now U.S. Pat. No. 11,384,100, having a filing date of Aug. 28, 2019.

STATEMENT OF ACKNOWLEDGEMENT

This research was supported in part by grant IN171005 from the King Fahd University of Petroleum and Minerals.

STATEMENT REGARDING PRIOR DISCLOSURE BY THE INVENTORS

Aspects of this technology are described in an article "Potent In Vitro and In Vivo Anticancer Activity of New Bipyridine and Bipyrimidine Gold (III) Dithiocarbamate Derivatives" published in Cancers, 2019, 11, 474, on Apr. 4, 2019, which is incorporated herein by reference in its entirety.

BACKGROUND OF THE INVENTION

Technical Field

The present disclosure relates to bipyridine and bipyrimidine gold(III) dithiocarbamate-containing complexes with anticancer or antitumor properties, and pharmaceutical compositions and uses thereof.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cisplatin and a few related platinum compounds, such as carboplatin and oxaliplatin, are common anticancer agents, but their use often causes significant toxicity and leads to drug resistance. See Spreckelmeyer S.; Orvig C.; Casini A. Cellular transport mechanisms of cytotoxic metallodrugs: an overview beyond cisplatin. Molecules 2014. 19(10), 15584-15610; Cappetta D.; Rossi F.; Piegari E.; Quaini F.; Berrino L.; Urbanek K.; De A. A. Doxorubicin targets multiple players: A new view of an old problem. Pharmacol Res 2018. 127, 4-14; Galluzzi L.; Vitale I.; Michels J.; Brenner C.; Szabadkai G.; Harel-Bellan A.; Castedo M.; Kroemer G. Systems biology of cisplatin resistance: past, present and future. Cell Death Dis 2014. 5,e1257; and Dilruba S.; Kalayda G. V. Platinum-based drugs: past, present and future. Cancer Chemother Pharmacol 2016. 77, 1103-1124, each incorporated herein by reference in their entirety. Therefore, other metallodrugs containing platinum or non-platinum metals, such as ruthenium, palladium, titanium, gold and copper, have been investigated. See Nardon C.; Fregona D. Editorial: Throwing Light on Recent Advances on Metallodrugs: From Deemed Poisons to a Striking Hope for the Future. Curr Med Chem 2018. 25(4), 434-436; Lazarevic T.; Rilak A.; Bugarcic Z. D. Platinum, palladium, gold and ruthenium complexes as anticancer agents: Current clinical uses, cytotoxicity studies and future perspectives. Eur J Med Chem 2017. 142, 8-31; Soldevila-Barreda J. J.; Sadler P. J. Approaches to the design of catalytic metallodrugs. Curr Opin Chem Biol 2015. 25, 172-183; and Casini A.; Sun R. W.; Ott I. Medicinal Chemistry of Gold Anticancer Metallodrugs. Met Ions Life Sci 2018. 18. pii, books/9783110470734-013, each incorporated herein by reference in their entirety. In particular, gold(I) and gold(III) complexes have been found to have anticancer effects in vitro and in vivo. See, Nardon C.; Fregona D. Editorial: Throwing Light on Recent Advances on Metallodrugs: From Deemed Poisons to a Striking Hope for the Future. Curr Med Chem 2018. 25(4), 434-436; Casini A. Cellular transport mechanisms of cytotoxic metallodrugs: an overview beyond cisplatin. Molecules 2014. 19(10), 15584-15610; and Bertrand B.; Williams M. R. M.; Bochmann M. Gold(III) Complexes for Antitumor Applications: An Overview. Chemistry 2018. 24(46), 11840-11851, each incorporated herein by reference in their entirety.

Gold(I) and gold(III) complexes have a variety of mechanisms of action, including inhibition of the enzyme thioredoxin reductase (TrxR), increased generation of reactive oxygen species (ROS), proteasome inhibition, interaction with DNA, alteration of the cell cycle phases and modulation of kinases. See Bertrand B.; Williams M. R. M.; Bochmann M. Gold(III) Complexes for Antitumor Applications: An Overview. Chemistry 2018. 24(46), 11840-11851; Celegato M.; Borghese C.; Casagrande N.; Mongiat M.; Kahle X. U.; Paulitti A.; Spina M.; Colombatti A.; Aldinucci D. Preclinical activity of the repurposed drug Auranofin in classical Hodgkin lymphoma. Blood 2015. 126, 1394-1397; Aldinucci D.; Lorenzon D.; Stefani L.; Giovagnini L.; Colombatti A.; Fregona D. Antiproliferative and apoptotic effects of two new gold(III) methylsarcosinedithiocarbamate derivatives on human acute myeloid leukemia cells in vitro. Anticancer Drugs 2007. 18, 323-332; Milacic V.; Chen D.; Ronconi L.; Landis-Piwowar K. R.; Fregona D.; Dou Q. P. A novel anticancer gold(III) dithiocarbamate compound inhibits the activity of a purified 20S proteasome and 26S proteasome in human breast cancer cell cultures and xenografts. Cancer Res 2006. 66, 10478-10486; Gratteri P.; Massai L.; Michelucci E.; Rigo R.; Messori L.; Cinellu M. A.; Musetti C.; Sissi C.; Bazzicalupi C. Interactions of selected gold(III) complexes with DNA G quadruplexes. Dalton Trans 2015. 44(8), 3633-3639; Coronnello M.; Marcon G.; Carotti S.; Caciagli B.; Mini E.; Mazzei T.; Orioli P.; Messori L. Cytotoxicity, DNA damage, and cell cycle perturbations induced by two representative gold(III) complexes in human leukemic cells with different cisplatin sensitivity. Oncol Res 2000. 12(9-10), 361-370; and Saggioro D.; Rigobello M. P.; Paloschi L.; Folda A.; Moggach S. A.; Parsons S.; Ronconi L.; Fregona D.; Bindoli A. Gold(III)-dithiocarbamato complexes induce cancer cell death triggered by thioredoxin redox system inhibition and activation of ERK pathway. Chem Biol 2007. 14, 1128-1139, each incorporated herein by reference in their entirety. These multifaceted modes of action enable gold complexes to exert potent cytotoxicity against cancer cells, including multidrug-resistant tumor cells. See Nardon C.; Fregona D. Editorial: Throwing Light on Recent Advances on Metallodrugs: From Deemed Poisons to a Striking Hope for the Future. Curr Med Chem 2018. 25(4), 434-436; and Bertrand B.; Williams M. R. M.; Bochmann M. Gold(III) Complexes for Antitumor Applications: An Overview. Chemistry 2018. 24(46), 11840-11851, each incorporated herein by reference in its entirety. However, gold and other heavy metals such as platinum also react with the sulfur-containing amino acids cysteine (a thiol) and methionine (a thioether), generating metal-protein adducts that can be nephrotoxic. See Bertrand B.; Williams M. R. M.; Bochmann M. Gold(III) Complexes for Antitumor Applications: An Overview. Chemistry 2018. 24(46), 11840-11851.

The use of dithiocarbamate as a chelating ligand can potentially prevent interactions between the metal center of anticancer drugs and thiol-containing biomolecules. Through its sulfur atoms, dithiocarbamate coordinates metal ions, thereby stabilizing metal drugs and reducing interactions with biomolecules. See Nardon C.; Fregona D. Editorial: Throwing Light on Recent Advances on Metallodrugs: From Deemed Poisons to a Striking Hope for the Future. Curr Med Chem 2018. 25(4), 434-436; and Marzano C.; Ronconi L.; Chiara F.; Giron M. C.; Faustinelli I.; Cristofori P.; Trevisan A.; Fregona D. Gold(III)-dithiocarbamato anticancer agents: activity, toxicology and histopathological studies in rodents. Int J Cancer 2011. 129(2), 487-496, each incorporated herein by reference in their entirety. Gold(III) dithiocarbamate complexes have been reported to have potent in vitro anticancer activity against acute myeloid leukemia cells and prostate cancer cells and low toxicity in tumor-bearing mice. See Aldinucci D.; Lorenzon D.; Stefani L.; Giovagnini L.; Colombatti A.; Fregona D. Antiproliferative and apoptotic effects of two new gold(III) methylsarcosinedithiocarbamate derivatives on human acute myeloid leukemia cells in vitro. Anticancer Drugs 2007. 18, 323-332; and Cattaruzza L.; Fregona D.; Mongiat M.; Ronconi L.; Fassina A.; Colombatti A.; Aldinucci D. Antitumor activity of gold(III)-dithiocarbamato derivatives on prostate cancer cells and xenografts. Int J Cancer 2011. 128, 206-215, each incorporated herein by reference in their entirety. Second generation gold(III) dithiocarbamate complexes which are derivatives of oligopeptides (peptidomimetics) have also been made to improve the delivery and cellular uptake of these compounds. See Kouodom M. N.; Ronconi L.; Celegato M.; Nardon C.; Marchio L.; Dou Q. P.; Aldinucci D.; Formaggio F.; Fregona D. Toward the selective delivery of chemotherapeutics into tumor cells by targeting peptide transporters: tailored gold-based anticancer peptidomimetics. J Med Chem 2012. 55(5), 2212-2226, incorporated herein by reference in its entirety. These peptidomimetics were designed to target the peptide transporters PEPT1 and PEPT2 that are upregulated in several tumor types, and showed promising anticancer activity in different tumor models, including breast and prostate cancer. See Kouodom M. N.; Ronconi L.; Celegato M.; Nardon C.; Marchio L.; Dou Q. P.; Aldinucci D.; Formaggio F.; Fregona D. Toward the selective delivery of chemotherapeutics into tumor cells by targeting peptide transporters: tailored gold-based anticancer peptidomimetics. J Med Chem 2012. 55(5), 2212-2226; Nardon C.; Schmitt S. M.; Yang H.; Zuo J.; Fregona D.; Dou Q. P. Gold(III)-dithiocarbamato peptidomimetics in the forefront of the targeted anticancer therapy: preclinical studies against human breast neoplasia. PLOS One 2014. 9(1), e84248; and Celegato M.; Fregona D.; Mongiat M.; Ronconi L.; Borghese C.; Canzonieri V.; Casagrande N.; Nardon C.; Colombatti A.; Aldinucci D. Preclinical activity of multiple-target gold(III)-dithiocarbamato peptidomimetics in prostate cancer cells and xenografts. Future Med Chem 2014. 6(11), 1249-1263, each incorporated herein by reference in their entirety.

In parallel research, other metallodrugs with anticancer activity, including gold(I) and gold(III) complexes have been designed and synthesized. See Altaf M.; Monim-ul-Mehboob M.; Seliman A. A.; Sohail M.; Wazeer M. I.; Isab A. A.; Li L.; Dhuna V.; Bhatia G.; Dhuna K. Synthesis, characterization and anticancer activity of gold(I) complexes that contain tri-tert-butylphosphine and dialkyl dithiocarbamate ligands. Eur J Med Chem 2015. 95, 464-472; Altaf M.; Monom-ul-Mehboob M.; Selimam A. A.; Isab A. A.; Dhuna V.; Bhatia G.; Dhuna K. Synthesis, X-ray Structures, Spectroscopic Analysis and Anticancer Activity of Novel Gold(I) Carbene Complexes. Journal of Organometallic Chemistry 2014. 765, 68-79; and Al-Jaroudi S. S.; Altaf M.; Al-Saadi A. A.; Kawde A. N.; Altuwaijri S.; Ahmad S.; Isab A. A. Synthesis, characterization and theoretical calculations of (1,2-diaminocyclohexane)(1,3-diaminopropane)gold(III) chloride complexes: in vitro cytotoxic evaluations against human cancer cell lines. Biometals 2015. 28(5), 827-844, each incorporated herein by reference in their entirety. Together, these two research groups produced new bipyridine gold(III) dithiocarbamate complexes with nitrogen and sulfur donor ligands which are cytotoxic in cisplatin-resistant ovarian carcinoma cells as well as in p53-defective cancer cells of different tumor types, and wherein certain complexes are less cytotoxic in non-cancer human mesenchymal stromal cells than in cancer cells. See Altaf M.; Monim-ul-Mehboob M.; Kawde A. N.; Corona G.; Larcher R.; Ogasawara M.; Casagrande N.; Celegato M.; Borghese C.; Siddik Z. H.; Aldinucci D.; Isab A. A. New bipyridine gold(III) dithiocarbamate-containing complexes exerted a potent anticancer activity against cisplatin-resistant cancer cells independent of p53 status. Oncotarget 2017. 8(1), 490-505, incorporated herein by reference in its entirety. However, new gold complexes are needed with improved potency, antitumor properties, and with lower toxicity.

In view of the forgoing, one objective of the present disclosure is to provide safe and potent therapeutic complexes with low- and sub-micromolar antiproliferative activity based on bipyridine or bipyrimidine gold(III) dithiocarbamate-containing complexes, a pharmaceutical composition containing the gold(III) complexes, and a method for treating cancer with the gold(III) complexes.

BRIEF SUMMARY OF THE INVENTION

Accordingly, it is one object of the present invention to provide bipyridine and bipyrimidine gold(III) dithiocarbamate-containing complexes, which are non-toxic, have excellent pharmacologic properties with low- and sub-micromolar antiproliferative activity, and which remain effective even in multiple drug resistant cancers.

It is another object of the present invention to provide pharmaceutical compositions containing the gold(III) complexes.

It is yet another object of the present invention to provide methods for treating cancer with the gold(III) complexes.

Thus, the present invention provides:

A gold(III) complex of formula (I), (I)

or a pharmaceutically acceptable salt, solvate, tautomer, or stereoisomer thereof, wherein:

$R^1$ and $R^2$ are each independently a hydrogen, an optionally substituted alkyl, an optionally substituted cycloalkyl, an optionally substituted arylalkyl, or an optionally substituted aryl;

$R^3$ and $R^4$ are each independently a hydrogen, an optionally substituted alkyl, an optionally substituted cycloalkyl, an optionally substituted arylalkyl, an optionally substituted aryl, an optionally substituted heterocyclyl, an optionally substituted alkoxy, a hydroxyl, a halo, a nitro, a cyano, a N-monosubstituted amino group, or a N,N-disubstituted amino group; and X is Cl, Br, or I.

In some embodiments, $R^1$ and $R^2$ are each independently a $C_1$ to $C_8$ alkyl or a $C_7$ to $C_{12}$ arylalkyl.

In some embodiments, $R^1$ and $R^2$ are each methyl, ethyl, or benzyl.

In some embodiments, $R^3$ and $R^4$ are each hydrogen.

In some embodiments, X is Cl.

In some embodiments, the gold(III) complex is selected from the group consisting of A pharmaceutical composition, which includes the gold (III) complex of formula (I) and a pharmaceutically acceptable carrier and/or excipient.

In some embodiments, the gold(III) complex of formula (I) is present in the pharmaceutical composition in a concentration of 1 to 50 μM, relative to a total volume of the pharmaceutical composition.

A method for treating cancer in a subject that includes administering to the subject a therapeutically effective amount of the gold(III) complex of formula (I), wherein the cancer is at least one selected from the group consisting of bone cancer, lung cancer, prostate cancer, breast cancer, ovarian cancer, and cervical cancer.

In some embodiments, the therapeutically effective amount of the gold(III) complex of formula (I) is from 0.01 to 25 mg/kg of the gold(III) complex of formula (I) per body weight of the subject.

A gold(III) complex of formula (II), (II)

or a pharmaceutically acceptable salt, solvate, tautomer, or stereoisomer thereof, wherein:

$R^1$ and $R^2$ are each independently a hydrogen, an optionally substituted alkyl, an optionally substituted cycloalkyl, an optionally substituted arylalkyl, or an optionally substituted aryl;

$R^3$ and $R^4$ are each independently an optionally substituted alkyl, an optionally substituted cycloalkyl, an optionally substituted arylalkyl, an optionally substituted aryl, an optionally substituted heterocyclyl, an optionally substituted alkoxy, a hydroxyl, a halo, a nitro, a cyano, a N-monosubstituted amino group, or a N,N-disubstituted amino group; and X is Cl, Br, or I.

In some embodiments, $R^1$ and $R^2$ are each independently a $C_1$ to $C_8$ alkyl or a $C_7$ to $C_{12}$ arylalkyl.

In some embodiments, $R^1$ and $R^2$ are each methyl, ethyl, or benzyl.

In some embodiments, $R^3$ and $R^4$ are each hydroxyl.

In some embodiments, X is Cl.

In some embodiments, the gold(III) complex of formula (II) is selected from the group consisting of

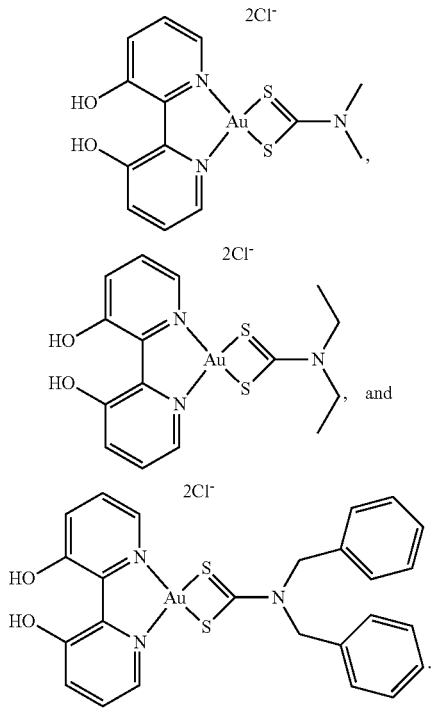

A pharmaceutical composition, that includes the gold(III) complex of formula (II) and a pharmaceutically acceptable carrier and/or excipient.

In some embodiments, the gold(III) complex of formula (II) is present in the pharmaceutical composition in a concentration of 1 to 50 μM, relative to a total volume of the pharmaceutical composition.

A method for treating cancer in a subject, that includes administering to the subject a therapeutically effective amount of the gold(III) complex of formula (II), wherein the cancer is at least one selected from the group consisting of bone cancer, lung cancer, prostate cancer, breast cancer, ovarian cancer, and cervical cancer.

In some embodiments, the therapeutically effective amount of the gold(III) complex of formula (II) is from 0.01 to 25 mg/kg of the gold(III) complex of formula (II) per body weight of the subject.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
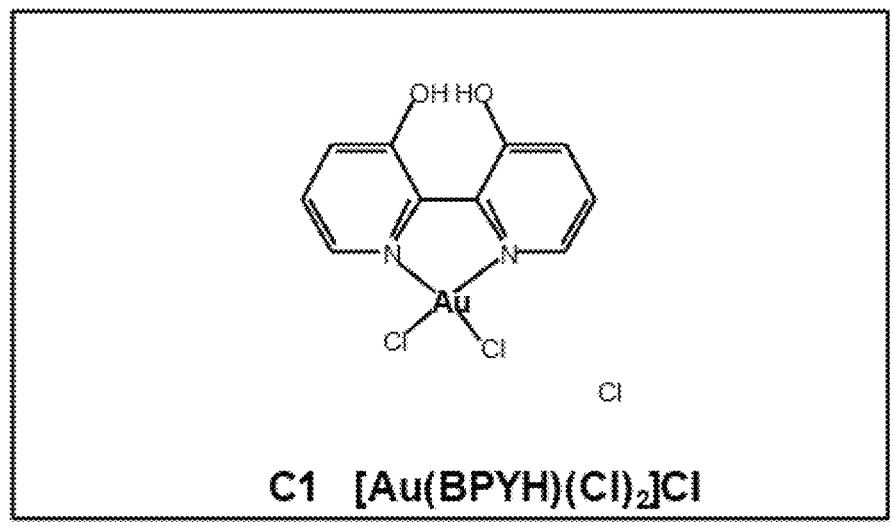
FIGS. 1A-1H illustrate chemical structures of gold(III) complexes $C_1$-$C_8$.
Figure 1B:
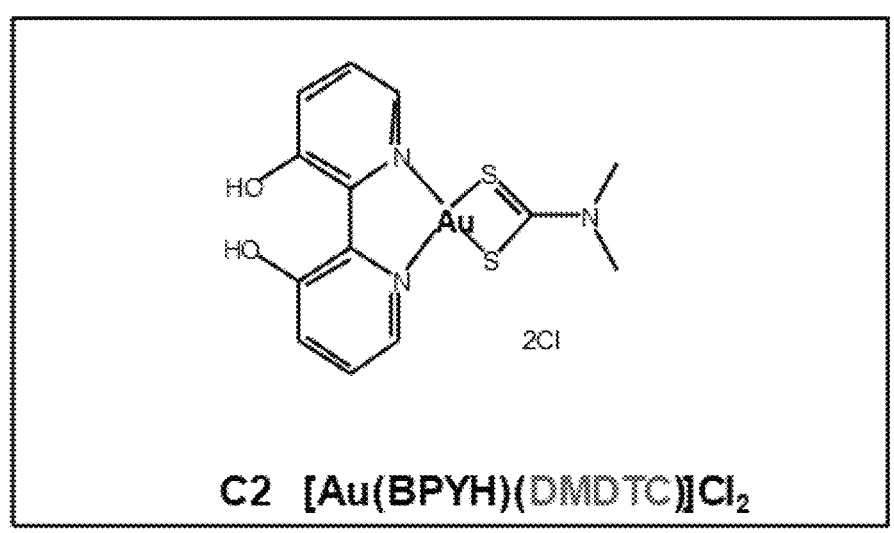
Figure 1C:
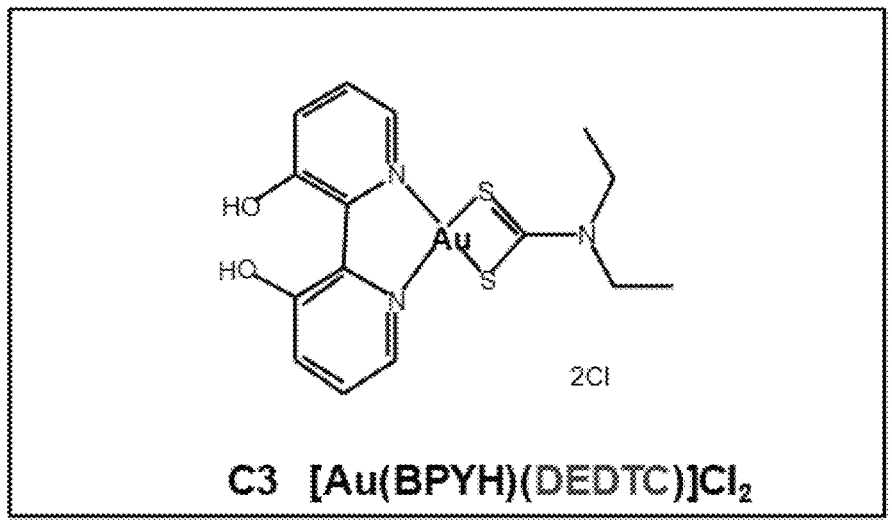
Figure 1D:
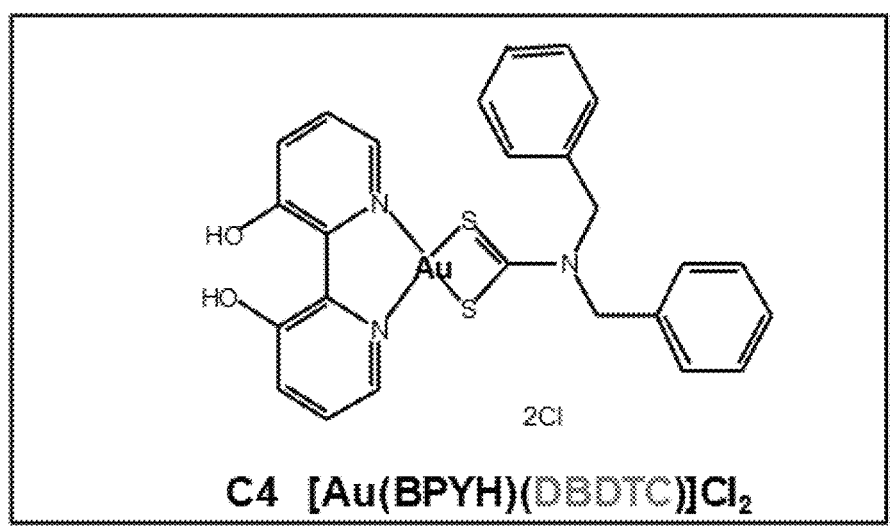
Figure 1E:
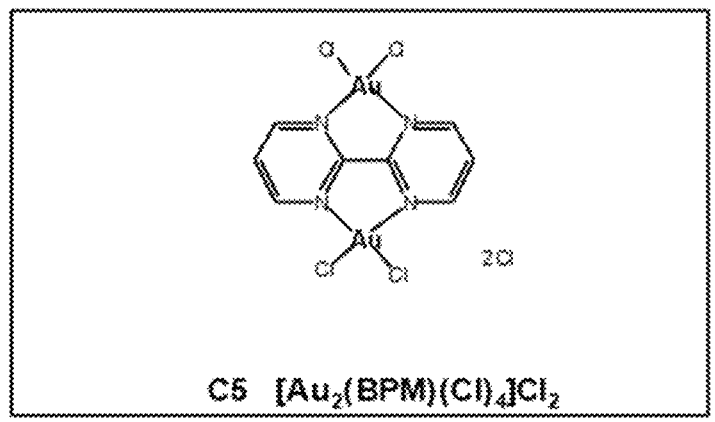
Figure 1F:
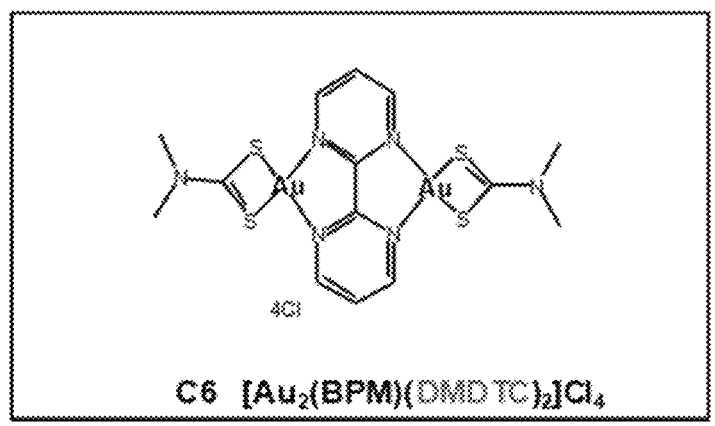
Figure 1G:
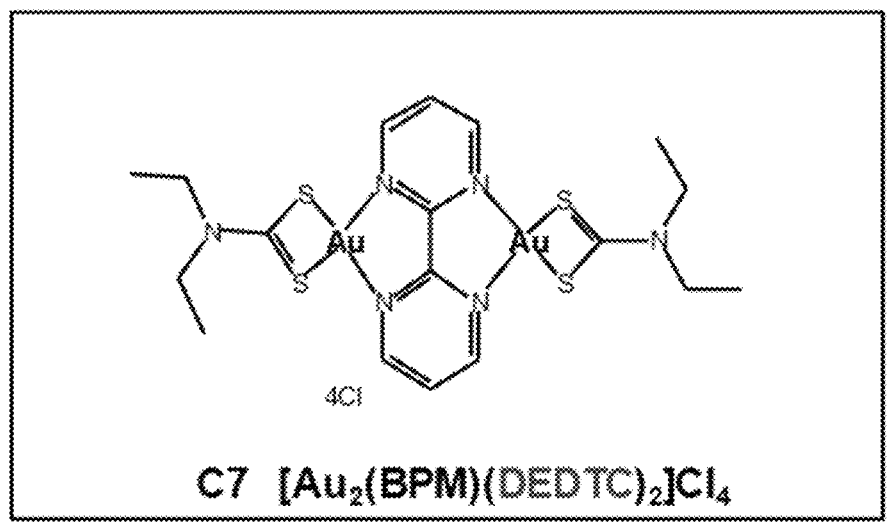
Figure 1H:
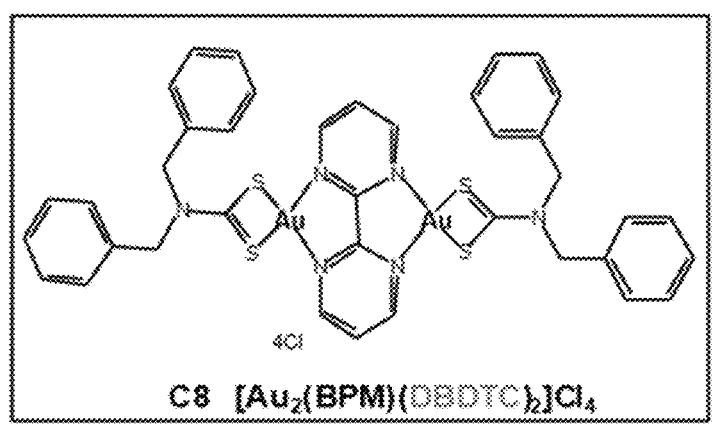

Embodiments of the present disclosure will now be described more fully hereinafter with reference to the accompanying drawings, in which some, but not all embodiments of the disclosure are shown.

Definitions

As used herein, the terms "compound", "complex", and "product" are used interchangeably, and are intended to refer to a chemical entity, whether in the solid, liquid or gaseous phase, and whether in a crude mixture or purified and isolated. In the present disclosure, the phrase "gold (III) complex" or "gold (III) complexes" may refer to the gold (III) complex of formula (I), the gold(III) complex of formula II, or both, unless otherwise specified.

As used herein, the term "mononuclear" refers to coordination complexes containing a single metal atom (ion) in a single coordination sphere. While the term "binuclear" refers to coordination compounds containing two metal atoms (ions) in a single coordination sphere. The two atoms may be held together through direct metal-metal bonds, through bridging ligands, or both.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present in the complexes, and all such stable isomers are contemplated in the present disclosure. Cis- and trans- (or E- and Z-) geometric isomers of the complexes of the present disclosure are described and may be isolated as a mixture of isomers or as separated isomeric forms. The present complexes can be isolated in optically active or racemic forms. Optically active forms may be prepared by resolution of racemic forms or by synthesis from optically active starting materials. All processes used to prepare complexes of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric complexes of the present disclosure may be separated into the individual isomers. Complexes of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g., polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

The present disclosure is intended to include all isotopes of atoms occurring in the present complexes. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salt" refers to derivatives of the disclosed complexes wherein the parent complex is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. The pharmaceutically acceptable salts of the present disclosure can be synthesized from the parent complex that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

As used herein, the term "alkyl" unless otherwise specified refers to both branched and straight chain aliphatic (non-aromatic) hydrocarbons which may be primary, secondary, and/or tertiary hydrocarbons typically having 1 to 32 carbon atoms (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, etc.) and specifically includes, but is not limited to, saturated alkyl groups such as methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-proylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), as well as unsaturated alkenyl and alkynyl variants such as vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, oleyl, linoleyl, and the like.

The term "cycloalkyl" refers to cyclized alkyl groups. Exemplary cycloalkyl groups include, but are not limited to, saturated cycloalkyl groups such as cyclopropyl, cyclobutyl, cyclopentyl, cyclohexyl, norbornyl, and adamantyl, branched cycloalkyl groups such as 1-methylcyclopropyl and 2-methylcyclopropyl, and cycloalkenyl groups such as cyclobutenyl, cyclopentenyl, and cyclohexenyl.

The term "aryl" means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, anthracenyl, indanyl, 1-naphthyl, 2-naphthyl, and tetrahydronaphthyl. The fused aryls may be connected to another group either at a suitable position on the cycloalkyl/cycloalkenyl ring or the aromatic ring.

The term "arylalkyl", as used herein, refers to a straight or branched chain alkyl moiety (as defined above) that is substituted by an aryl group (as defined above), examples of which include, but are not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkoxy" refers to an —O-alkyl group. Example alkoxy groups include, but are not limited to, methoxy, ethoxy, propoxy (e.g., n-propoxy and isopropoxy), and t-butoxy.

As used herein, the term "heterocycle" or "heterocyclyl" is intended to mean a stable 3-, 4-, 5-, 6-, or 7-membered monocyclic, 7-, 8-, 9-, 10-, or 11-membered bicyclic, or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any bicyclic or polycyclic group in which any of the above-defined heterocyclic rings is fused to a carbocyclic ring, the carbocyclic ring being either saturated, unsaturated, or aromatic (e.g., a benzene ring). The nitrogen and sulfur heteroatoms may optionally be oxidized (i.e., N→0 and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include "heteroaryl" (which will be defined below).

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furyl, furazanyl, imidazolidinyl, imidazolinyl, imidazolyl, 1H-indazolyl, imidazolopyridinyl, indolenyl, indolinyl, indolizinyl, indolyl (e.g., 1H-indolyl), isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, homopiperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles. Examples of 5- to 10-membered heterocycles include, but are not limited to, pyridinyl, thienyl, pyrrolyl, furyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, IH-indazolyl, benzofuranyl, benzothiofuranyl, benztetrazolyl, benzo triazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles. Examples of a bicyclic heterocyclic group include, but are not limited to, quinolinyl, isoquinolinyl, phthalazinyl, quinazolinyl, indolyl, isoindolyl, indolinyl, 1H-indalzyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydroquinoxalinyl, and 1,2,3,4-tetrahydro-quinazolinyl.

The term "heteroaryl" is intended to mean stable monocyclic and polycyclic aromatic hydrocarbons that include at least one heteroatom ring member such as sulfur, oxygen, or nitrogen. Heteroaryl groups are heterocyclyl groups which are aromatic, and may include, without limitation, pyridyl, pyrrolyl, pyrimidinyl, pyrazinyl, pyridazinyl, triazinyl, furyl, quinolyl, isoquinolyl, thienyl, imidazolyl, thiazolyl, indolyl (e.g., 1H-indolyl), pyrroyl, oxazolyl, benzofuryl, benzothienyl, benzthiazolyl, isoxazolyl, pyrazolyl, triazolyl, tetrazolyl, indazolyl (e.g., 1H-indazolyl), 1,2,4-thiadiazolyl, isothiazolyl, purinyl, carbazolyl, benzimidazolyl, indolinyl, benzodioxolanyl, and benzodioxane. Heteroaryl groups may be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→0 and $S(O)_p$, wherein p is 0, 1 or 2).

The term "halo" or "halogen" includes fluoro, chloro, bromo and iodo.

As used herein, the term "substituted" refers to at least one hydrogen atom that is replaced with a non-hydrogen group, provided that normal valencies are maintained and that the substitution results in a stable compound. When a group is noted as "optionally substituted", the group may or may not contain non-hydrogen substituents. When present, the substituent(s) may be selected from alkyl, halo (e.g., chloro, bromo, iodo, fluoro), hydroxyl, alkoxy, oxo, alkanoyl, aryloxy, alkanoyloxy, amino (—$NH_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkylsulfonyl, arylsulfonyl, arylalkylsulfonyl, sulfonamide (e.g., —$SO_2NH_2$), substituted sulfonamide (e.g., —$SO_2NHalkyl$, —$SO_2NHaryl$, —$SO_2NHarylalkyl$, or cases where there are two substituents on one nitrogen selected from alkyl, aryl, or alkylalkyl), nitro, cyano, carboxy, unsubstituted amide (i.e. —$CONH_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

In cases wherein there are nitrogen atoms (e.g., amines) on compounds/complexes of the present disclosure, these may be converted to N-oxides by treatment with an oxidizing agent (e.g., mCPBA and/or hydrogen peroxides) to afford other compounds of this disclosure. Thus, shown and claimed nitrogen atoms are considered to cover both the shown nitrogen and its N-oxide (NO) derivative.

Gold(III) Complexes

The present disclosure provides mononuclear and binuclear gold(III) complexes having medicinal or pharmaceutical properties, preferably antitumor or anticancer properties. In these gold(III) complexes, each gold(III) atom is coordinated in a mixed ligand environment, preferably coordinated by (i) a dithiocarbamate ligand and (ii) either a bipyrimidine (e.g., a 2,2'-bipyrimidine) ligand or a bipyridine (e.g., a 2,2'-bypyridine) ligand. The generic structures of a dithiocarbamate, a 2,2'-bipyrimidine, and a 2,2'-bipyridine are shown below:

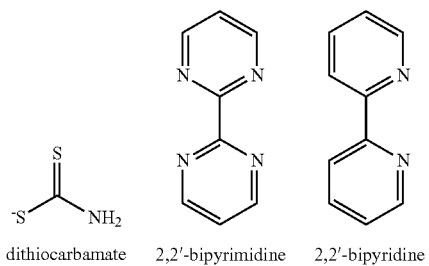

dithiocarbamate   2,2'-bipyrimidine   2,2'-bipyridine

The coordination of each of the dithiocarbamate, bipyrimidine, and bipyridine ligand to a gold(III) atom is preferably in a bidentate manner. In some embodiments, the gold(III) complex is binuclear (i.e., contains two gold(III) atoms), with a central bipyrimidine ligand that bridges the two gold(III) atoms (each gold(III) atom being coordinated in a bidentate manner to the central bipyrimidine ligand), and dithiocarbamate ligands that coordinate in a bidentate fashion to each of the gold(III) atoms. In some embodiments, the gold(III) complex is mononuclear (i.e., contains one gold(III) atom), with a single dithiocarbamate ligand and a single bipyridine ligand coordinated to the gold(III) atom in a bidentate fashion.

Gold(III) Complex of Formula (I)

In a first aspect, the present disclosure provides a gold(III) complex of formula (I),

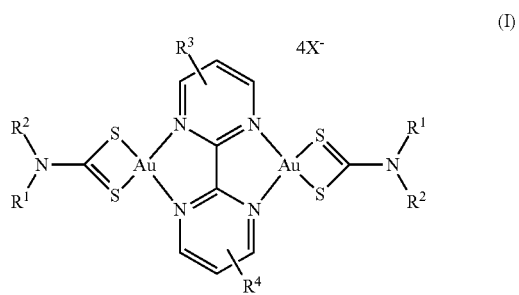

or a pharmaceutically acceptable salt, solvate, tautomer, or stereoisomer thereof,
wherein:
$R^1$ and $R^2$ are each independently a hydrogen, an optionally substituted alkyl, an optionally substituted cycloalkyl, an optionally substituted arylalkyl, or an optionally substituted aryl;
$R^3$ and $R^4$ are each independently a hydrogen, an optionally substituted alkyl, an optionally substituted cycloalkyl, an optionally substituted arylalkyl, an optionally substituted aryl, an optionally substituted heterocyclyl, an optionally substituted alkoxy, a hydroxyl, a halo, a nitro, a cyano, a N-monosubstituted amino group, or a N,N-disubstituted amino group; and
X is Cl, Br, or I.

In terms of $R^1$ and $R^2$, these substituents may be the same or different. Preferably $R^1$ and $R^2$ are the same. In some embodiments, $R^1$ and $R^2$ are each independently an optionally substituted alkyl or an optionally substituted arylalkyl. Preferably, $R^1$ is a $C_1$ to $C_8$ alkyl, preferably a $C_2$ to $C_7$ alkyl, preferably a $C_3$ to $C_6$ alkyl, or a $C_7$ to $C_{12}$ arylalkyl, preferably a $C_8$ to $C_{11}$ arylalkyl, preferably a $C_9$ to $C_{10}$ arylalkyl. In preferred embodiments, $R^1$ and $R^2$ are the same, and are each methyl, ethyl, or benzyl, most preferably methyl or ethyl.

In terms of $R^3$ and $R^4$, these substituents may be the same or different. Preferably $R^3$ and $R^4$ are the same. $R^3$ and $R^4$ may be, independently, located at a position ortho to a nitrogen atom of the bipyrimidine ring, or may be located at a position meta to both nitrogen atoms of the bipyrimidine ring. In some embodiments, $R^3$ and $R^4$ are each hydrogen, an optionally substituted alkyl (preferably a $C_1$ to $C_8$ alkyl, preferably a $C_2$ to $C_7$ alkyl, preferably a $C_3$ to $C_6$ alkyl), an optionally substituted alkoxy (preferably a $C_1$ to $C_4$ alkoxy, preferably a $C_2$ to $C_3$ alkoxy), a hydroxyl, a N-monosubstituted amino group (preferably an optionally substituted alkylamino or an optionally substituted aryalkylamino, e.g., methylamino or benzylamino), or a N,N-disubstituted amino group (preferably an amino group having two substituents selected from an optionally substituted alkyl and an optionally substituted arylalkyl, e.g., dimethylamino). In preferred embodiments, $R^3$ and $R^4$ are the same, and are each hydrogen.

In the gold(III) complex of formula (I), X represents a counteranion which is outside of the coordination sphere of the complex, i.e., not directly bound to the gold atom. As the gold(III) complex of formula (I) is binuclear (contains two gold atoms in the +3 oxidation state), with two total anionic ligands (each dithiocarbamate ligand carries a −1 charge), the gold(III) complex of formula (I) includes four $X^-$ counteranions. In preferred embodiments, X is Cl and/or Br, preferably X is Cl.

In preferred embodiments, the gold(III) complex of formula (I) is selected from the group consisting of

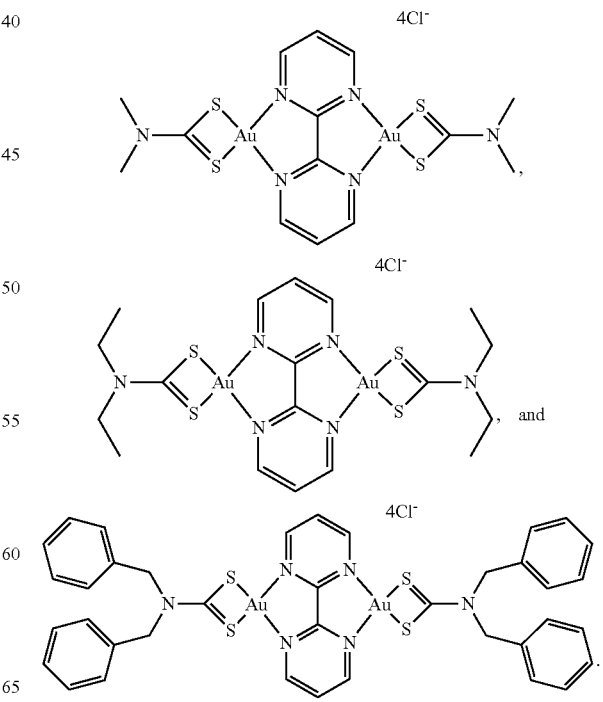

In the most preferred embodiments, the gold(III) complex of formula (I) is

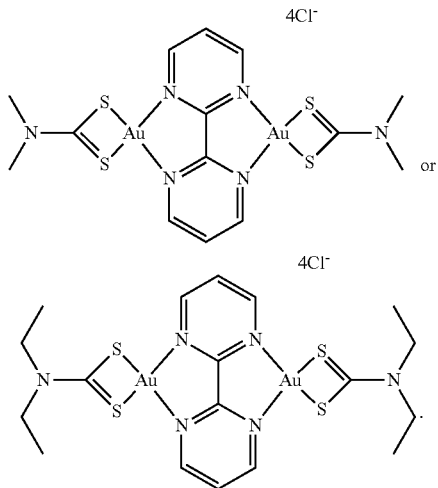

Gold(III) Complex of Formula (II)

According to a second aspect, the present disclosure also provides a gold(III) complex of formula (II).

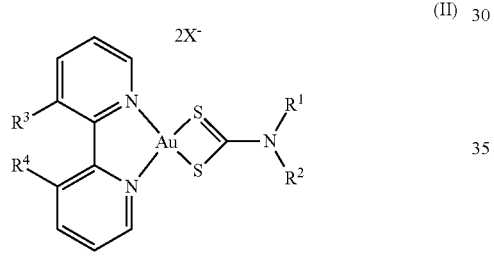

or a pharmaceutically acceptable salt, solvate, tautomer, or stereoisomer thereof,
wherein:

$R^1$ and $R^2$ are each independently a hydrogen, an optionally substituted alkyl, an optionally substituted cycloalkyl, an optionally substituted arylalkyl, or an optionally substituted aryl;

$R^3$ and $R^4$ are each independently an optionally substituted alkyl, an optionally substituted cycloalkyl, an optionally substituted arylalkyl, an optionally substituted aryl, an optionally substituted heterocyclyl, an optionally substituted alkoxy, a hydroxyl, a halo, a nitro, a cyano, a N-monosubstituted amino group, or a N,N-disubstituted amino group; and X is Cl, Br, or I.

In terms of $R^1$ and $R^2$, these substituents may be the same or different. Preferably $R^1$ and $R^2$ are the same. In some embodiments, $R^1$ and $R^2$ are each independently an optionally substituted alkyl or an optionally substituted arylalkyl. Preferably, $R^1$ is a $C_1$ to $C_8$ alkyl, preferably a $C_2$ to $C_7$ alkyl, preferably a $C_3$ to $C_6$ alkyl, or a $C_7$ to $C_{12}$ arylalkyl, preferably a $C_8$ to $C_{11}$ arylalkyl, preferably a $C_9$ to $C_{10}$ arylalkyl. In preferred embodiments, $R^1$ and $R^2$ are the same, and are each methyl, ethyl, or benzyl, most preferably methyl or ethyl.

In terms of $R^3$ and $R^4$, these substituents may be the same or different. Preferably $R^3$ and $R^4$ are the same. In some embodiments, $R^3$ and $R^4$ are each hydrogen, an optionally substituted alkyl (preferably a $C_1$ to $C_8$ alkyl, preferably a $C_2$ to $C_7$ alkyl, preferably a $C_3$ to $C_6$ alkyl), an optionally substituted alkoxy (preferably a $C_1$ to $C_4$ alkoxy, preferably a $C_2$ to $C_3$ alkoxy), a hydroxyl, a N-monosubstituted amino group (preferably an optionally substituted alkylamino or an optionally substituted aryalkylamino, e.g., methylamino or benzylamino), or a N,N-disubstituted amino group (preferably an amino group having two substituents selected from an optionally substituted alkyl and an optionally substituted arylalkyl, e.g., dimethylamino). In preferred embodiments, $R^3$ and $R^4$ are the same, and are each hydroxyl.

In the gold(III) complex of formula (II), X represents a counteranion which is outside of the coordination sphere of the complex, i.e., not directly bound to the gold atom. As the gold(III) complex of formula (II) is mononuclear (contains one gold atom in the +3 oxidation state), with one total anionic ligand (the diothiocarbamate ligand) carrying a −1 charge, the gold(III) complex of formula (II) includes two $X^-$ counteranions. In preferred embodiments, X is Cl and/or Br, preferably X is Cl.

Methods of Making

The "gold(III) complexes" (those of formula (I) and/or formula (II)) of the present disclosure may be prepared by any complexation method known to those of ordinary skill in the art. The following methods set forth below are provided for illustrative purposes and are not intended to limit the scope of the disclosure.

The gold(III) complexes may, for example, be synthesized according to a stepwise complexation route. Briefly, the gold(III) complexes may be formed by mixing together an aqueous solution of a gold(III) salt with a ligand solution of either a bipyrimidine ligand of formula (III) or a bipyridine ligand of formula (IV) to form a gold-ligand mixture.

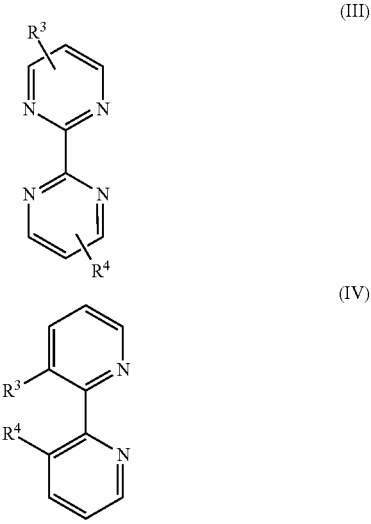

wherein $R^3$ and $R^4$ are as defined previously.

Exemplary gold(III) salts include, but are not limited to, sodium tetrachloroaurate(III), potassium tetrachloroaurate (III), cesium tetrachloroaurate(III), sodium tetrabromoaurate(III), potassium tetrabromoaurate(III), cesium tetrabromoaurate(III), as well as mixtures or hydrates thereof. Typically, a concentration of the gold(III) salt in the aqueous solution may range from 0.1 to 1.5 mM, preferably 0.2 to 1.4 mM, preferably 0.3 to 1.3 mM, preferably 0.4 to 1.2 mM, preferably 0.5 to 1.0 mM.

The ligand solution may be formed with one or more organic solvents, including, but not limited to, aromatic solvents (e.g., benzene, ethylbenzene, o-xylene, m-xylene, p-xylene, and mixtures of xylenes, toluene, mesitylene, anisole, 1,2-dimethoxybenzene, α,α,α,-trifluoromethylbenzene, fluorobenzene, heavy aromatic naptha), alkane solvents (e.g., pentane, cyclopentane, hexanes, cyclohexane, heptanes, cycloheptane, octanes), ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), chlorinated solvents (e.g. chlorobenzene, dichloromethane, 1,2-dichloroethane, 1,1-dichloroethane, chloroform, carbon tetrachloride), ester solvents (e.g. ethyl acetate, propyl acetate), ketones (e.g. acetone, butanone), formamides/acetamides (e.g., formamide, dimethyl formamide, dimethyl acetamide), monoalcohols (e.g., methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, benzyl alcohol), polyalcohols including glycols (e.g., ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, sorbitol), as well as mixtures thereof. Preferably a mixture of a monoalcohol (e.g., ethanol) and a chlorinated solvent (e.g., dichloromethane) is used as the ligand solution solvent, for example at a vol:vol ratio of 1:1 to 5:1, preferably 2:1 to 4:1, preferably 3:1. Typically, a concentration of the bipyrimidine ligand of formula (III) or the bipyridine ligand of formula (IV) in the ligand in the ligand solution may range from 0.1 to 1.5 mM, preferably 0.2 to 1.4 mM, preferably 0.3 to 1.3 mM, preferably 0.4 to 1.2 mM, preferably 0.5 to 1.0 mM.

The aqueous solution of the gold(III) complex and the ligand solution may be mixed together as is, or alternatively may be added to a monoalcohol solvent (e.g., ethanol) to form the gold-ligand mixture. When making a binuclear complex (i.e., the gold(III) complex of formula I), a mole ratio of the gold(III) salt to the bipyrimidine ligand of formula (III) typically ranges from 1.7:1 to 2.3:1, preferably 1.8:1 to 2.2:1, preferably 1.9:1 to 2.1:1, preferably 2:1. When making a mononuclear complex (i.e., the gold(III) complex of formula II), a mole ratio of the gold(III) salt to the bipyridine ligand of formula (IV) typically ranges from 0.7:1 to 1.3:1, preferably 0.8:1 to 1.2:1, preferably 0.9:1 to 1.1:1, preferably 1:1. The gold-ligand mixture may be agitated (e.g., using an agitator, a vortexer, a rotary shaker, a magnetic stirrer, a centrifugal mixer, an overhead stirrer, etc.) for any amount of time sufficient for complexation, typically from 0.5 to 10 hours, preferably 1 to 6 hours, preferably 2 to 3 hours.

A dithiocarbamate salt solution may then be mixed with the gold-ligand mixture to form a reaction mixture. The dithiocarbamate salt solution contains a dithiocarbamate salt in water or an alcohol solvent, preferably ethanol. Typically, a concentration of dithiocarbamate salt in the dithiocarbamate salt solution may range from 0.1 to 1.5 mM, preferably 0.2 to 1.4 mM, preferably 0.3 to 1.3 mM, preferably 0.4 to 1.2 mM, preferably 0.5 to 1.0 mM. A mole ratio of the dithiocarbamate salt to the gold(III) salt above used to form the gold-ligand mixture may be in a range of 0.7:1 to 1.3:1, preferably 0.8:1 to 1.2:1, preferably 0.9:1 to 1.1:1, preferably 1:1. The reaction mixture may be agitated for 0.1 to 10 hours, 0.5 to 6 hours, or 1 to 3 hours.

The dithiocarbamate salt is preferably represented by formula (V)

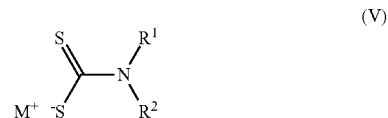

where $R^1$ and $R^2$ are as defined above, and $M^+$ is an alkali metal cation (e.g. sodium, potassium, cesium, lithium, and rubidium), ammonium, an optionally substituted alkylammonium, an optionally substituted arylammonium, or an optionally substituted alkylarylammonium. Exemplary dithiocarbamate salts include, but are not limited to, sodium dimethyldithiocarbamate, potassium dimethyldithiocarbamate, ammonium dimethyldithiocarbamate, sodium diethyldithiocarbamate, potassium diethyldithiocarbamate, ammonium diethyldithiocarbamate, sodium dibenzyldithiocarbamate, potassium dibenzyldithiocarbamate, ammonium dibenzyldithiocarbamate, and hydrates thereof.

The progress of any such reactions may be monitored by methods known to those of ordinary skill in the art, such as thin layer chromatography, gas chromatography, nuclear magnetic resonance, infrared spectroscopy, ultraviolet detection, or mass spectroscopy. Precipitation/crystallization of the gold(III) complexes may occur following the above procedures and the gold(III) complexes may be isolated and purified by methods known to those of ordinary skill in the art, such as one or more of crystallization, precipitation, filtration, solvent evaporation, drying, and the like.

Of course, it should be understood that the gold(III) complexes may be synthesized through various other synthetic schemes, reactions types and conditions, and isolation/purification procedures and still be considered a part of the present disclosure.

Pharmaceutical Compositions

The present disclosure relates to a pharmaceutical composition which comprises a therapeutically effective amount of one or more of the gold(III) complexes, formulated together with one or more pharmaceutically acceptable carriers and/or excipients, and optionally, one or more additional therapeutic agents. As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous, epidural injection, or intratumoral, as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds/complexes, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "composition" or a "pharmaceutical composition" refers to a mixture of an active ingredient(s) with other chemical components, such as pharmaceutically acceptable carriers and/or excipients. One purpose of a composition is to facilitate administration of the gold(III) complexes disclosed herein in any of their embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (e.g., oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient" or "active compound", as used herein, refers to an ingredient in the composition that is biologically active, for example, one or more of the gold(III) complexes. In some embodiments, additional therapeutic agents, in addition to the gold(III) complexes of the current disclosure, may be incorporated into a pharmaceutical composition, for example, a second active ingredient which is chemically distinct from the gold(III) complexes.

When the gold(III) complexes are administered as pharmaceuticals, to humans and animals, they can be given per se or as a pharmaceutical composition containing the active ingredient(s) in combination with a pharmaceutically acceptable carrier and/or excipient. The pharmaceutical composition may contain, for example, up to 99.9 wt. %, preferably up to 99 wt. %, preferably up to 90 wt. %, preferably up to 80 wt. %, preferably up to 70 wt. %, preferably up to 60 wt. %, preferably up to 50 wt. %, preferably up to 40 wt. %, preferably up to 30 wt. %, preferably up to 20 wt. %, preferably up to 10 wt. %, preferably up to 5 wt. %, preferably up to 1 wt. %, preferably up to 0.5 wt. %, preferably up to 0.1 wt. %, preferably up to 0.01 wt. %, preferably up to 0.001 wt. %, preferably up to 0.0001 wt. %, of the gold(III) complex, based on a total weight of the pharmaceutical composition. For example, when formulated as a solution, the pharmaceutical composition may contain 1 to 50 µM, preferably 2 to 45 µM, preferably 3 to 40 µM, preferably 4 to 35 µM, preferably 5 to 30 µM, preferably 6 to 25 µM, preferably 7 to 20 µM, preferably 8 to 15 µM, preferably 9 to 12 µM, preferably 10 to 11 µM of the gold(III) complex relative to a total volume of the pharmaceutical composition.

In some embodiments, the active ingredient of the current disclosure, e.g., the gold(III) complexes, a salt thereof, a solvate thereof, a tautomer thereof, a stereoisomer thereof, or any mixtures thereof, may provide utility as an anticancer agent in reducing the viability of cancer cells derived from human cancer cell lines including, but not limited to, breast cancer cell lines (e.g., MDA-MB-231, MCF-7, SK-BR-3, T47D, VP303); stomach cancer cell lines (e.g., N87, SNU-16, SNU-5, SNU-1, KATO III, AGS); colon/colorectal cancer cell lines (e.g., HCT-116, CACO-2, HT-29, HCT15, MDST8, GP5d, DLD1, SW620, SW403, T84); leukemia cell lines (e.g., HL-60, CESS, CCRF-CEM, CEM/C1, KASUMI-1, ARH-77); liver cancer cell lines (e.g., HepG2, PLC/PRF/5, THLE-3, C3A, SNU-182, SNU-398, SNU-387, SNU-423, SNU-475, SNU-449, and Hep 3B2.1-7); lung cancer cell lines (e.g., A549, NCI-H460, SHP-77, COR-L23/R, NCI-H69/LX20); brain tumor cell lines (e.g., U251); ovarian cancer cell lines (e.g., NCI-ADR/RES, OVCAR-03, A2780, A2780cis, OV7, PEO23); prostate cancer cell lines (e.g., DU145, PC-3); renal cancer cell lines (e.g., 786-0); skin cancer or melanoma cell lines (e.g., UACC-62, C32TG, A375, MCC26), bone cancers such as osteosarcoma cell lines (e.g., MG-63), and cervical cancer cell lines (e.g., ME-180, R-ME-180). Preferably, the active ingredient of the current disclosure, e.g., the gold(III) complexes, a salt thereof, a solvate thereof, a tautomer thereof, a stereoisomer thereof, or any mixtures thereof, provides utility as an anticancer agent in reducing the viability of cancer cells derived from bone cancers such as osteosarcoma cell lines (e.g., MG-63), lung cancer cell lines (e.g., A549, NCI-H460, SHP-77, COR-L23/R, NCI-H69/LX20), prostate cancer cell lines (e.g., DU145, PC-3), breast cancer cell lines (e.g., MDA-MB-231, MCF-7, SK-BR-3, T47D, VP303), ovarian cancer cell lines (e.g., NCI-ADR/RES, OVCAR-03, A2780, A2780cis, OV7, PEO23), and cervical cancer cell lines (e.g., ME-180, R-ME-180).

In preferred embodiments, the active ingredient of the current disclosure, e.g., the gold(III) complexes, a salt thereof, a solvate thereof, a tautomer thereof, a stereoisomer thereof, or any mixtures thereof, may provide utility as an anticancer agent in reducing the viability of cancer cells derived from human cancer cell lines which are resistant to, or which are susceptible to becoming resistant to, other therapeutic agents/chemotherapy agents such as cisplatin and doxorubicin, with specific mention being made to cisplatin and doxorubicin resistant ovarian cancers (e.g., A2780cis) and cisplatin resistant cervical cancers (e.g., R-ME-180).

In some embodiments, the cancer cells are collected from a human patient who is at risk of having, is suspected of having, has been diagnosed with, or is being monitored for recurrence of at least one type of cancer, preferably at least one of bone cancer, lung cancer, prostate cancer, breast cancer, ovarian cancer, and cervical cancer.

In some embodiments, the ability of the active ingredient to reduce the viability of cancer cells may be determined by contacting the pharmaceutical composition with the cancer cells and then performing cell viability assays. Methods of such assays include, but are not limited to, sulforhodamine-B (SRB) assay, ATP test, Calcein AM assay, clonogenic assay, ethidium homodimer assay, Evans blue assay, 2',7'-dichlorofluorescin diacetate (DCFDA) or 2',7'-dichlorodihydrofluorescein diacetate (H2DCFDA) staining assay, fluorescein diacetate hydrolysis/propidium iodide staining assay, annexin V/fluorescein isothiocyanate (FITC)/propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, 4',6'-diamidino-2-phenylindole (DAPI) assay, TUNEL assay, a fluorochrome-labeled inhibitors of caspases (FLICA)-based assay, primary (1°) colonosphere formation assay, thioredoxin reductase assay, 20S proteasome activity assay, in vitro scratch assay (for cell migration analysis).

As is well understood in the art, the IC50 value of a compound/mixture is a concentration of that compound/mixture which causes the death of 50% of the cellular population to which the compound/mixture is added. In some embodiments, the IC50 of the gold(III) complexes, the salt thereof, the solvate thereof, the tautomer thereof, the stereoisomer thereof, or mixtures thereof against bone cancer, lung cancer, prostate cancer, breast cancer, ovarian cancer, and cervical cancer cells, is less than 200 µM, preferably less than 150 µM, preferably less than 100 µM, preferably less than 90 µM, preferably less than 80 µM, preferably less than 70 µM, preferably less than 60 µM, preferably less than 50 µM, preferably less than 40 µM, preferably less than 30 µM, preferably less than 25 µM, preferably less than 20 µM, preferably less than 15 µM, preferably less than 10 µM, preferably less than 5 µM, preferably less than 4 µM, preferably less than 3 µM, preferably less than 2 µM, preferably less than 1 µM, for example, from 0.5 to 25 µM, preferably from 0.6 to 20 µM, preferably from 0.7 to 15 µM, preferably from 0.8 to 10 µM, preferably from 0.9 to 9 µM, preferably from 1 to 8 µM, preferably from 1.1 to 7 µM, preferably from 1.2 to 6 µM, preferably from 1.3 to 5 µM, preferably from 1.4 to 4 µM, preferably from 1.5 to 3 µM, preferably from 1.6 to 2 µM.

In some embodiments, additional therapeutic agents in addition to the gold(III) complexes of the current disclosure may be incorporated into the pharmaceutical composition. In some embodiments, the pharmaceutical composition includes an additional therapeutic agent that is chemically distinct from the gold(III) complex (of formula (I) or formula (II)), such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The additional therapeutic agent may be an anticancer agent and may include, but is not limited to, at least one of a mitotic inhibitor; an alkylating agent; an antimetabolite; a cell cycle inhibitor; an enzyme; a topoisomerase inhibitor (e.g., doxorubicin); a biological response modifier; an antihormone; a tubulin inhibitor; a tyrosine-kinase inhibitor; an antiangiogenic agent such as MMP-2, MMP-9 and COX-2 inhibitor; an anti-androgen; a platinum coordination complex (cisplatin, oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary additional therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, idarubicin, mitomycin, actinomycin, epirubicin; topoisomerase inhibitors including doxorubicin, irinotecan, mitoxantrone, topotecan, and mixtures thereof.

As used herein, the phrase "pharmaceutically acceptable carrier and/or excipient" means a pharmaceutically acceptable material, composition or vehicle, such as a liquid or solid filler, carrier, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, castor oil, and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol and/or other organic solvents (e.g., DMSO); (20) pH buffered solutions; (21) polyesters, polycarbonates and/or polyanhydrides; and/or (22) other non-toxic compatible substances employed in pharmaceutical formulations, such as cyclodextrins, liposomes, micelle forming agents, e.g., bile acids, polyethoxylated oils (e.g., polyethoxylated castor oil) just to name a few.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Methods of preparing these pharmaceutical compositions include the step of bringing into association the gold(III) complex with the pharmaceutically acceptable carrier and/or excipient, and, optionally, one or more accessory ingredients. In general, the compositions are prepared by uniformly and intimately bringing into association a gold(III) complex of the present disclosure with liquid carriers, or finely divided solid carriers, or both, and then, if necessary, shaping the product.

Pharmaceutical compositions of the present disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a gold(III) complex as an active ingredient. A gold(III) complex of the present disclosure may also be administered as a bolus, electuary or paste.

In solid dosage forms of the present disclosure for oral administration (capsules, tablets, pills, dragees, powders, granules, troches and the like), the active ingredient is mixed with one or more pharmaceutically acceptable carriers and/ or excipients, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants (e.g., fatty acid esters of sorbitan and polyalkolyated fatty acid esters of sorbitan such as TWEEN 80, available from Sigma-Aldrich); (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent. The tablets, and other solid dosage forms of the pharmaceutical compositions of the present disclosure may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the complexes of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compound, may contain suspending agents as, for example, ethoxylated isostearyl alcohols, polyoxyethylene sorbitol and sorbitan esters (including polyoxyethylene fatty acid esters of sorbitan, e.g., TWEEN 80), microcrystalline cellulose, aluminum metahydroxide, bentonite, agar-agar and tragacanth, and mixtures thereof. In preferred embodiments, the pharmaceutical composition is in the form of a suspension, comprising, consisting of, or consisting essentially of the gold(III) complex and the pharmaceutically acceptable carrier and/or excipient, which is preferably a suspending agent (preferably a polyoxyethylene sorbitan ester, preferably a polyoxyethylene fatty acid ester of sorbitan, e.g., TWEEN 80) in an inert diluent (preferably water). Preferably the content of the suspending agent in the suspension ranges from 0.01 to 1 wt. %, preferably 0.05 to 0.8 wt. %, preferably 0.1 to 0.6 wt. %, preferably 0.5 wt. %, based on a total weight of the suspension.

Formulations of the pharmaceutical compositions of the disclosure for rectal or vaginal administration may be presented as a suppository, which may be prepared by mixing one or more gold(III) complexes with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound(s).

Formulations of the pharmaceutical compositions which are suitable for vaginal administration also include pessaries, tampons, creams, gels, pastes, foams or spray formulations containing such carriers as are known in the art to be appropriate.

Dosage forms for the topical or transdermal administration of a gold(III) complex of this disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active gold(III) complex of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a gold(III) complex of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a gold(III) complex of the present disclosure to the body. Such dosage forms can be made by dissolving or dispersing the gold(III) complex in the proper medium. Absorption enhancers can also be used to increase the flux of the gold(III) complex across the skin.

The rate of such flux can be controlled by either providing a rate controlling membrane or dispersing the gold(III) complex in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more gold(III) complexes of the present disclosure in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers (e.g., phosphate buffered saline, PBS), bacteriostats, solvents, polyalkoxylated oils such as polyethoxylated castor oil (e.g., CREMOPHOR from Sigma-Aldrich), solutes which render the formulation isotonic with the blood of the intended recipient or suspending or thickening agents.

Examples of suitable aqueous and non-aqueous carriers which may be employed in the pharmaceutical compositions of the disclosure include water, ethanol, DMSO, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants (e.g., TWEEN 80).

These compositions may also contain adjuvants such as preservatives, wetting agents, emulsifying agents and dispersing agents. Prevention of the action of microorganisms upon the subject gold(III) complexes may be ensured by the inclusion of various antibacterial and antifungal agents, for example, paraben, chlorobutanol, phenol sorbic acid, and the like. It may also be desirable to include isotonic agents, such as sugars, sodium chloride, and the like into the pharmaceutical compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject gold(III) complexes in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions which are compatible with body tissue.

In preferred embodiments, the pharmaceutical compositions of this disclosure are formulated for parenteral administration, preferably intratumoral injection, preferably intratumoral injection using a pharmaceutically acceptable carrier and/or excipient made of 5 to 15 vol. %, preferably 8 to 12 vol. %, preferably 10 vol. % DMSO, 15 to 25 vol. %, preferably 18 to 22 vol. %, preferably 20 vol. % polyethoxylated castor oil (e.g., CREMOPHOR from Sigma-Aldrich), and 65 to 75 vol. %, preferably 68 to 72 vol. %, preferably 70 vol. % buffer (e.g., PBS buffer).

In some embodiments, the pharmaceutical composition contains 1 to 99.9999 wt. %, preferably 5 to 99.999 wt. %, preferably 10 to 99.99 wt. %, preferably 15 to 99 wt. %, preferably 20 to 90 wt. %, preferably 30 to 85 wt. %, preferably 40 to 80 wt. %, preferably 50 to 75 wt. % of the pharmaceutically acceptable carrier and/or excipient, relative to a total weight of the pharmaceutical composition.

Therapeutic Applications and Methods

According to another aspect, the present disclosure relates to a method for treating a proliferative disorder. The method involves administering a therapeutically effective amount of one or more gold(III) complexes per se, or a pharmaceutical composition described above to a subject.

In some embodiments, the proliferative disorder is cancer. Types of cancers that may be treated with the gold(III) complexes of this disclosure include, but are not limited to, brain cancers, skin cancers, bladder cancers, ovarian cancers, breast cancers, gastric cancers, pancreatic cancers, prostate cancers, colon/colorectal cancers, blood cancers, lung cancers, cervical cancers, and bone cancers. In some embodiments, the gold(III) complexes of this disclosure can be used for the treatment of any cancer type that fails to undergo apoptosis in a patient. This includes, but is not limited to: solid tumors, including but not limited to carcinomas; sarcomas including Kaposi's sarcoma and osteosarcoma; erythroblastoma; glioblastoma; meningioma; astrocytoma; melanoma; and myoblastoma. Treatment or prevention of non-solid tumor cancers, such as leukemia, is also contemplated by this invention.

Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Bur-kitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse laige B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma. In preferred embodiments, the cancer is at least one of bone cancer, lung cancer, prostate cancer, breast cancer, ovarian cancer, and cervical cancer.

As used herein, the terms "treat", "treatment", and "treating" in the context of the administration of a therapy to a subject in need thereof refers to the reduction or inhibition of the progression and/or duration of a disease (e.g., cancer), the reduction or amelioration of the severity of the disease, the amelioration of one or more symptoms thereof resulting from the administration of one or more therapies, preventing the disease from occurring in a subject that may be predisposed to the disease but does not yet experience or exhibit symptoms of the disease (prophylactic treatment), slowing or arresting disease development, ameliorating the disease, providing relief from the symptoms or side-effects of the disease (including palliative treatment), and causing regression of the disease. Specific to cancer, and in particular bone, lung, prostate, breast, ovarian, and cervical cancers, these terms may refer to: (1) a stabilization, reduction (e.g., by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g., by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g., colectomy, mastectomy), and (14) preventing or reducing (e.g., by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g., a rat, a mouse, and a guinea pig. In preferred embodiments, the subject is a human.

The subject may be any subject already with the disease, a subject which does not yet experience or exhibit symptoms of the disease, or a subject predisposed to the disease. In preferred embodiments, the subject is a person who is predisposed to cancer, e.g., a person with a family history of cancer. Women who have (i) certain inherited genes (e.g., mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting breast cancer. People who (i) consumes a diet high in salty and smoked foods and/or low in fruits and vegetables, (ii) had infection with *Helicobacter pylori*, and/or (iii) long-term stomach inflammation are at a higher risk of contracting stomach cancer. People who (i) had chemotherapy and radiation therapy for other cancers, (ii) has genetic disorders, such as Down syndrome, and/or (iii) exposure to certain chemicals, such as benzene are at a higher risk of contracting leukemia.

People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. People who have been diagnosed with Human papillomavirus (HPV) are at a higher risk of contracting cervical cancer. Any subject with such predispositions, in combination with sound medical judgment, may be candidates for the treatment methods described herein.

In some embodiments, the subject has leukemia, stomach, colon, testicular, bladder, head and neck cancer, esophageal cancer, mesothelioma, brain, neuroblastoma, bone, lung, prostate, breast, ovarian, and/or cervical cancer and is currently undergoing, or has completed one or more chemotherapy regimens. In some embodiments, the subject has been previously administered/treated with, or is being currently administered/treated with, a thymidylate synthase inhibitor (e.g., capecitabine, fluorouracil (5-FU)), a thymidine phosphorylase (TPase) inhibitor (e.g., tipiracil, trifluridine), a topoisomerase I inhibitor (e.g., irinotecan), a topoisomerase II inhibitor (e.g., doxorubicin), a DNA synthesis inhibitor (e.g., oxaliplatin), a DNA crosslinking agent (e.g., cisplatin), and/or a targeted therapy (e.g., cetuximab, bevacizumab, panitumumab, ziv-aflibercept, ramucirumab). In some embodiments, the subject has been previously administered/treated with, or is being currently administered/treated with, a tubulin binding drug such as paclitaxel, epothilone, docetaxel, discodermolide, etoposide, vinblastine, vincristine, teniposide, vinorelbine, and vindesine, and developed resistance to the tubulin binding drug. In some embodiments, the subject has been previously administered/treated with, or is being currently administered/treated with, a tyrosine-kinase inhibitor such as imatinib, nilotinib, dasatinib, bosutinib, ponatinib, and bafetinib, and developed drug resistance via (i) Bcr-Abl dependent mechanisms involving Bcr-Abl duplication, Bcr-Abl mutation, T315I mutation, and/or P-loop mutations, or (ii) Bcr-Abl Independent mechanisms involving drug efflux caused by P-glycoproteins, drug import by organic cation transporter 1, and/or alternative signaling pathway activation. In some embodiments, the subject has been previously administered/treated with, or is being currently administered/treated with, a DNA crosslinking agent (e.g., cisplatin) and developed drug resistance via mechanisms related to decreased intracellular uptake, increased reflux, increased inactivation by sulfhydryl molecules such as glutathione, increased excision of the adducts from DNA by repair pathways, increased lesion bypass, and/or altered expression of regulatory proteins involved in signal transduction pathways that control the apoptotic processes. In some embodiments, the subject has been previously administered/treated with, or is being currently administered/treated with, a topoisomerase II inhibitor (e.g., doxorubicin), and developed drug resistance mechanisms via alteration or increased expression of transporters including, but not limited to, one or more of ABCB1 (MDR1, Pgp) and ABCC1 (MRP1), as well as other transporters.

The terms "administer", "administering", "administration", and the like, as used herein, refer to the methods that may be used to enable delivery of the active ingredient and/or the pharmaceutical composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, intratumoral, or infusion), topical and rectal administration. Those of ordinary skill in the art are familiar with administration techniques that can be employed. In preferred embodiments, the active ingredient (e.g., the gold(III) complexes) or the pharmaceutical composition described herein are administered parenterally, preferably as intratumoral injections, preferably as a sterile isotonic aqueous or non-aqueous solution, dispersion, suspension or emulsion.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. Typically, an effective amount of the gold(III) complex (e.g., to treat cancers such as bone cancer, lung cancer, prostate cancer, breast cancer, ovarian cancer, and cervical cancer, in terms of mg of the gold(III) complex per body weight of the subject (kg), ranges from 0.01 to 100 mg/kg, preferably 0.05 to 90 mg/kg, preferably 0.1 to 80 mg/kg, preferably 0.5 to 70 mg/kg, preferably 1 to 60 mg/kg, preferably 1.2 to 50 mg/kg, preferably 1.4 to 40 mg/kg, preferably 1.6 to 30 mg/kg, preferably 1.8 to 20 mg/kg, preferably 2 to 10 mg/kg, preferably 2.2 to 5 mg/kg, preferably 2.4 to 3 mg/kg, preferably 2.5 mg/kg.

Gold(III) complexes of the disclosure may be useful for sensitizing cells to apoptotic signals. Thus, in some embodiments, the gold(III) complexes of the disclosure are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin ortopotecan; (vii) topoisomerase II poisons, (viii) microtubule-directed agents, (ix) kinase inhibitors (x) miscellaneous investigational agents (xi) hormones, (xii) hormone antagonists, and (xii) targeted therapies. It is contemplated that gold(III) complexes of the disclosure may be useful in combination with any known agents falling into the above 13 classes as well as any future agents that are currently in development. In particular, it is contemplated that gold(III) complexes of the disclosure may be useful in combination with current Standards of Care as well as any that evolve over the foreseeable future. Specific dosages and dosing regimens would be based on physicians' evolving knowledge and the general skill in the art.

Examples of second therapeutic agents include, but are not limited to, a mitotic inhibitor; an alkylating agent; an antimetabolite; a cell cycle inhibitor; an enzyme; a topoisomerase inhibitor; a biological response modifier; an antihormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin, cisplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane); a thymidylate synthase inhibitor; a thymidine phosphorylase (TPase) inhibitor; a DNA synthesis inhibitor; and/or a targeted therapy. Exemplary second therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan; thymidine phosphorylase (TPase) inhibitors such as tipiracil and trifluridine; DNA synthesis inhibitors such as oxaliplatin; targeted therapies such as cetuximab, bevacizumab, panitumumab, zivaflibercept, ramucirumab; and mixtures thereof.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Any other administration route combination is also contemplated herein according to the administration routes available for each of the therapeutic agents. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A treatment method may comprise administering the gold(III) complex or a pharmaceutical composition containing the gold(III) complex of the current disclosure in any of its embodiments as a single dose or multiple individual divided doses. In some embodiments, the composition is administered at various dosages (e.g., a first dose with an effective amount of 10 mg/kg and a second dose with an effective amount of 2 mg/kg). In some embodiments, the interval of time between the administration of the pharmaceutical composition and the administration of one or more second therapies may be about 1 to 5 minutes, 1 to 30 minutes, 30 minutes to 60 minutes, 1 hour, 1 to 2 hours, 2 to 6 hours, 2 to 12 hours, 12 to 24 hours, 1 to 2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11 to 15 weeks, 15 to 20 weeks, 20 to 30 weeks, 30 to 40 weeks, 40 to 50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In some embodiments, the pharmaceutical composition and optionally one or more second therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In some embodiments, the size of a tumor after treatment is not reduced but is maintained at the same size as before treatment. Methods of assessing tumor size include, but are not limited to, CT scan, MRI, DCE-MRI, PET scan, and manual tumor measurements.

The method may further comprise measuring a concentration of a biomarker and/or detecting a mutation in a biomarker before and/or after the pharmaceutical composition comprising the gold(III) complex of the present disclosure is administered. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERB. Exemplary biomarkers for stomach cancer include, without limitation, carcinoembryonic antigen (CEA), CA19-9, carbohydrate antigen (CA) 72-4, alpha-fetoprotein, carbohydrate antigen (CA)12-5, SLE, BCA-225, hCG, and pepsinogen I/II. Exemplary biomarkers for lung cancer include, without limitation, CYFRA 21-1 (cytokeratins), EPCAM (epithelial cell adhesion molecule), ProGRP (pro-gastrin-releasing peptide), and CEACAM (carcinoembryonic antigen). Exemplary biomarkers for prostate cancer include, without limitation, PSA, hK2/fourkallikrein panel, EN@, Annexin A3, PCA3, and TMPRSS2-ERG. Exemplary biomarkers for ovarian cancer include, without limitation, CEA, cancer antigen 125 (CA125), risk of ovarian malignancy algorithm serum biomarkers (ROMA), human epididymis protein 4 (HE4). Exemplary biomarkers for cervical cancer include, without limitation HPV E6, HPV E7, Mini chromosome maintenance (MCM), Cell division cycle protein 6 (CDC6), $p16^{INK4A}$, Squamous cell carcinoma antigen (SCC), and Ki-67.

Potentially predictive cancer biomarkers include, without limitation, mutations in genes BRCA1 and BRCA2 for breast cancer, overexpressions of TYMS, mutations in genes p53 and KRAS for colon cancer, and high concentration levels of AFP, and overexpressions of HSP90a for liver cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The concentration level of the cancer biomarker in a sample (i.e., biological sample obtained from the subject in need of therapy including a single cell, multiple cells, fragments of cells, a tissue sample, and/or body fluid, for example red blood cells, white blood cells, platelets, hepatocytes, epithelial cells, endothelial cells, a skin biopsy, a mucosa biopsy, an aliquot of urine, saliva, whole blood, serum, plasma, lymph) may be measured for example by an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the gold(III) complex by at least 5%, at least 10%, or at least 30%, and up to 80%, up to 60%, or up to 50% of an initial effective amount. The subject may be administered with the increased dosage for a longer period (e.g., 1 week more, 2 weeks more, or 2 months more) than the duration prescribed with the initial effective amount.

In some embodiments, the administration is stopped once the subject is treated.

The examples below are intended to further illustrate protocols for preparing, characterizing, and using the complexes of the present disclosure, and are not intended to limit the scope of the claims.

Where a numerical limit or range is stated herein, the endpoints are included. Also, all values and subranges within a numerical limit or range are specifically included as if explicitly written out.

The terms "comprise(s)", "include(s)", "having", "has", "can", "contain(s)", and variants thereof, as used herein, are intended to be open-ended transitional phrases, terms, or words that do not preclude the possibility of additional acts or structures. The present disclosure also contemplates other embodiments "comprising", "consisting of" and "consisting essentially of", the embodiments or elements presented herein, whether explicitly set forth or not.

As used herein, the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

Results

The structures of eight new gold(III) complexes (C1-C8) are shown in FIGS. 1A-1H (BPYH, 2 2'-bipyridine-3,3'-diol; BPM, 2,2'-bipyrimidine; DMDTC, dimethyldithiocarbamate; DEDTC, diethyldithiocarbamate; DBDTC, dibenzyldithiocarbamate). Four molecules (complexes C1-C4) have a 2,2'-bipyridine-3,3'-diol (BPYH) moiety and a single gold atom, while the others (complexes C5-C8) have a 2,2'-bipyrimidine (BPM) moiety and two gold atoms. Complexes C2 and C6 are dimethyldithiocarbamates, C3 and C7 are diethyldithiocarbamates, and C4 and C8 are dibenzyldithiocarbamates. The gold(III) complexes had >99% purity, and interacted with lysozyme, tryptophan and guanine (see the Supplementary Materials and Methods section below).

In Vitro Cytotoxicity of Gold(III) Complexes

To evaluate the potential anticancer activity of the eight complexes, their in vitro cytotoxicity was compared to that of cisplatin in a panel of cell lines derived from different human cancers including lung cancer (A549), androgen-sensitive prostate cancer (DU145), androgen-resistant prostate cancer (PC3), breast cancer (MCF-7), and osteosarcoma (MG-63) (Table 1).

TABLE 1

Half-maximal inhibitory concentrations ($IC_{50}$) of cisplatin and new gold(III) complexes C1-C8 in human lung, prostate, breast and osteosarcoma cancer cell lines.

| Compound | Cell line | | | | |
|---|---|---|---|---|---|
| | A549 | DU145 | PC3 | MCF-7 | MG63 |
| Cisplatin | 52.0 (4.7) | 4.5 (0.4) | 3.3 (0.3) | 22.2 (0.2) | 58.0 (0.5) |
| C1 | >80 | 39.0 (3.5) | 28.3 (2.6) | 59.0 (5.3) | 43.0 (3.9) |
| C2 | 6.1 (0.6) | 2.8 (0.3) | 1.5 (0.1) | 2.3 (0.2) | 3.8 (0.3) |
| C3 | 3.8 (0.3) | 3.5 (0.3) | 1.3 (0.1) | 1.7 (0.2) | 1.2 (0.1) |
| C4 | 25.0 (2.3) | 6.4 (0.6) | 8.5 (0.8) | 13.0 (1.2) | 12.3 (1.1) |
| C5 | >80 | >80 | >80 | 65.0 (5.9) | 26.0 (2.3) |
| C6 | 0.8 (0.1) | 0.7 (0.1) | 0.6 (0.1) | 0.5 (0.1) | 0.8 (0.1) |
| C7 | 1.4 (0.1) | 0.8 (0.1) | 0.8 (0.1) | 0.6 (0.1) | 0.7 (0.1) |
| C8 | 23.0 (2.1) | 22.8 (2.1) | 19.5 (1.8) | 9.5 (0.9) | 5.8 (0.5) |

Values are mean (SD) expressed in μM.

Cisplatin had relatively low potency on three cell lines (A549, MCF-7 and MG-63), with half maximal inhibitory concentrations ($IC_{50}$)>10 μM, while it was more potent on the DU145 and PC3 prostate cancer cell lines with mean IC50 values of 4.5 μM and 3.3 μM, respectively. Complex C1 had $IC_{50}$ values higher than that of cisplatin in most cell lines, indicating lower potency, while in MG-63 the two drugs had similar activities. Complexes C2 and C3 were more potent than cisplatin in all cell lines, and had IC50 values more than one order of magnitude lower than cisplatin in the cisplatin-resistant MCF-7, A549 and MG-63 cell lines. Complexes C4 and C8 were less cytotoxic than cisplatin in PC3 and DU145 cells but more cytotoxic than cisplatin in MCF-7, A549 and MG-63 cells. Complex C5 exerted very low cytotoxic effects on most cell lines except for MG-63. Complex C6 and C7 had submicromolar IC50 values in almost all cell lines, and thus were the most potent of all complexes tested, including cisplatin.

The cytotoxic effects of the gold(III) complexes were also evaluated in two cell lines for which a cisplatin-resistant clone was available. First, in the ovarian cancer cell line A2780 (cisplatin sensitive), complexes C2, C3, C6 and C7 were more potent than cisplatin (i.e. they had $IC_{50}$ values <1.5 μM), whereas complexes C1, C4, C5 and C8 were less potent (Table 2).

TABLE 2

Half-maximal inhibitory concentrations ($IC_{50}$) of reference drugs and gold(III) complexes, in ovarian cancer cell line A2780 and its cisplatin- and doxorubicin-resistant A2780cis clone, and fold resistance (FR).

| Compound | $IC_{50}$, μM[a] | | FR |
|---|---|---|---|
| | A2780 | A2780cis | (A2780cis/A2780) |
| Cisplatin | 1.5 (0.1) | 10.4 (0.9) | 6.9 |
| Doxorubicin | 0.02 (0.0) | 0.12 (0.0) | 9.0 |
| C1 | 23.0 (2.1) | 24.0 (2.0) | 1.0 |
| C2 | 0.9 (0.1) | 0.8 (0.1) | 0.9 |
| C3 | 0.4 (0.0) | 0.4 (0.0) | 1.1 |
| C4 | 7.3 (0.7) | 8.2 (0.7) | 1.1 |
| C5 | 15.4 (1.4) | 16.2 (5.1) | 1.1 |
| C6 | 0.2 (0.0) | 0.3 (0.0) | 1.2 |
| C7 | 0.4 (0.0) | 0.3 (0.0) | 0.9 |
| C8 | 3.8 (0.3) | 5.2 (0.5) | 1.4 |

[a]Mean (SD)

In the cisplatin- and doxorubicin-resistant clone A2780cis, the $IC_{50}$ of each gold(III) complex was similar to that in the parental cell line, but because the $IC_{50}$ of cisplatin was higher, complexes C2, C3, C4, C6, C7 and C8 were all more potent than the reference drug. The fold resistance (FR) between the two cell lines ($IC_{50}$ A2780cis/$IC_{50}$ A2780) was 6.9 for cisplatin and 9.0 for doxorubicin, while for the eight test complexes it was close to unity (range, 0.9 to 1.4). This result excludes the phenomenon of cross-resistance to these two drugs in these cell lines.

A similar experiment was done using the ME-180 cervical cancer cell line and its cisplatin-resistant clone R-ME-180 (Table 3). In ME-180 cells, complexes C2, C3, C6 and C7 were more potent than cisplatin (i.e. they had $IC_{50}$ values <15 μM) and complexes C1, C4, and C5 were less active. In R-ME-180 cells, the $IC_{50}$ value for cisplatin was higher, giving FR=4.5. The FR for the test complexes (excluding C5) was lower, ranging from 0.9 (C7) to 1.5 for C2.

TABLE 3

Half-maximal inhibitory concentrations ($IC_{50}$) of cisplatin and gold(III) complexes, in cervical cancer cell line ME-180 and its cisplatin-resistant R-ME-180 clone, and fold resistance (FR).

| Com- | $IC_{50}$, μM[a] | | FR |
|---|---|---|---|
| pound | ME-180 | R-ME-180 | (R-ME-180/ME-180) |
| Cisplatin | 15.0 (1.4) | 68.0 (6.1) | 4.5 |
| C1 | 70.0 (6.3) | 72.0 (6.5) | 1.0 |
| C2 | 14.0 (1.3) | 21.0 (1.9) | 1.5 |
| C3 | 3.0 (0.3) | 3.8 (0.3) | 1.3 |
| C4 | 30.0 (2.5) | 30.0 (2.7) | 1.0 |
| C5 | >80 | >80 | ND |
| C6 | 5.3 (0.5) | 4.9 (0.5) | 0.9 |
| C7 | 4.8 (0.4) | 4.1 (0.4) | 0.9 |
| C8 | 15.0 (1.4) | 16.0 (1.4) | 1.0 |

ND, not determined.
[a]Mean (SD)

Figure 15:
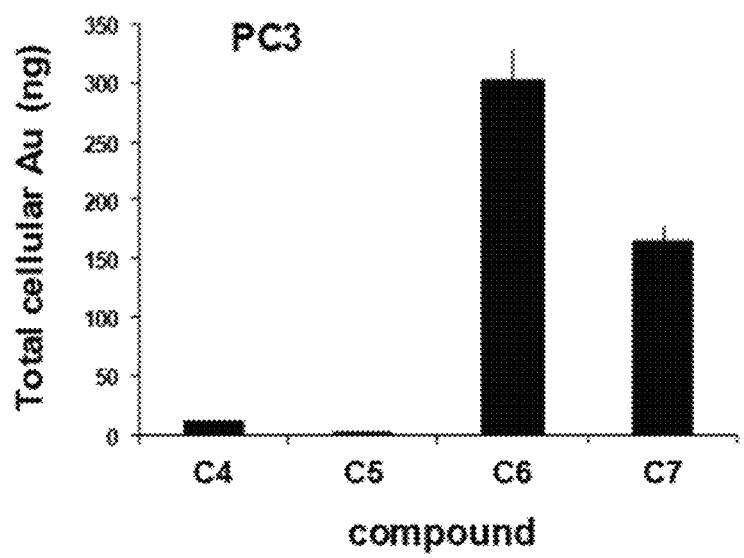
FIG. 15 is a graph illustrating the uptake of selected gold(III) complexes by PC3 cells, where PC3 cells ($1\times10^6$ cells/dish) were treated for 2 h with 3 μM C4, C5, C6 or C7, and internalized gold was determined by ICP mass spectrometry, with results presented as means and SD of three independent experiments.

Then, the cellular uptake of the gold(III) complexes was examined. PC3 cells were incubated separately with two low-potency complexes C4 and C5 and two high-potency complexes C6 and C7, and the amount of internalized gold was determined by mass spectrometry (FIG. 15). This analysis showed greater uptake of the two more potent molecules, with C6 internalization even greater than that of C7.

Figure 16:
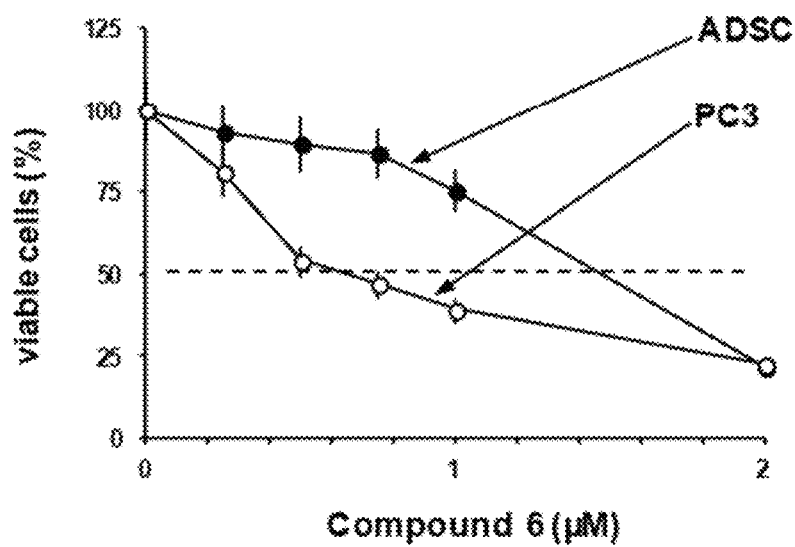
FIG. 16 is a graph illustrating the growth inhibition curves for C6 in PC3 prostate cancer cells and adipose-derived stromal cells (ADSCs), where cell viability was determined with the MTT assay after 72 h drug treatment, and the results are presented as means and SD for three replicate wells from three independent experiments.

To further investigate the cytotoxicity of C6 ([Au$_2$(BPM) (DMDTC)$_2$]Cl$_4$), its effects were compared on growth of PC3 cells and normal human adipose-derived stromal cells. This analysis showed that C6 was more potent in the prostate tumor cells ($IC_{50}$=0.6 μM) than in the normal stromal cells ($IC_{50}$=1.4 μM) (FIG. 16).

Altogether, these experiments show that complexes C2, C3, C6 and C7 have the greatest potency (lowest $IC_{50}$ values) in the panel of investigated tumor cell lines. Results from pairs of cell lines that differ in susceptibility to cisplatin (ME-180 and R-ME180) and also to doxorubicin (A2780 and A2780cis) rule out cross-resistance to the two chemotherapy agents.

Cellular Mechanism of Action of Complex C6

Figure 2A:
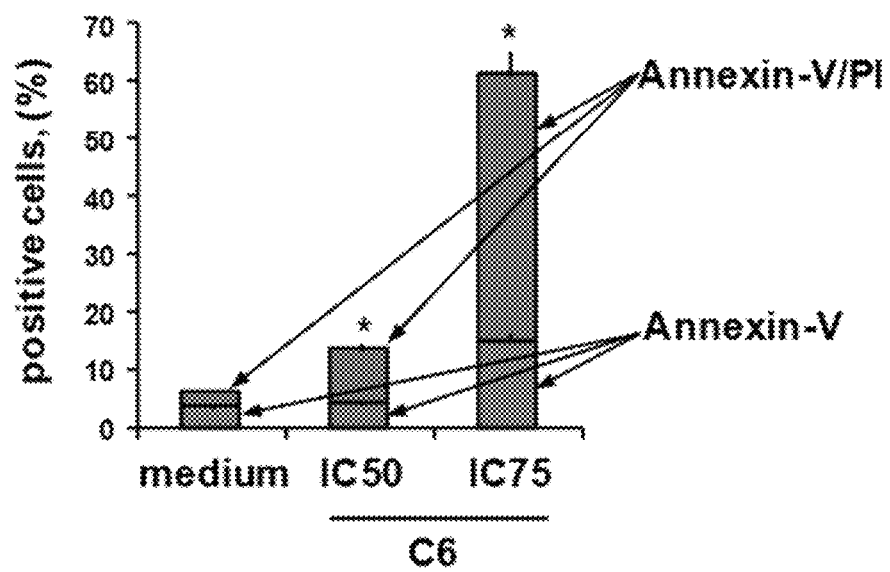
FIG. 2A is a graph showing the percentage of annexin-V-positive cells and Annexin-V-propidium iodide (PI)-positive cells using PC3 cells cultured in complete medium alone or with complex C6, at the half-maximal inhibitory concentration (IC50), at IC25, or IC75, for 24 h, illustrating the induced apoptosis/cell cycle block from complex C6.
Figure 2B:
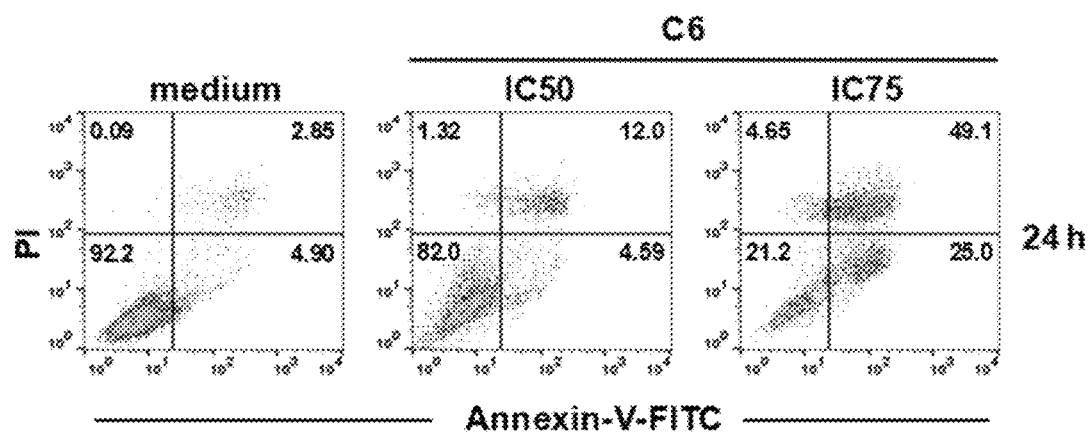
FIG. 2B shows representative flow cytometry plots of the Annexin-V-FITC and propidium iodide (PI) assay of apoptosis evaluated by flow cytometry using the conditions of FIG. 1A, where the percentages of stained cells are reported.
Figure 2C:
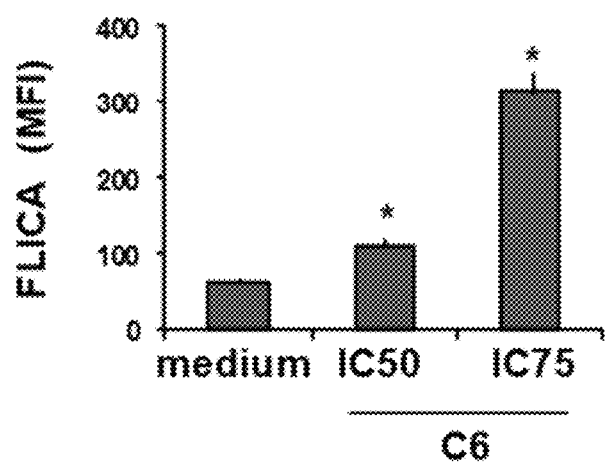
FIG. 2C is a graph illustrating Caspase 3,7 activation assay evaluated by flow cytometry with fluorochrome-labeled inhibitors of caspases (FLICA) in terms of mean fluorescence intensity (MFI) of FLICA under the conditions of FIG. 1A.
Figure 2D:
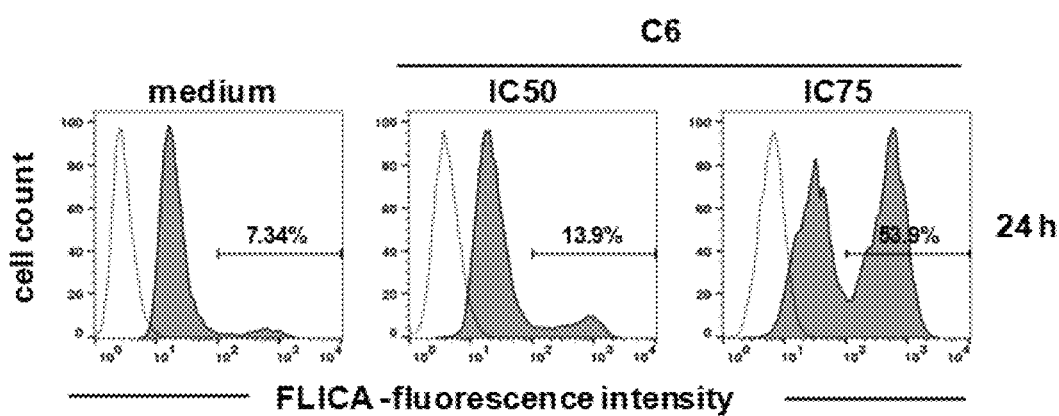
FIG. 2D shows representative flow cytometry histograms of caspase 3,7 activation by C6 treatment according to FIG. 1C where the percentage of FLICA-positive cells is reported.
Figure 2E:
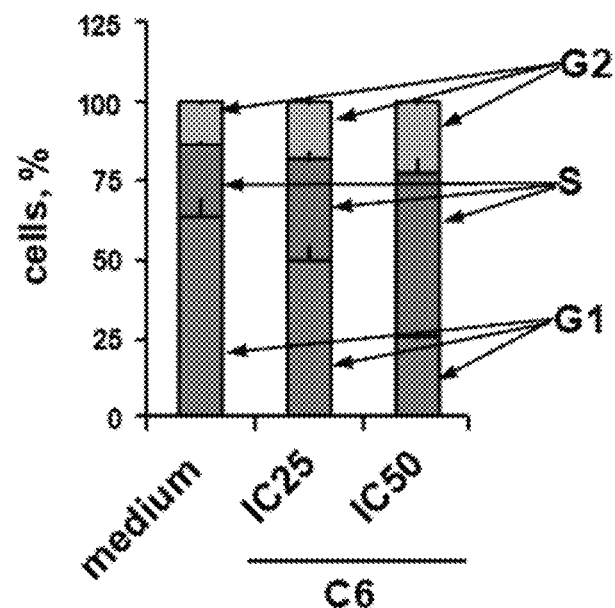
FIG. 2E shows the cell cycle progression determined by PI staining in terms of percentage distribution of PC3 cells in different cell cycle phases under the conditions of FIG. 1A.
Figure 2F:
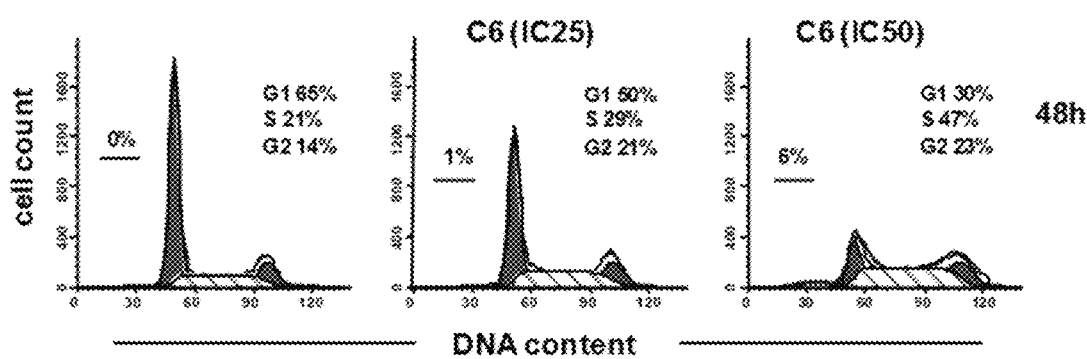
FIG. 2F shows representative flow cytometry histograms of cell cycle progression of FIG. 3E.

C6 was chosen for further analyses with the PC3 prostate cancer cell line. When PC3 cells were incubated with C6 at its $IC_{50}$ (0.62 μM) and $IC_{75}$ (1.85 μM), there was a dose-dependent increase in the percentage of annexin-V-positive cells, indicating early apoptosis, and also of double stained annexin-V- and propidium iodide (PI)-positive cells, indicating late apoptosis (FIGS. 2A and 2B). Consistently, treatment with C6 activated caspase 3,7, evaluated using fluorochrome-labeled inhibitors of caspases (FLICA) that irreversibly bind active caspase (FIGS. 2C and 2D). These results suggest that apoptosis is involved in tumor cell death by C6. Finally, treatment of PC3 cells with C6 modified the distribution of cells in the cell cycle, by increasing the percentage of cells in S phase and decreasing that in G1 compared to untreated cells (FIGS. 2E and 2F). In FIGS. 2A-2F, all bar charts report means and SD of three independent experiments and statistical analysis was performed using one-way ANOVA, followed by Dunnett's multiple comparisons test, *P<0.05 vs medium.

Figure 3A:
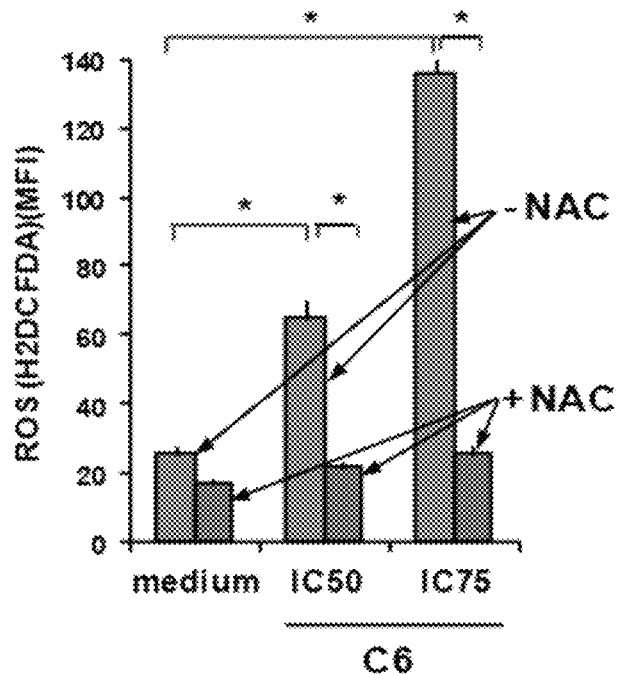
FIG. 3A is a graph illustrating reactive oxygen species (ROS) generation-by PC3 cells in terms of mean fluorescence intensity (MFI) when exposed to medium alone or complex C6 at its IC50 and IC75 for 24 h, in the presence or absence of the ROS scavenger N-acetyl cysteine (NAC) (added 30 minutes before drug treatment), where ROS were detected using H2DCFDA, showing that the complex C6 increases ROS generation.
Figure 3B:
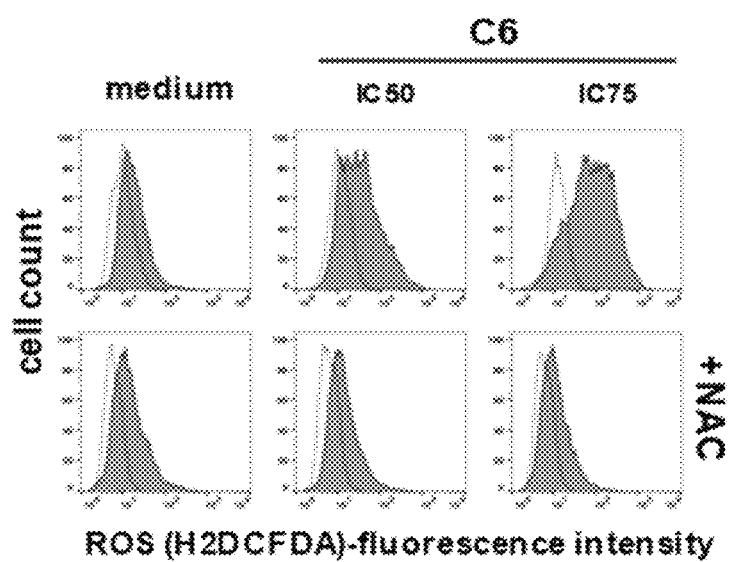
FIG. 3B shows representative flow cytometry histograms of generated ROS from FIG. 1A.
Figure 3C:
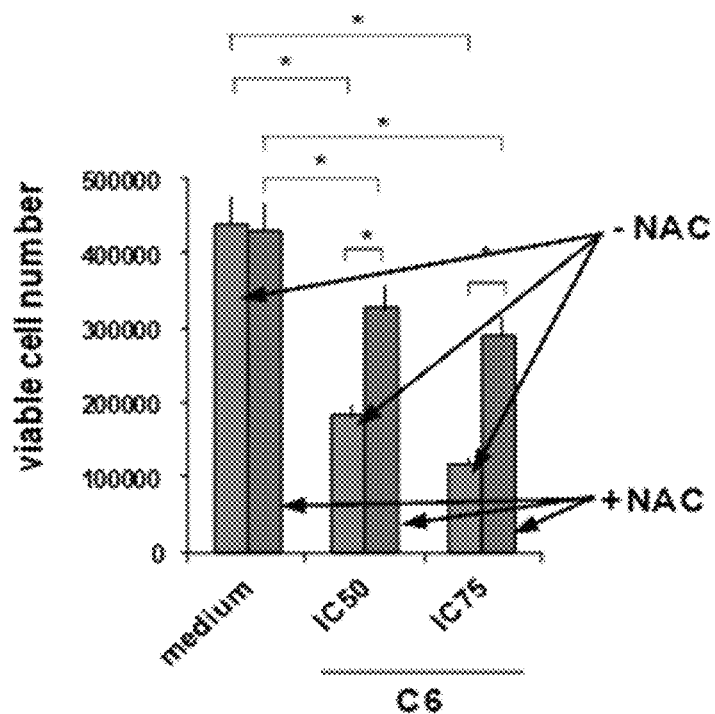
FIG. 3C is a graph showing the number of viable cells 24 h after treatment with C6 and NAC (NAC, added 30 minutes before drug treatment), evaluated by trypan blue dye exclusion.

Next, it was to be determined whether C6 treatment led PC3 cells to increase the production of reactive oxygen species (ROS). Two concentrations of C6 induced ROS production in a dose-dependent manner, and this effect was blocked when cells were pretreated with N-acetyl cysteine (NAC), a ROS scavenger (FIGS. 3A and 3B).

Figure 3D:
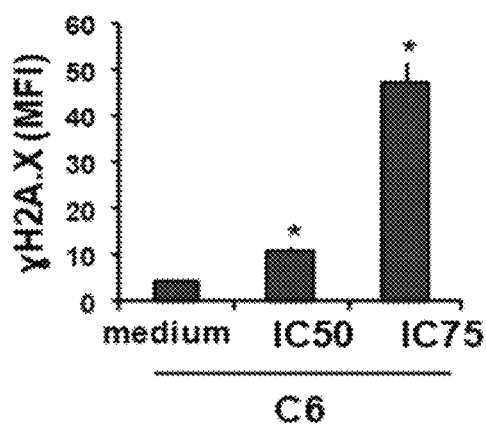
FIG. 3D is a graph showing histone H2A.X phosphorylation (YH2A.X) as a measure of double-stranded DNA breaks, detected with FITC anti-H2A.X Phospho (Ser139) antibody in terms of YH2A.X (MFI) levels after a 24 h treatment of PC3 cells with C6.
Figure 3E:
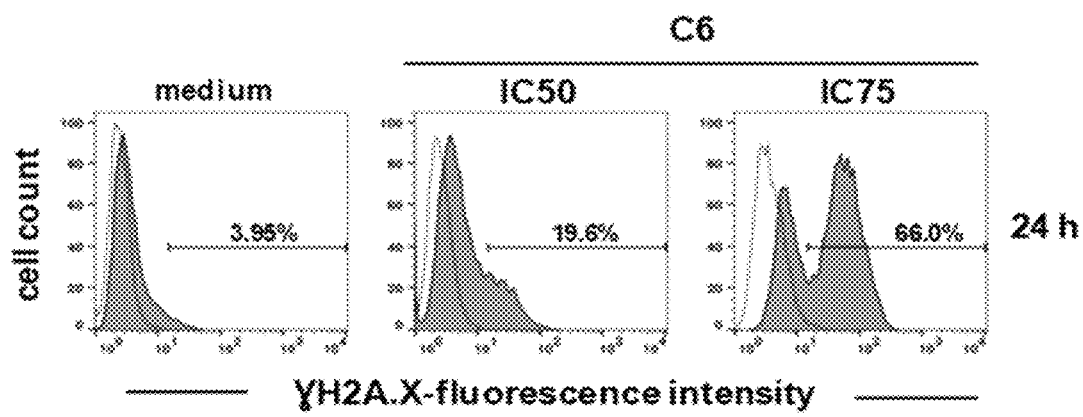
FIG. 3E is a representative flow cytometry histogram of YH2A.X of FIG. 3D.
Figure 3F:
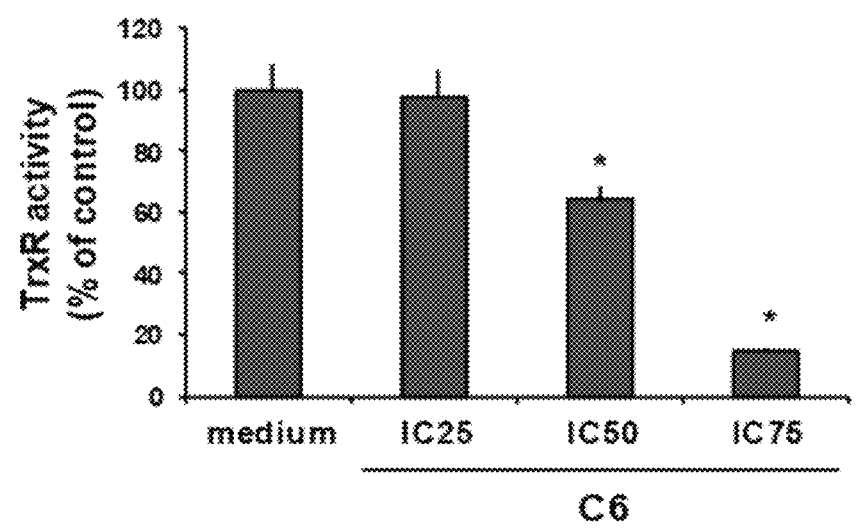
FIG. 3F is a graph illustrating thioredoxin reductase (TrxR) activity after a 12 h treatment with C6, normalized to control (medium)
Figure 3G:
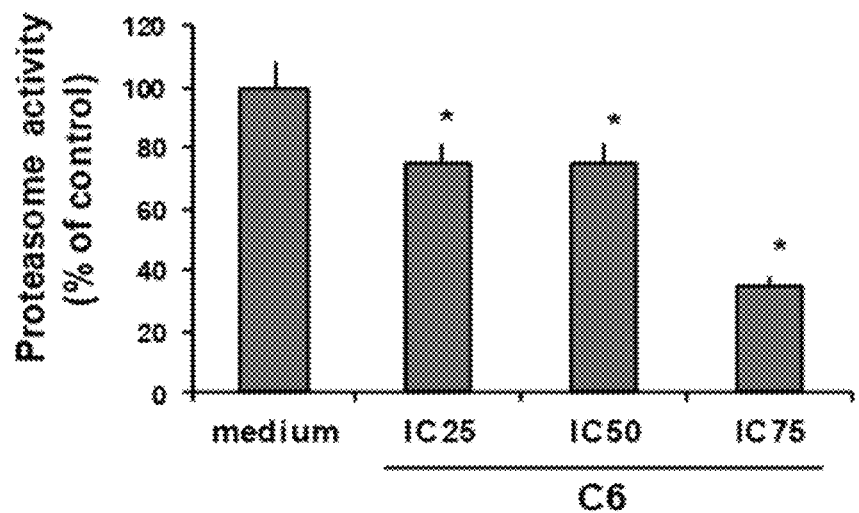
FIG. 3G is a graph illustrating proteasome activity after 12 h treatment with C6, evaluated with the 20S-Proteasome Assay kit, normalized to control (medium).

NAC decreased the cytotoxic effects of C6 (FIG. 3C), suggesting that ROS generation is involved in this compound's cytotoxicity. Treatment of PC3 cells with C6 also induced, in a dose-dependent manner, double-stranded DNA breaks, as shown by an increase in phosphorylation of histone H2A.X (FIGS. 3D and 3E). Because ROS elimination and the maintenance of intracellular redox balance depend on the thioredoxin (Trx) system, the effects of C6 used at $IC_{25}$ (0.31 μM), $IC_{50}$ (0.62 μM) and $IC_{75}$ (1.85 μM) on Trx reductase (TrxR) levels were examined and it was found that a short incubation resulted in a dose-dependent decrease of its enzymatic activity (FIG. 3F). See Scalcon V.; Bindoli A.; Rigobello M. P. Significance of the mitochondrial thioredoxin reductase in cancer cells: An update on role, targets and inhibitors. Free Radic Biol Med 2018. 127, 62-79. Finally, C6 exerted a dose-dependent inhibitory effect also on 20S proteasome activity (FIG. 3G). In FIGS. 3A-3G, all bar charts report means and SD of three independent experiments. Statistical analysis was performed using one-way ANOVA, followed by Turkey's on Dunnett's multiple comparisons test where appropriate. * P<0.05 vs medium unless otherwise indicated.

Effects of C6 on Tumor Cell Migration and Xenograft Growth

Figure 4A:
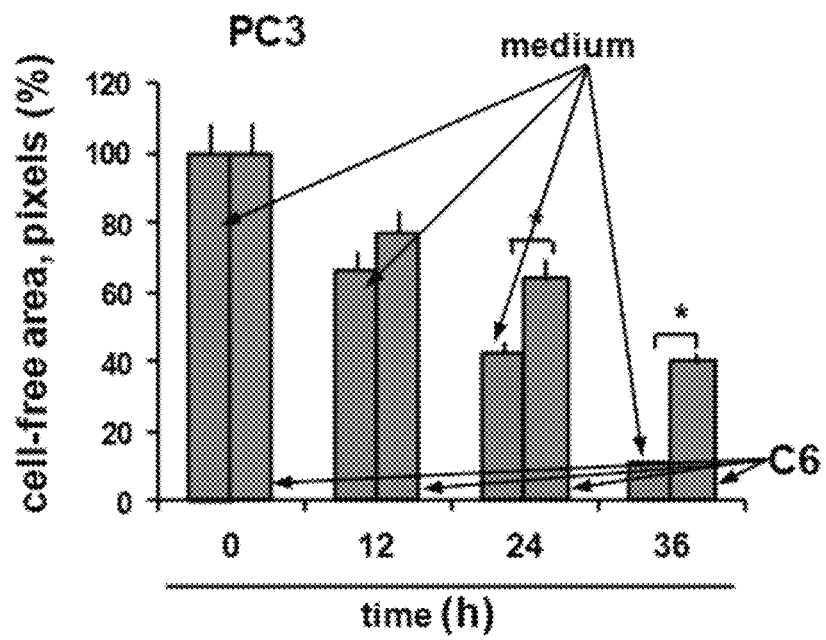
FIG. 4A is a graph illustrating results from a scratch assay where confluent monolayers of PC3 cells were treated or not with complex C6 (IC50) for 3 h in complete medium, "wounded" by scraping, then cultured in low serum medium and photographed every 12 h for up to 36 h, with the data expressed in terms of cell-free area remaining over time as cells migrated into the wound, normalized to time 0 (the mean and SD of three experiments each done in triplicate; * P<0.05, Student's t test), showing that the complex C6 reduces cell migration.
Figure 4B:
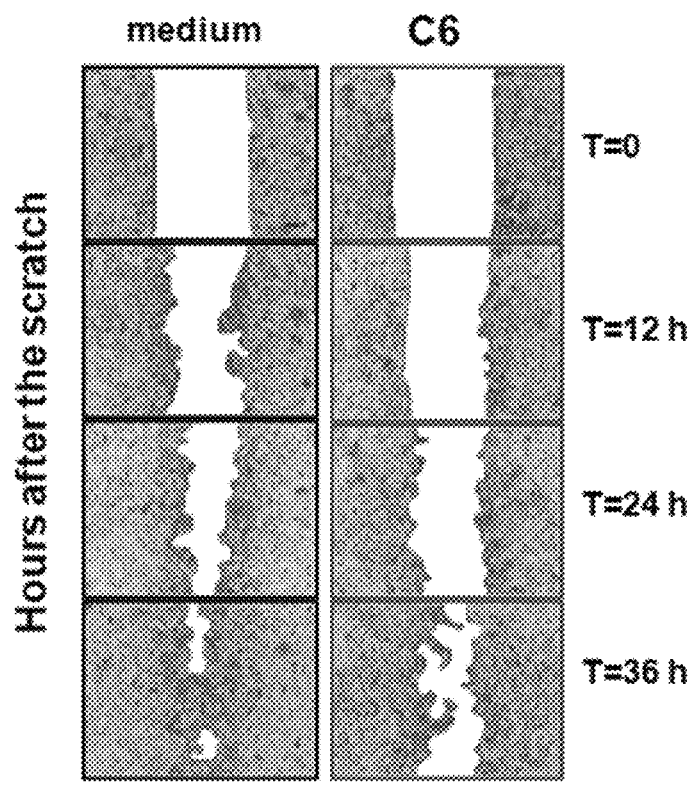
FIG. 4B shows representative phase contrast photomicrographs, original magnification 4×, from the scratch assay of FIG. 4A.
Figure 4C:
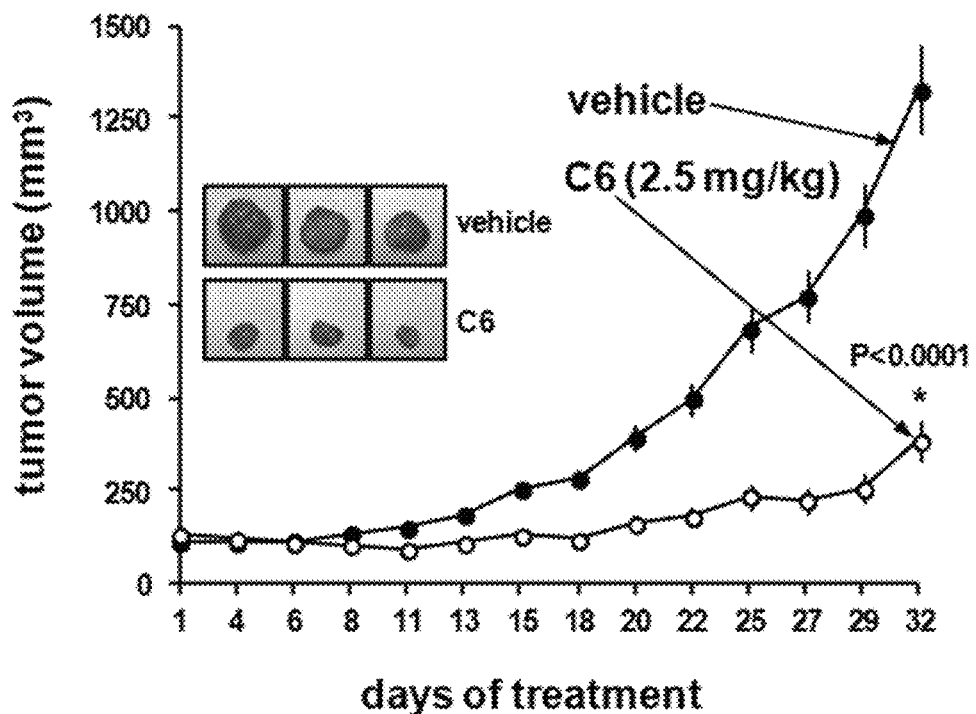
FIG. 4C is a graph showing growth of xenografts in nude mice inoculated with PC3 cells (3×106 cells/animal) and treated intratumorally with C6 (2.5 mg/kg) (n=5) or vehicle (n=5), values are expressed as mean and SD, Student's t test, *P<0.0001.
Figure 4D:
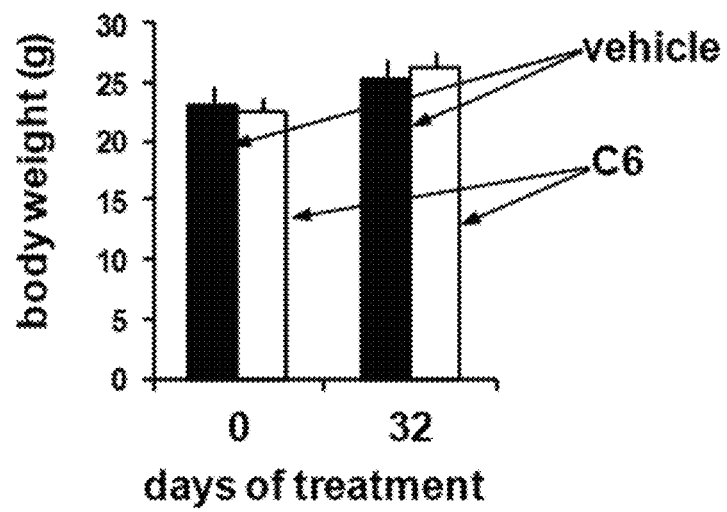
FIG. 4D is a graph of the body weights of xenografted mice (n=5 per group) from FIG. 4C.

The effect of C6 on PC3 cell migration was evaluated using the in vitro scratch assay. A 3 h pretreatment slowed the ability of PC3 cells to refill an empty area ("scratch") of the monolayer-compared to untreated cells: 36 h after the monolayer was scratched, the remaining uncovered area was about 40% in C6-pretreated cells, and about 10% in control cells (FIGS. 4A and 4B). Finally, the effects of C6 on the in vivo growth of PC3 cell xenografts in female athymic nude mice were examined. Inhibition of tumor growth became apparent starting 15 days after the beginning of treatment, compared to animals not treated with C6 (FIG. 4C). By day 32, control tumors had grown to a mean volume of 1327 mm$^3$ (SD=105 mm$^3$) whereas C6-treated tumors reached 385 mm$^3$ (SD=35 mm$^3$), reflecting a 71% inhibitory effect (FIG. 4C). This difference was significant (P<0.0001, Student's t test). C6 treatment did not affect the weight of the animals (FIG. 4D).

DISCUSSION

In this study, the anticancer activity of new bipyridine and bipyrimidine gold(III) complexes (C1-C8) using a panel of cancer cell lines was evaluated. The eight new complexes had potent cytotoxicity in ovarian, lung, breast, prostate, cervical and sarcoma cancer cell lines. They were also active in a cisplatin-resistant cervical cell line (R-ME-180) and in a cisplatin- and doxorubicin-resistant ovarian cancer cell line (A2780cis), indicating that they may overcome both cisplatin and doxorubicin resistance.

The mechanism of action and the in vivo activity of the most active compound, C6, were evaluated using androgen-resistant PC3 prostate cancer cells. C6 induced apoptosis, activated caspases 3,7 and modified the distribution of cells in cell cycle phases. Moreover, C6 increased ROS generation. ROS may play an important role in the cytotoxic effect of C6 since the ROS scavenger NAC counteracted C6's ability to inhibit cell growth. C6 treatment also induced double-stranded DNA breaks. This DNA damage may be due to the increased intracellular ROS levels or to a possible direct interaction of C6 with DNA. See Scalcon V.; Bindoli A.; Rigobello M. P. Significance of the mitochondrial thioredoxin reductase in cancer cells: An update on role, targets and inhibitors. Free Radic Biol Med 2018. 127, 62-79, incorporated herein by reference in its entirety.

Thioredoxin (Trx) and the seleno-enzyme thioredoxin reductase (TrxR) are essential components of the Trx system that regulates cellular redox signaling pathways. TrxR inhibition increases ROS accumulation, which causes mitochondrial dysfunction and apoptosis. See Scalcon V.; Bindoli A.; Rigobello M. P. Significance of the mitochondrial thioredoxin reductase in cancer cells: An update on role, targets and inhibitors. Free Radic Biol Med 2018. 127, 62-79; and Zhang J.; Li X.; Han X.; Liu R.; Fang J. Targeting the Thioredoxin System for Cancer Therapy. Trends Pharmacol Sci 2017. 38(9), 794-808, each incorporated herein by reference in their entirety. High levels of Trx and TrxR have been found in many different tumor types, including prostate cancer, and are associated with tumor progression and resistance to several anticancer drugs, including cisplatin. See Shan W.; Zhong W.; Zhao R.; Oberley T. D. Thioredoxin 1 as a subcellular biomarker of redox imbalance in human prostate cancer progression. Free Radic Biol Med 2010. 49, 2078-2087; and Yamada M.; Tomida A.; Yoshikawa H.; Taketani Y.; Tsuruo T. Increased expression of thioredoxin/adult T-cell leukemia-derived factor in cisplatin-resistant human cancer cell lines. Clin Cancer Res 1996. 2, 427-432, each incorporated herein by reference in their entirety. For these reasons, the Trx system may be a target for cancer therapy. See Scalcon V.; Bindoli A.; Rigobello M. P. Significance of the mitochondrial thioredoxin reductase in cancer cells: An update on role, targets and inhibitors. Free Radic Biol Med 2018. 127, 62-79; and Zhang J.; Li X.; Han X.; Liu R.; Fang J. Targeting the Thioredoxin System for Cancer Therapy. Trends Pharmacol Sci 2017. 38(9), 794-808. TrxR has already been identified as an important target of several gold(I) (e.g. auranofin) and gold(III) complexes. See Celegato M.; Borghese C.; Casagrande N.; Mongiat M.; Kahle X. U.; Paulitti A.; Spina M.; Colombatti A.; Aldinucci D. Preclinical activity of the repurposed drug Auranofin in classical Hodgkin lymphoma. Blood 2015. 126, 1394-1397; Marzano C.; Gandin V.; Folda A.; Scutari G.; Bindoli A.; Rigobello M. P. Inhibition of thioredoxin reductase by auranofin induces apoptosis in cisplatin-resistant human ovarian cancer cells. Free Radic Biol Med 2007. 42(6), 872-881; Saggioro D.; Rigobello M. P.; Paloschi L.; Folda A.; Moggach S. A.; Parsons S.; Ronconi L.; Fregona D.; Bindoli A. Gold(III)-dithiocarbamato complexes induce cancer cell death triggered by thioredoxin redox system inhibition and activation of ERK pathway. Chem Biol 2007. 14, 1128-1139; Cattaruzza L.; Fregona D.; Mongiat M.; Ronconi L.; Fassina A.; Colombatti A.; Aldinucci D. Antitumor activity of gold(III)-dithiocarbamato derivatives on prostate cancer cells and xenografts. Int J Cancer 2011. 128, 206-215; and Celegato M.; Fregona D.; Mongiat M.; Ronconi L.; Borghese C.; Canzonieri V.; Casagrande N.; Nardon C.; Colombatti A.; Aldinucci D. Preclinical activity of multiple-target gold(III)-dithiocarbamato peptidomimetics in prostate cancer cells and xenografts. Future Med Chem 2014. 6(11), 1249-1263, each incorporated herein by reference in their entirety. Here it was found that, consistently with increased ROS generation, C6 inhibited TrxR enzymatic activity in PC3 cells.

The proteasome, a central component of the protein degradation machinery, controls the expression of proteins linked to cell survival and proliferation. See Baumann K. Protein metabolism: How the proteasome adapts to stress. Nat Rev Mol Cell Biol 2014. 15(9), 562-563, incorporated herein by reference in its entirety. Cancer cells produce anti-apoptotic and pro-survival proteins and their treatment with proteasome inhibitors causes cell cycle arrest or apoptosis, suggesting their use in clinic. See Manasanch E. E.; Orlowski R. Z. Proteasome inhibitors in cancer therapy. Nat Rev Clin Oncol 2017. 14(7), 417-433, incorporated herein by reference in its entirety. Some gold(III) complexes have already been found to target the proteasome in cancer cells, and here it was found that C6 inhibited proteasome activity in prostate cancer cells. See Milacic V.; Chen D.; Ronconi L.; Landis-Piwowar K. R.; Fregona D.; Dou Q. P. A novel anticancer gold(III) dithiocarbamate compound inhibits the activity of a purified 20S proteasome and 26S proteasome in human breast cancer cell cultures and xenografts. Cancer Res 2006. 66, 10478-10486; Cattaruzza L.; Fregona D.; Mongiat M.; Ronconi L.; Fassina A.; Colombatti A.; Aldinucci D. Antitumor activity of gold(III)-dithiocarbamato derivatives on prostate cancer cells and xenografts. Int J Cancer 2011. 128, 206-215; Celegato M.; Fregona D.; Mongiat M.; Ronconi L.; Borghese C.; Canzonieri V.; Casagrande N.; Nardon C.; Colombatti A.; Aldinucci D. Preclinical activity of multiple-target gold(III)-dithiocarbamato peptidomimetics in prostate cancer cells and xenografts. Future Med Chem 2014. 6(11), 1249-1263; Tomasello M. F.; Nardon C.; Lanza V.; Di N. G.; Pettenuzzo N.; Salmaso S.; Milardi D.; Caliceti P.; Pappalardo G.; Fregona D. New comprehensive studies of a gold(III) Dithiocarbamate complex with proven anticancer properties: Aqueous dissolution with cyclodextrins, pharmacokinetics and upstream inhibition of the ubiquitin-proteasome pathway. Eur J Med Chem 2017, 138, 115-127; and Quero J.; Cabello S.; Fuertes T.; Marmol I.; Laplaza R.; Polo V.; Gimeno M. C.; Rodriguez-Yoldi M. J.; Cerrada E. Proteasome versus Thioredoxin Reductase Competition as Possible Biological Targets in Antitumor Mixed Thiolate-Dithiocarbamate Gold(III) Complexes. Inorg Chem 2018. 57(17), 10832-10845, each incorporated herein by reference in their entirety.

Since androgen-independent prostate cancer has high invasive potential, a successful therapeutic approach should counteract not only tumor growth but also the metastatic potential. See Ritch C.; Cookson M. Recent trends in the management of advanced prostate cancer. F1000Research, 2018, 7 (F1000 Faculty Rev): 1513, incorporated herein by reference in its entirety. Here, it was found that C6 reduced PC3 cell migration, suggesting that this gold(III) complex may inhibit not only tumor proliferation, but also its dissemination.

Some studies of metal-based compounds, including gold (III) complexes, have found promising in vitro cytotoxicity but did not test growth inhibition in in vivo experiments. See Nobili S.; Mini E.; Landini I.; Gabbiani C.; Casini A.; Messori L. Gold compounds as anticancer agents: chemistry, cellular pharmacology, and preclinical studies. Med Res Rev 2010. 30, 550-580; and Micale N.; Schirmeister T.; Ettari R.; Cinellu M. A.; Maiore L.; Serratrice M.; Gabbiani C.; Massai L.; Messori L. Selected cytotoxic gold compounds cause significant inhibition of 20S proteasome catalytic activities. J Inorg Biochem 2014. 141, 79-82, each incorporated herein by reference in their entirety. Therefore, the in vivo antitumor activity of C6 was also evaluated. Consistent with the in vitro studies, C6 significantly reduced PC3 tumor xenograft growth with low toxicity (measured as body weight change). These results are promising for preclinical and clinical testing.

Materials and Methods

Methods for the synthesis and chemical characterization of the gold(III) complexes are described in the Supplementary Materials and Methods section presented below, together with electrochemical methods for testing their interactions with a protein, an amino acid, and a nucleobase and cellular methods for testing uptake.

Drugs

Gold(III) complexes were dissolved in DMSO to 10 μM. The same amount of DMSO necessary to dissolve the complexes was used as negative control in all experiments. Cisplatin and doxorubicin were surplus drugs obtained from the pharmacy at Centro Riferimento Oncologico.

Cell Lines and Culture Conditions

Human androgen-resistant (PC3) and androgen-sensitive (DU145) prostate cancer cell lines were obtained from the German Collection of Microorganisms and Cell Cultures (DSMZ, Braunschweig, Germany). Human breast adenocarcinoma MCF-7 (HTB-22TM), lung cancer (A549), and osteosarcoma (MG-63) cell lines were from the American Type Culture Collection (ATCC, Rockville, USA). Human ovarian epithelial carcinoma-derived A2780 cell line and its cisplatin- and doxorubicin-resistant clone A2780cis were from Sigma-Aldrich. The highly invasive cervical cancer-derived ME-180 (HPV positive) cell line was a kind gift of Dr. G. Toffoli (CRO, Aviano), and the cisplatin-resistant clone R-ME-180 was developed in our laboratory by continuous exposure to 1 μM cisplatin. Cell lines were tested for mycoplasma every 15 days using the MycoAlert test (Lonza).

A549, MG-63, MCF-7, ME-180 and R-ME-180 cells were cultured in DMEM, and A2780, A2780cis, PC3 and DU145 cells were cultured in RPMI-1640 medium; media contained 10% heat-inactivated fetal bovine serum (FBS), 1% (v/v) of penicillin (10,000 units/mL)-streptomycin (10 mg/mL) and 1% (v/v) L-glutamine (200 mM) (all from Sigma-Aldrich). R-ME-180 and A2780cis cells were maintained in 1 μM cisplatin. Adipose-derived stromal cells were maintained in MSCGM BulletKit medium (Lonza). All cell lines were cultured at 37° C. in a 5% $CO_2$, fully humidified atmosphere Cytotoxicity Assay Cell lines were seeded in 96-well flat-bottomed microplates in 100 μL culture medium at the following densities: DU145, PC3 and MCF-7 cells ($2.5 \times 10^3$ cells/well); A2780, A2780cis, ME-180, R-ME-180 and A549 cells ($4.0 \times 10^3$ cells/well); and MG-63 cells ($2.0 \times 10^3$ cells/well). Cells were allowed to adhere for 24 h. Then the medium was replaced with fresh medium alone or with one of the gold(III) complexes at increasing concentrations from 0 to 100 μM. The reference drugs cisplatin (0-100 μM) and doxorubicin (0-1 μM) were included as positive controls for growth inhibition. After 72 h, cell viability was assayed using the MTT assay. All experimental conditions were tested in triplicate and the experiment was done three times.

Half maximal inhibitory concentrations ($IC_{50}$, the concentration required for 50% in vitro inhibition of growth) and $IC_{25}$ and $IC_{75}$ values were calculated for each experiment using CalcuSyn software (Biosoft, Ferguson, MO, USA). See Chou T. C.; Talalay P. Quantitative analysis of dose-effect relationships: the combined effects of multiple drugs or enzyme inhibitors. Adv Enzyme Regul 1984. 22, 27-55, incorporated herein by reference in its entirety. $IC_{50}$ values were reported as mean (SD). For drug-resistance cell lines, fold resistance (FR) was calculated as the ratio of the $IC_{50}$ of the resistant cell line to the $IC_{50}$ of the parental cell line.

Cellular Assays

In all cellular assays, PC3 cells ($2.0 \times 10^5$ cells/well in six-well plates) were incubated in complete culture medium containing different concentrations of complex C6 ($IC_{25}$=0.31 μM, $IC_{50}$=0.62 μM, $IC_{75}$=1.85 μM). All experimental conditions were tested in triplicate and experiments were done three times to calculate means and SD.

For apoptosis assays, PC3 cells were treated with C6 for 24 h and then apoptosis was assayed by staining for 15 min with FITC Annexin V reagent (BD Pharmingen) and propidium iodide (PI). Apoptotic cells were detected by flow cytometry (BD FACSCanto II flow cytometer) and analyzed using BD FACSDiva v8.0.1 software (BD Biosciences). Caspase 3,7 activation was evaluated using fluorochrome-labeled inhibitors of caspases (FLICA) of the CaspaTag Caspase 3,7 In Situ Assay Kit, Fluorescein (Millipore) and evaluated by flow cytometry; data were expressed as mean fluorescence intensity.

To assay the distribution of cells in the various phases of the cell cycle, PC3 cells were treated with C6 for 48 h, then harvested, fixed in cold 70% ethanol for 15 min and stained with PI solution (50 μg/mL PI, 0.1% NP-40, 100 μg/mL PureLink RNase A, 0.1% sodium citrate). After 1 h, cells were analyzed by flow cytometry. The distribution of cells in different cell cycle phases was quantified using ModFit LT 4.0 software.

The production of reactive oxygen species (ROS) was evaluated using 2',7'-dichlorodihydrofluorescein diacetate (H2DCFDA) (H2-DCF, DCF) (Invitrogen). Cells were pretreated with the antioxidant N-acetyl-L-cysteine (NAC; 5 mM) (Sigma) for 30 min before C6 was added. After 24 h of C6 treatment, cells were harvested and viable cells were counted by trypan blue dye exclusion. Then cells were washed, stained with 1 μM H2DCFDA for 30 min at 37° C., and finally ROS production was analyzed by flow cytometry.

The presence of double-stranded DNA breaks was assessed 24 h after treatment with C6 by fixing and permeabilizing cells with Fix & Perm medium A and B (Invitrogen) and staining with FITC anti-H2A.X Phospho (Ser139) Antibody (BioLegend, San Diego, USA). Stained cells were evaluated by flow cytometry.

Thioredoxin reductase (TrxR) (EC 1.8.1.9) was assayed using the Thioredoxin Reductase Assay Kit (Sigma-Aldrich). Cells were treated with C6 for 12 h and then lysed in 50 mM Tris-HCl pH 7.6, 0.1% Triton X-100, 0.9% NaCl. Enzyme activity was determined reading absorbance at 412 nm using a spectrophotometer (Biomate 3 Thermo Spectronic). The enzymatic activity was normalized to the protein concentration, determined using the Bio-Rad protein assay (Protein Assay Dye Reagent Concentrate, Bio-Rad Laboratories), and expressed as percentage of control (no C6).

Proteasome activity (EC 3.4.25.1) was evaluated on the same cell lysates as used to assay TrxR. Proteasome activity was assayed in cytosolic extracts using the 20S Proteasome Activity Assay kit APT280 (Merck Millipore) and a computer-interfaced GeniusPlus microplate reader (Tecan). The activity was normalized to the protein concentration, determined using the Bio-Rad protein assay, as expressed as percentage of control.

Cell migration was assessed using the in vitro scratch assay. Briefly, cells were grown to confluence and then treated with C6 ($IC_{50}$). After 3 h, monolayers were washed twice with PBS, scraped with a pipette tip to create a "wound" in the monolayer, and washed again. Culture medium with 2% (not 10%) FBS was added and the cells were cultured for 36 h. Wounds were photographed every 12 h using an inverted microscope (EclipseTS/100, Nikon) at magnification 4×. Migration was assessed by measuring the cell-free area (in pixels) with ImageJ tool software after 12, 24 and 36 h.

Human Prostate Tumor Xenograft Experiments

Animal experiments were approved by the Italian Ministry of Health (no. 671/2015/PR). Ten 4-week-old female athymic nu/nu (nude) mice were purchased from Envigo. PC3 cells ($3\times10^6$ in a 0.1 mL solution of Matrigel 1:3 in PBS) were inoculated subcutaneously into the right flank of each mouse. Body weight and tumors were measured three times a week, and tumor volumes were calculated according to the formula: (width$^2$×length×3.14)/6. When tumors reached a volume of ca. 120 mm$^3$, mice were divided into two groups of five animals each. Mice were treated every other day with an intratumoral injection of 2.5 mg/kg C6 or an equal volume of vehicle (10% DMSO, 20% Cremophor Sigma-Aldrich, 70% PBS). Mice were killed on day 32 when control tumors had reached about 1300 mm$^3$.

Statistical Analysis

Statistical analysis was performed using GraphPad Prism v6 software. Student's t test was used to compare two groups, and one-way analysis of variance (ANOVA) was used for three or more groups; consecutive multiple comparisons were performed using Dunnett's or Tukey's test. P<0.05 indicated statistical significance.

Supplementary Materials and Methods

Materials and methods used in the synthesis and chemical characterization of gold(III) complexes (C1-C8), and electrochemical methods and methods for cellular uptake assays are presented below. Additionally, results are presented on the yield and purity of gold(III) complexes, electrochemical data on the interactions of gold(III) complexes with lysozyme (Table 4 and FIGS. 5A-5D, FIGS. 6A-6D, FIGS. 7A-7D, FIGS. 8A-8D), tryptophan (Table 5 and FIGS. 9A-9D, FIGS. 10A-10D, FIGS. 11A-11D, FIGS. 12A-12D) and guanine (Table 6 and FIGS. 13A-13F and FIGS. 14A-14F), and cellular data on the uptake of selected gold(III) complexes by PC3 cells (FIG. 15) and on the inhibition of growth by C6 in PC3 prostate cancer cells and adipose-derived stromal cells (FIG. 16).

Reagents

Sodium tetrachloroaurate(III) dihydrate, sodium dimethyldithiocarbamate hydrate, sodium diethyldithiocarbamate trihydrate, sodium dibenzyldithiocarbamate hydrate, 2,2'-bipyrimidine, 2,2'-bipyridine-3,3'-diol, disodium hydrogen phosphate, sodium dihydrogen phosphate, tryptophan, lysozyme, 98% guanine, and 99.8% ethanol were obtained from Sigma-Aldrich. Anhydrous 99.8% dichloromethane were purchased from Merck and used without further purification. Double distilled water used only for electrochemical measurements was from an Aquatron A4000D water still (Stuart). All reactions were carried out at ambient room temperature.

Synthesis of Gold(III) Complexes (C1-C8)

[Au(BPYH)(Cl)$_2$]Cl (C1) was synthesized by combining 0.5 mM Na[AuCl$_4$]·2H$_2$O (200 mg in 3 mL H$_2$O) and 0.5 mM 2 2'-bipyridine-3 3'-diol (94 mg in 15 mL of ethanol:dichloromethane (3:1)) and stirred for 3 h. The solution was filtered and kept in an undisturbed area for 3 days. Black cubic crystals appeared. The black precipitate was collected by filtration, washed with distilled water (3×10 mL) and dried under vacuum.

[Au(BPYH)(DMDTC)]Cl$_2$ (C2) was synthesized stepwise. First, 0.5 mM Na[AuCl$_4$]·2H$_2$O (200 mg in 3 mL distilled water) and 0.5 mM 2 2'-bipyridine-3 3'-diol (94.0 mg in 15 mL ethanol:dichloromethane (3:1)) were added simultaneously to 20 mL of 99.8% ethanol, and the mixture was stirred for 3 h, generating a pale yellow, turbid solution. Second, 0.5 mM sodium dimethyldithiocarbamate hydrate (71.6 mg in 10 mL distilled water) was added dropwise and the mixture was stirred for an additional 1 h. The product light-yellow precipitate was collected by filtration, washed with distilled water (3×10 mL), and dried under vacuum.

[Au(BPYH)(DEDTC)]Cl$_2$ (C3) was synthesized stepwise. First, 0.5 mM Na[AuCl$_4$]·2H$_2$O (200 mg in 3 mL H$_2$O) and 0.5 mM 2 2'-bipyridine-3 3'-diol (94.0 mg in 15 mL ethanol:dichloromethane (3:1)) were added simultaneously to 20 mL of 99.8% ethanol, and the mixture was stirred for 3 h, generating a yellow turbid solution. Second, 0.5 mM sodium diethyldithiocarbamate trihydrate (112.6 mg in 10 mL distilled water) was added dropwise and the mixture was stirred for an additional 1 h. The obtained yellow precipitate was collected by filtration, washed with distilled water (3×10 mL) and dried under vacuum. The final product was a yellow crystalline powder.

[Au(BPYH)(DBDTC)]Cl$_2$ (C4) was synthesized stepwise. First, 0.5 mM 2 2'-bipyridine-3 3'-diol (94.0 mg in 15 mL ethanol:dichloromethane (3:1)) was combined with 0.5 mM Na[AuCl$_4$]·2H$_2$O (200 mg in 3 mL distilled water) and the mixture was stirred for 3 h, generating a yellow turbid solution. Second, 0.5 mM sodium dibenzyldithiocarbamate hydrate (148 mg in 10 mL 99.8% ethanol) was added dropwise and the mixture was stirred for an additional 1 h. The orange precipitate was collected by filtration, washed with distilled water (3×10 mL) and dried under vacuum. The final product was an orange crystalline powder.

[Au$_2$(BPM)(Cl)$_4$]Cl$_2$ (C5) was synthesized by combining 0.5 mM 2 2'-bipyrimidine (79 mg in 20 mL 99.8% ethanol) and 1.0 mM Na[AuCl$_4$]·2H$_2$O (397.8 mg in 10 mL distilled water). The mixture was stirred for 3 h. The yellow precipitate was collected by filtration, washed with distilled water (3×10 mL), and dried under vacuum.

[Au$_2$(BPM)(DMDTC)$_2$]Cl$_4$ (C6) was synthesized stepwise. First, 0.5 mM 2 2'-bipyrimidine (79 mg in 20 mL 99.8% ethanol) was combined with 1.0 mM Na[AuCl$_4$]·2H$_2$O (397.8 mg in 3 mL distilled water). The mixture was stirred for 3 h, generating a bright yellow, turbid solution. Then, 1.0 mM sodium dimethyldithiocarbamate hydrate (143.2 mg in 20 ml distilled water) was slowly added, and the reaction mixture was stirred for 1 h. The product appeared as a pale yellow precipitate. The precipitate was collected by filtration, washed with distilled water (3×10 mL) and dried under vacuum.

[Au$_2$(BPM)(DEDTC)$_2$]Cl$_4$ (C7) was synthesized stepwise. First, 0.5 mM 2,2'-bipyrimidine (79 mg in 20 mL 99.8% ethanol) was combined with 1.0 mM Na[AuCl$_4$]·2H$_2$O (397.8 mg in 3.0 mL distilled water). The mixture was stirred for 3 h, generating a bright yellow, turbid solution. Then, 1.0 mM sodium diethyldithiocarbamate hydrate (226 mg in 20 mL distilled water) was slowly added, and the reaction mixture was stirred for 1 h. The product appeared as a dark yellow precipitate; it was collected by filtration, washed with distilled water (3×10 mL), and dried under vacuum for 72 hours.

[Au$_2$(BPM)(DBDTC)$_2$]Cl$_4$ (C8) was synthesized stepwise. First, 0.5 mM 2 2'-bipyrimidine (79 mg in 20 mL 99.8% ethanol) was combined with 1.0 mM Na[AuCl$_4$]·2H$_2$O (397.8 mg in 3 mL distilled water). The mixture was stirred for 3 h, generating a yellow, turbid solution. Then, 1.0 mM sodium dibenzyldithiocarbamate hydrate (295.4 mg in 20 mL distilled water) was slowly added, and the reaction mixture was stirred for 1 h. The product appeared as a yellowish green precipitate; it was collected by filtration, washed with distilled water (3×10 mL), and dried under vacuum for 72 hours.

Chemical Characterization of Gold(III) Complexes

Due to the poor solubility of the gold(III) complexes in water, they were dissolved in 99.8% ethanol. The pH of buffers was monitored on a Accumet XL50 pH meter. A GR-2000 electrical balance was used to weigh the various chemicals. Electrochemical measurements for cyclic voltammetry and square wave voltammetry were performed using Autolab instruments (Metrohm; Netherlands). The electrochemical workstation had three electrodes (from CH Instruments): a glassy carbon electrode (GCE) as the working electrode, platinum as the counter electrode, and Ag/AgCl as the reference electrode (in saturated KCl). The GCE was polished as a mirror-like surface with alumina slurry on a synthetic cloth before every electrochemical analysis. Square wave voltammetry and cyclic voltammetry were scanned from 0 to 1.3 V for the various analyses. Elemental analyses of gold(III) complexes (C1-C8) were performed on PerkinElmer Series 11 (CHNS/O), Analyzer 2400.

The solid state FTIR spectra of sodium dimethyldithiocarbamate hydrate, sodium diethyldithiocarbamate trihydrate, and sodium dibenzyldithiocarbamate hydrate (free ligands) and their corresponding gold(III) complexes were recorded on a PerkinElmer FTIR 180 spectrophotometer or NICOLET 6700 FTIR using potassium bromide (KBr) pellets over the range 4000-400 $cm^{-1}$. $^1H$ and $^{13}C$ NMR spectra were recorded on a LAMBDA 500 spectrophotometer operating at 500.01 and 125.65 MHz respectively, corresponding to a magnetic field of 11.74 T. Tetramethylsilane was used as an internal standard for $^1H$ and $^{13}C$. The $^{13}C$ NMR spectra were obtained with $^1H$ broadband decoupling, and the spectral conditions were: 32 k data points, 0.967 s acquisition time, 1.00 s pulse delay and 45 g° pulse angle.

Gold(III) Complex Interactions with Lysozyme, Tryptophan and Guanine

The electrochemical investigation of the interactions between the gold(III) complexes (C1-C8) and lysozyme, tryptophan and guanine was performed using the Autolab instrument described above, with a three-electrode system (CH Instruments): platinum wire counter electrode (CHI115), Ag/AgCl reference electrode (in 3 M KCl, CHI111) and glassy carbon working electrode (CHI112) inserted into a 5.0 ml glass cell. Solutions of 1 mM lysozyme, 5 mM tryptophan and 5 mM guanine were prepared in double distilled water, and the experiment was performed in 0.1 M phosphate buffer at pH 6.8.

Cellular Uptake of Gold(III) Complexes

PC3 cells ($1 \times 10^6$ cells seeded in 100×20 culture dishes) were treated for 2 h in duplicate with 3 μM C4, C5, C6 or C7 in complete culture medium. After treatment, monolayers were washed with ice-cold PBS four times, and the cells were detached with trypsin-EDTA and washed three times with ice-cold PBS by centrifugation. The cell pellet was solubilized in 700 μL of $HNO_3$—HCl solution (1:3 molar ratio) for 2 h at 100° C., and then diluted with 4 mL water. Samples were analyzed for gold on an Agilent 7500 inductively coupled plasma mass spectrometer (ICP-MS). Results were expressed as ng gold/$10^6$ cells. The experiment was performed a total of two times and the results were expressed as mean and SD.

Growth Inhibition Curves for C6 in Adipose-Derived Stromal Cells

Human adipose-derived stromal cells (ADSCs) were from Lonza (Verviers, Belgium). ADSCs were maintained in MSGM bullet kit (Lonza) and experiments were performed in DMEM (Cambrex Bio Science, Milan, Italy) supplemented with 10% FBS. To evaluate effects of C6, ADSCs were seeded in 96-well flat-bottomed microplates ($5.0 \times 10^3$ cells in 100 μL per well) and incubated for 24 h (to allow cell adhesion) before drug testing. The medium was removed and replaced with fresh medium containing C6 at increasing concentrations (from 0.1 to 1 μM). Cells were incubated at 37° ° C. for 72 h. Each treatment was performed in triplicate. Cell growth was measured using the MTT assay.

Supplementary Results

Analytical Data of Gold(III) Complexes

[Au(BPYH)(Cl)$_2$]Cl (C1). Yield: 83.09% (219.98 mg). FT-IR (KBr, $\upsilon_{max}$, $cm^{-1}$): 3470 (b), 3071 (w), 1647 (m), 1584 (s), 1459 (s), 1269 (m), 1134 (s), 1012 (m), 916 (w), 790 (s), 565 (m), 508 (m). $^1H$ NMR (500 MHz, DMSO-d$_6$): δ=7.57, 8.25 and 8.77 (3H, 2×CH, BPYH). $^{13}C$ NMR (125.65 MHz, DMSO-d$_6$): δ=125.81, 128.31, 136.68, 138.63 and 155.31 (BPYH). Anal. calc. for $C_{10}H_7Cl_2N_2O_2Au$ (456); C, 26.38; H, 1.55; N, 6.16; Found: C, 26.42; H, 1.53; N, 6.18%.

[Au(BPYH)(DMDTC)]Cl$_2$ (C2). Yield: 83.09% (219.98 mg). FT-IR (KBr, $\upsilon_{max}$, $cm^{-1}$): 3437 (b), 3055 (w), 2921 (w); 1576 (s), 1484 (s), 1299 (m), 1111 (w), 1060 (m), 989 (w), 795 (s), 580 (m). $^1H$ NMR (500 MHz, DMSO-d$_6$): δ=2.49 (6H, 2×CH$_3$), 7.51, 8.18 and 8.63 (2H, 2×CH, BPYH). $^{13}C$ NMR (125.65 MHz, DMSO-d$_6$): δ=39.38 (CH$_3$), 126.20, 128.30, 135.49, 138.74 and 155.33 (2,2'-BPYH), 193.84 (NC=S). Anal. calc. for $C_{13}H_{13}Cl_1N_3O_2S_2Au$ (539.81): C, 28.92; H, 2.43; N, 7.79; S, 11.88%. Found: C, 28.97; H, 2.39; N, 7.81; S, 11.91%.

[Au(BPYH)(DEDTC)]Cl$_2$ (C3). Yield: 86.87% (166.87 mg). FT-IR (KBr, $\upsilon_{max}$, $cm^{-1}$): 3443 (b), 3047 (w), 2928 (w), 1572 (s), 1490 (s), 1235 (m), 1155 (w), 1063 (m), 876 (m), 796 (s), 548 (m). $^1H$ NMR (500 MHz, DMSO-d$_6$): δ=2.49 (6H, 2×CH$_3$), 3.75 (4H, 2×CH$_2$), 7.49, 8.18 and 8.62 (2H, 2×CH, BPYH). $^{13}C$ NMR (125.65 MHz, DMSO-d$_6$): δ=12.11 (CH$_3$), 46.52 (CH$_2$), 125.78, 128.21, 136.74, 138.79 and 155.33 (2,2'-BPYH), 195.11 (NC=S). Anal. calc. for $C_{15}H_{17}Cl_1N_3O_2S_2Au$ (567.86): C, 31.73; H, 3.02; N, 7.40; S, 11.29%. Found: C, 31.76; H, 2.99; N, 7.43; S, 11.31%.

[Au(BPYH)(DBDTC)]Cl$_2$ (C4). Yield: 85.55% (226.13 mg). FT-IR (KBr, $\upsilon_{max}$, $cm^{-1}$): 3444 (b), 3021 (w), 2925 (w); 1532 (s), 1434 (s), 1223 (s), 1117 (m), 1068 (m), 982 (m), 796 (s), 549 (m). $^1H$ NMR (500 MHz, DMSO-d$_6$): δ=5.78 (4H, 2×CH$_2$), 8.10 (10H, 2×C$_6$H$_5$), 8.18, 8.27 and 8.93 (2H, 2×CH, BPYH). $^{13}C$ NMR (125.65 MHz, DMSO-d$_6$): δ=55.01 (CH$_2$), 125.67, 128.93, 138.78 and 155.35 (BPYH), 128.21-132.49 (C$_6$H$_5$), 199.10 (NC=S). Anal. calc. for $C_{25}H_{21}Cl_1N_3O_2S_2Au$ (692.00): C, 43.39; H, 3.06; N, 6.07; S, 9.27%. Found: C, 43.41; H, 3.05; N, 6.09; S, 9.31%.

[Au$_2$(BPM)(Cl)$_4$]Cl$_2$ (C5). Yield: 80.09% (187.27 mg). FT-IR (KBr, $\upsilon_{max}$, $cm^{-1}$): 3073 (m), 1577 (s), 1406 (s), 1226 (m), 1113 (m), 1023 (m), 821 (m), 570 (m). $^1H$ NMR (500 MHz, DMSO-d$_6$): δ=7.35 and 8.72 (4H, 4×CH and 2H, 2×CH, BPM). $^{13}C$ NMR (125.65 MHz, DMSO-d$_6$): δ=121.99, 157.89 and 161.84 (BPM). Anal. calc. for $C_8H_6Cl_6N_4Au_2$ (764.81): C, 12.56; H, 0.79; N, 7.33%. Found: C, 12.59; H, 0.78; N, 7.35%.

[Au$_2$(BPM)(DMDTC)$_2$]Cl$_4$ (C6). Yield: 80.09% (187.27 mg). FT-IR (KBr, $\upsilon_{max}$, $cm^{-1}$): 3057 (w), 2925 (w), 1578 (s), 1402 (s), 1238 (m), 1163 (m), 1046 (m), 967 (w), 876 (w), 559 (m). $^1H$ NMR (500 MHz, DMSO-d$_6$): δ=2.35 (6H, 2×CH$_3$), 7.35 and 8.70 (4H, 4×CH and 2H, 2×CH, BPM). $^{13}C$ NMR (125.65 MHz, DMSO-d$_6$): δ=40.29 (CH$_3$), 121.28, 135.33, 140.27 and 147.80 (2,2'-BPM), 193.87

(NC=S). Anal. calc. for $C_{14}H_{18}Cl_4N_6S_4Au_2$ (934.34): C, 18.00; H, 1.94; N, 8.99; S, 13.73%. Found: C, 18.05; H, 1.91; N, 9.03; S, 13.77%.

[Au$_2$(BPM)(DEDTC)$_2$]Cl$_4$ (C$_7$). Yield: 88.51% (343.9 mg). FT-IR (KBr, $\upsilon_{max}$, cm$^{-1}$): 3055 (w), 2978 (w), 2930 (w), 1552 (s), 1463 (s), 1351 (m), 1286 (s), 1195 (m), 1089 (m), 994 (m), 846 (m), 584 (m). $^1$H NMR (500 MHz, DMSO-d$_6$): δ=2.43 (6H, 2×CH$_3$), 3.85 (4H, 2×CH$_2$), δ=7.33 and 8.71 (4H, 4×CH and 2H, 2×CH, BPM). $^{13}$C NMR (125.65 MHz, DMSO-d$_6$): δ=12.13 (CH$_3$), 46.58 (CH$_2$), 120.55, 156.63 and 161.75 (BPM), 193.89 (NC=S). Anal. calc. for $C_{18}H_{26}Cl_4N_6S_4Au_2$ (990.44): C, 21.83; H, 2.65; N, 8.49; S, 12.95%. Found: C, 21.88; H, 2.61; N, 8.55; S, 13.07%.

[Au$_2$(BPM)(DBDTC)$_2$]Cl$_4$ (C$_8$). Yield: 78.01% (256.6 mg). FT-IR (KBr, $\upsilon_{max}$, cm$^{-1}$): 3051 (w), 2972 (w), 2922 (m), 1573 (s), 1471 (s), 1355 (m), 1234 (s), 1133 (m), 1047 (m), 980 (s), 553 (m). $^1$H NMR (500 MHz, DMSO-d$_6$): δ=5.02 (4H, 2×CH$_2$), 7.37 (10H, 2×C$_6$H$_5$), 7.33 and 8.75 (4H, 4×CH and 2H, 2×CH, BPM). $^{13}$C NMR (125.65 MHz, DMSO-d$_6$): δ=55.37 (CH$_2$), 120.81, 156.23 and 161.90 (BPM), 128.17-132.50 (C$_6$H$_5$), 199.14 (NC=S). Anal. calc. for $C_{38}H_{34}Cl_4N_6S_4Au_2$ (1238.72): C, 36.85; H, 2.77; N, 6.78; S, 10.35%. Found: C, 36.88; H, 2.73; N, 6.80; S, 10.37%.

Figure 5A:
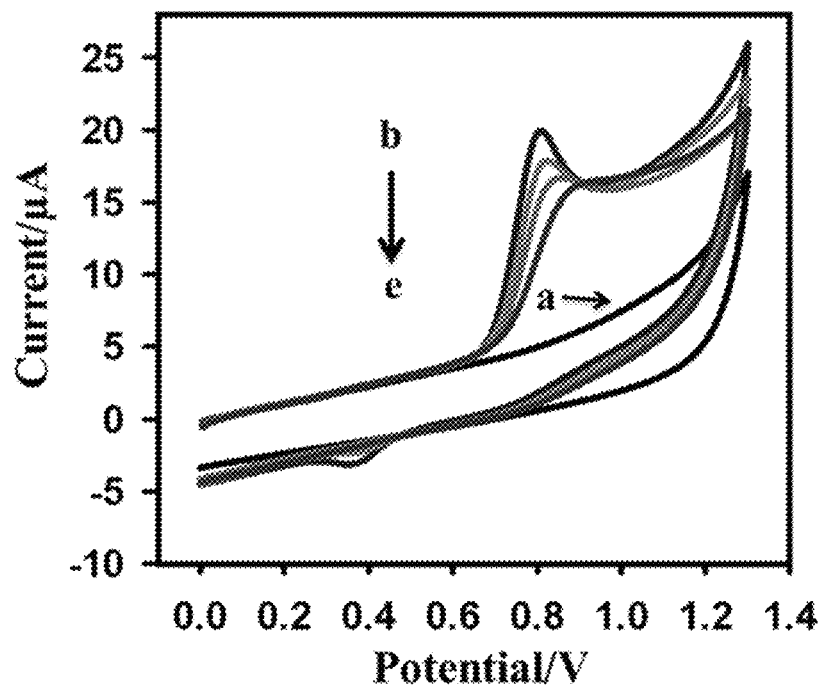
FIGS. 5A-5D are voltammograms for the interaction of complex C1 with lysozyme in 0.1 M phosphate buffer (pH 6.8) or in control experiments (C1 in double-distilled water)
Figure 5B:
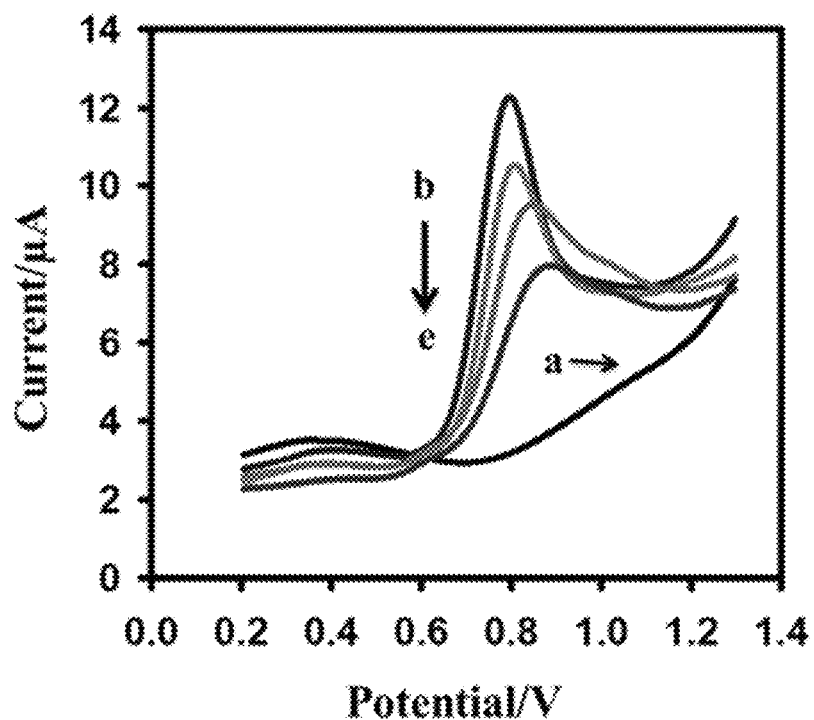
Figure 5C:
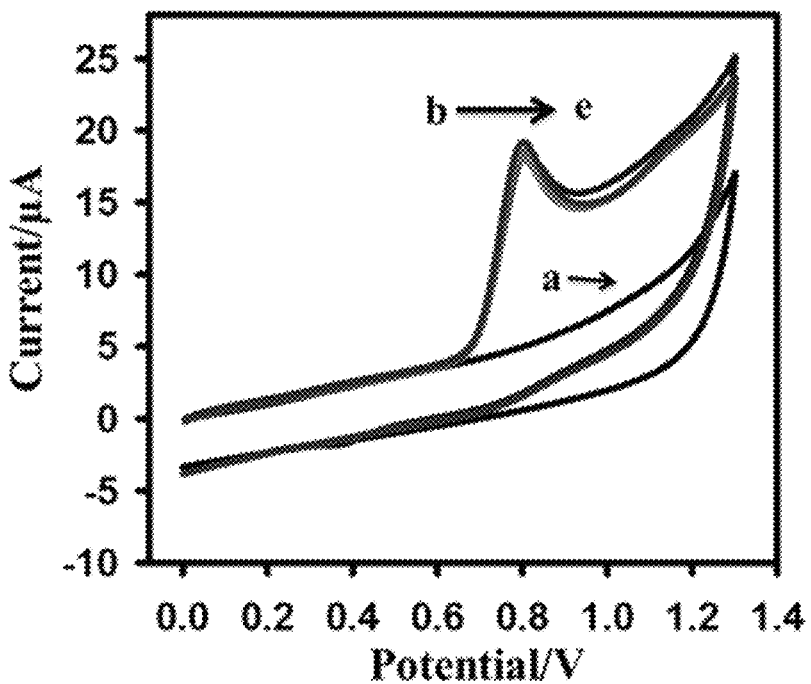
Figure 5D:
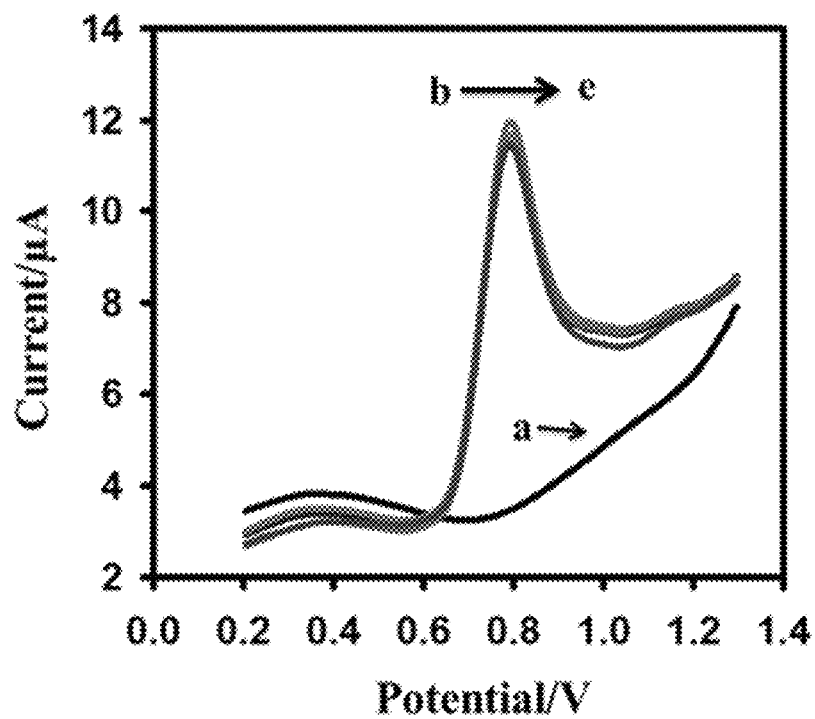

FIG. 5A shows cyclic voltammetry of 100 µM C$_1$ with varying concentrations of lysozyme: (a) buffer blank; (b) C1 alone; (c) C1 and 1 µM lysozyme; (d) C1 and 4 µM lysozyme; and (e) C1 and 10 µM lysozyme, FIG. 5B shows square-wave voltammetry of 100 µM C1 with various concentrations of lysozyme as in FIG. 5A, FIG. 5C shows cyclic voltammetry of 100 µM C$_1$ in control experiments with varying volumes of double-distilled water: (a) buffer blank; (b) 0 µL; (c) 3 µL; (d) 12 µL; and (e) 30 µL, and FIG. 5D shows square-wave voltammetry of 100 µM C1 in control experiments with varying volumes of double-distilled water as in FIG. 5C.

Figure 6A:
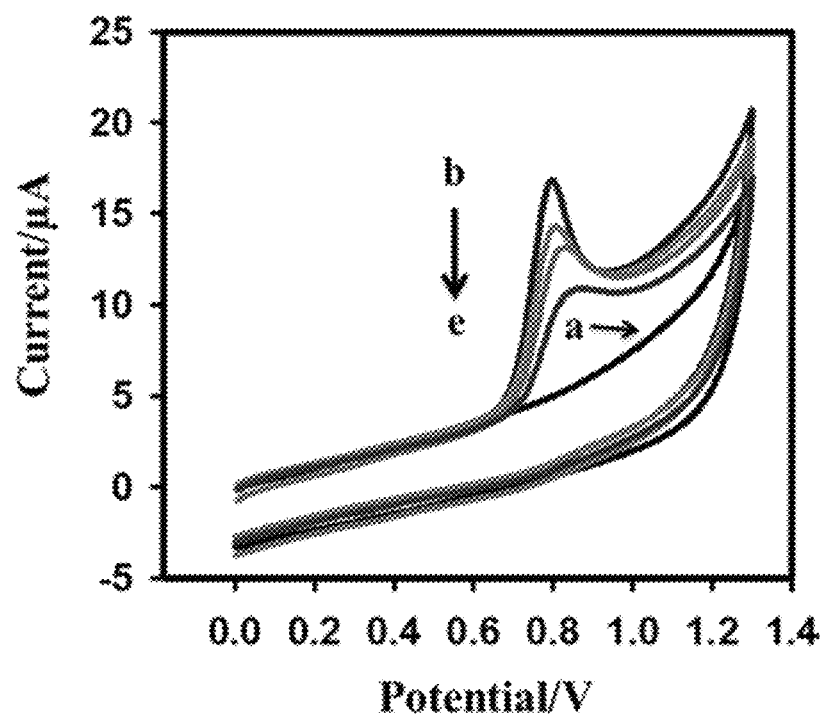
FIGS. 6A-6D are voltammograms for the interaction of C2 with lysozyme in 0.1 M phosphate buffer (pH 6.8) or in control experiments (C2 in double-distilled water)
Figure 6B:
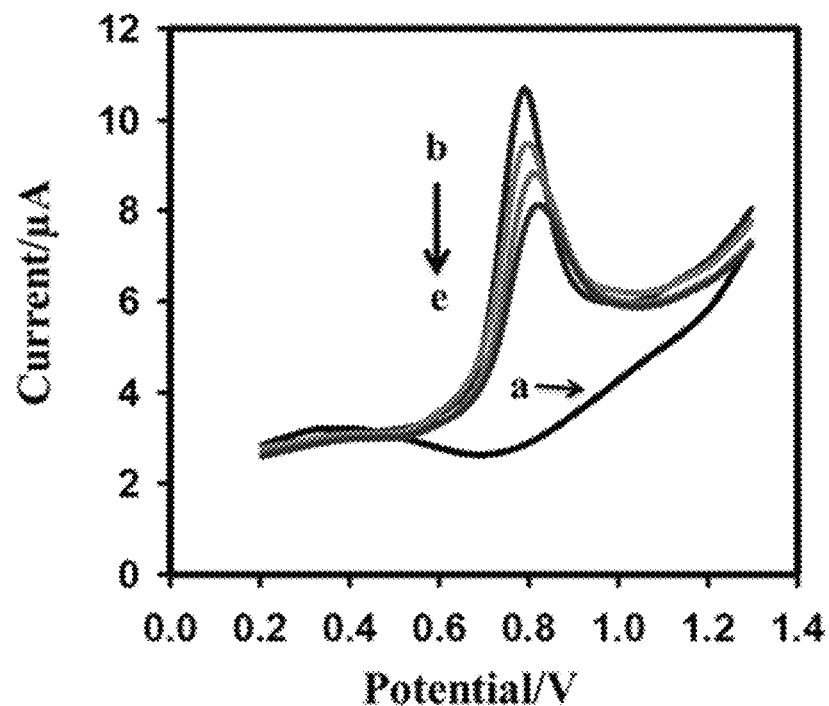
Figure 6C:
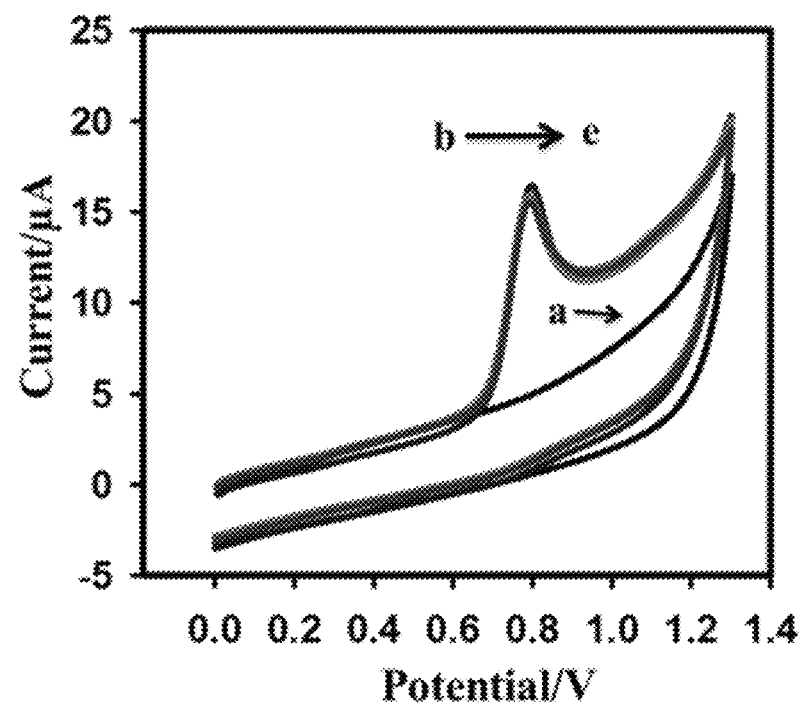
Figure 6D:
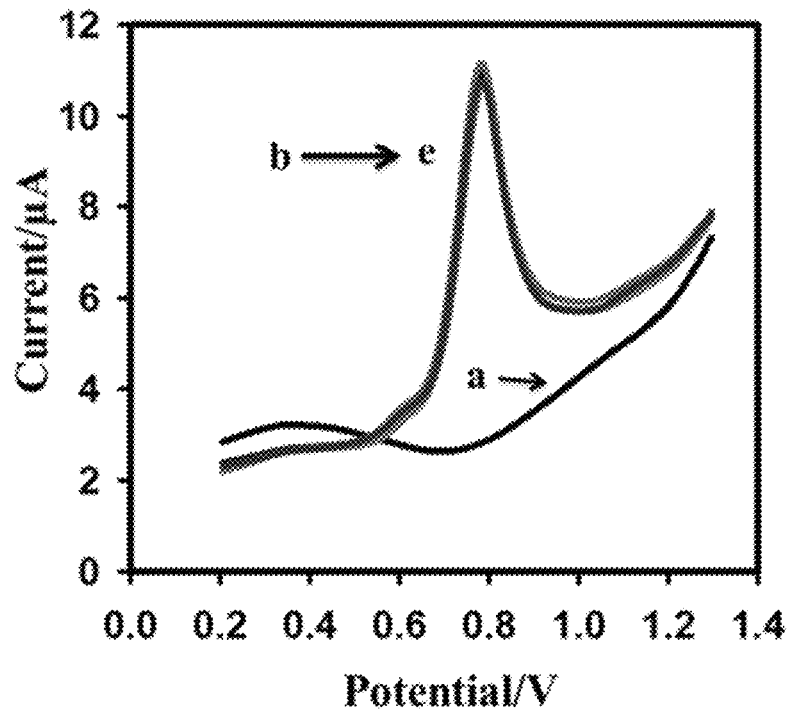

FIG. 6A shows cyclic voltammetry of 100 µM C2 with varying concentrations of lysozyme: (a) buffer blank; (b) C2 alone; (c) C2 and 1 µM lysozyme; (d) C2 and 4 µM lysozyme; and (e) C2 and 10 µM lysozyme, FIG. 6B shows square-wave voltammetry of 100 µM C2 with various concentrations of lysozyme as in FIG. 6A, FIG. 6C shows cyclic voltammetry of 100 µM C2 in control experiments with varying volumes of double-distilled water: (a) buffer blank; (b) 0 µL; (c) 3 µL; (d) 12 µL; and (e) 30 µL, and FIG. 6D shows square-wave voltammetry of 100 µM C2 in control experiments with varying volumes of double-distilled water as in FIG. 6C.

Figure 7A:
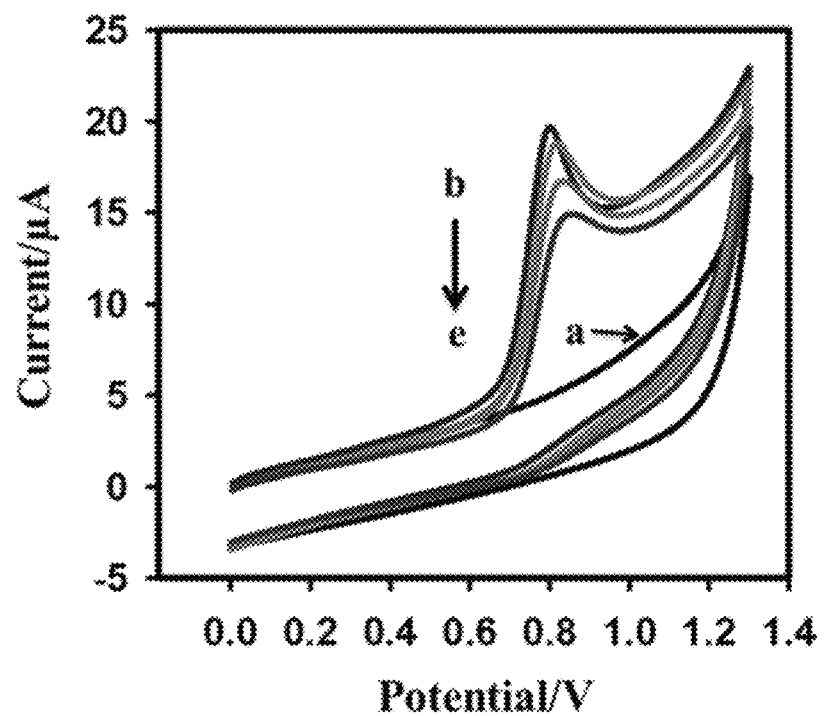
FIGS. 7A-7D are voltammograms for the interaction of C3 with lysozyme in 0.1 M phosphate buffer (pH 6.8) or in control experiments (C3 in double-distilled water)
Figure 7B:
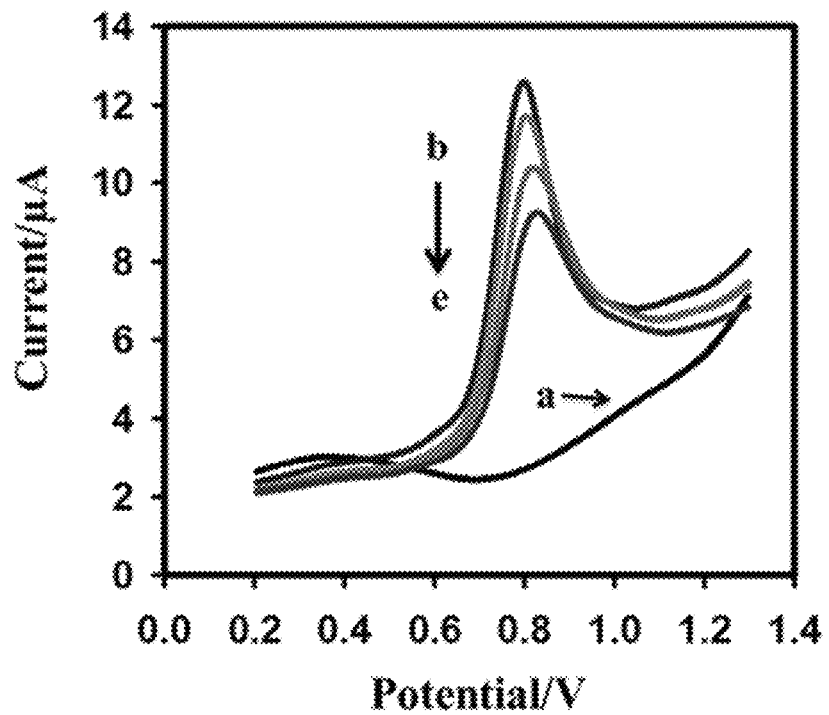
Figure 7C:
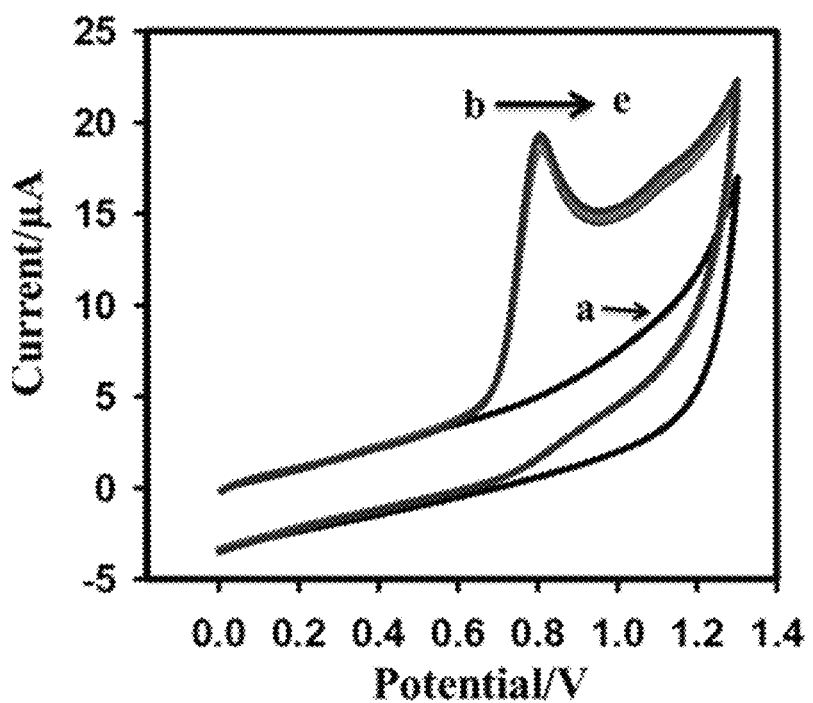
Figure 7D:
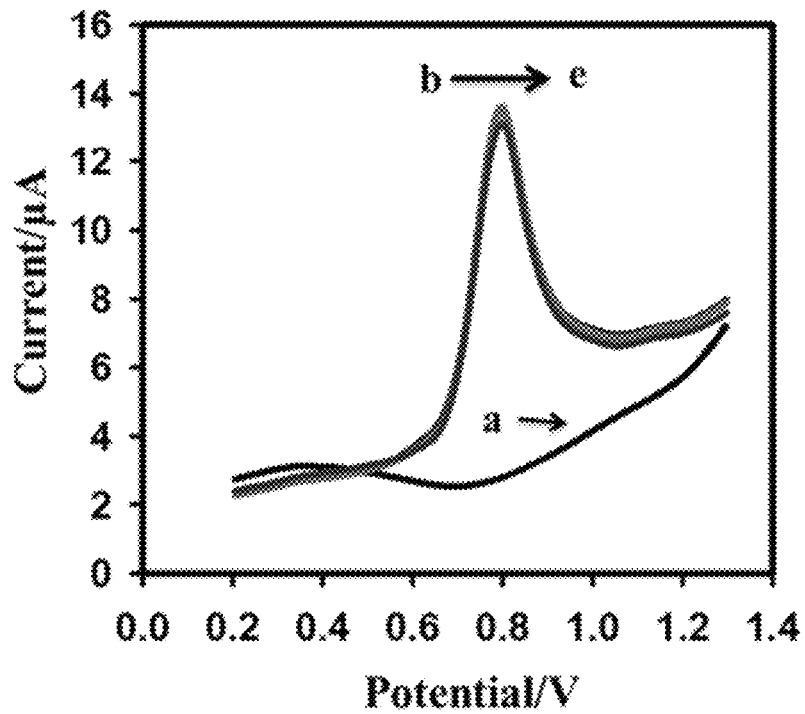

FIG. 7A shows cyclic voltammetry of 100 µM C3 with varying concentrations of lysozyme: (a) buffer blank; (b) C3 alone; (c) C3 and 1 µM lysozyme; (d) C3 and 4 µM lysozyme; and (e) C3 and 10 µM lysozyme, FIG. 7B shows square-wave voltammetry of 100 µM C3 with various concentrations of lysozyme as in FIG. 7A, FIG. 7C shows cyclic voltammetry of 100 µM C3 in control experiments with varying volumes of double-distilled water: (a) buffer blank; (b) 0 µL; (c) 3 µL; (d) 12 µL; and (e) 30 µL, and FIG. 7D shows square-wave voltammetry of 100 µM C3 in control experiments with varying volumes of double-distilled water as in FIG. 7C.

Figure 8A:
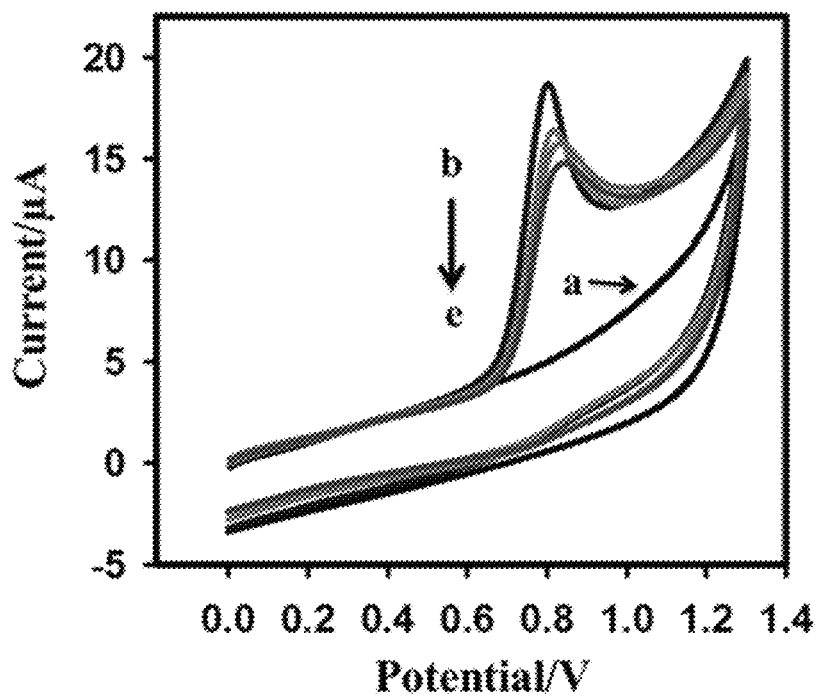
FIGS. 8A-8D are voltammograms for the interaction of complex C4 with lysozyme in 0.1 M phosphate buffer (pH 6.8) or in control experiments (C4 in double-distilled water)
Figure 8B:
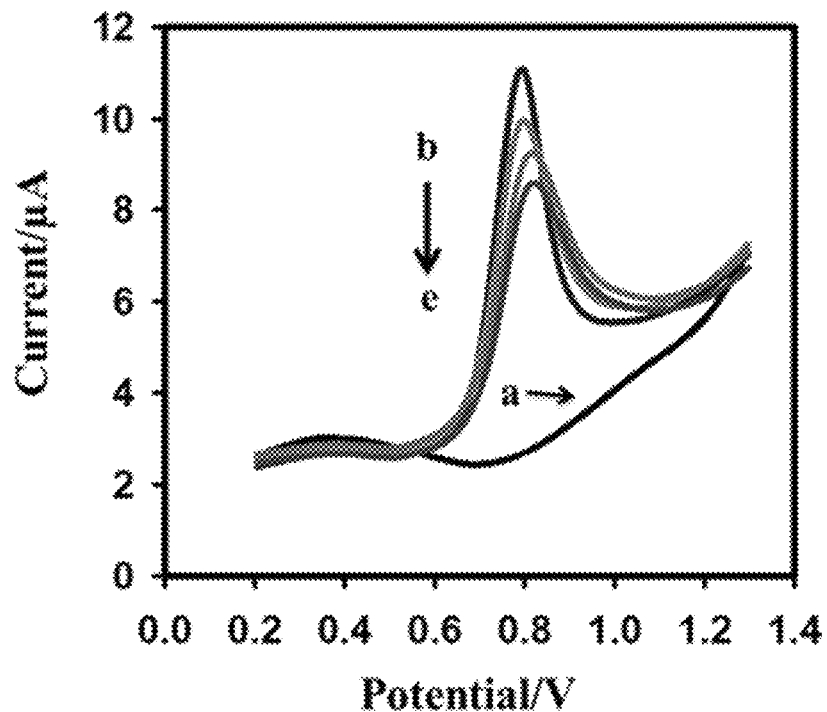
Figure 8C:
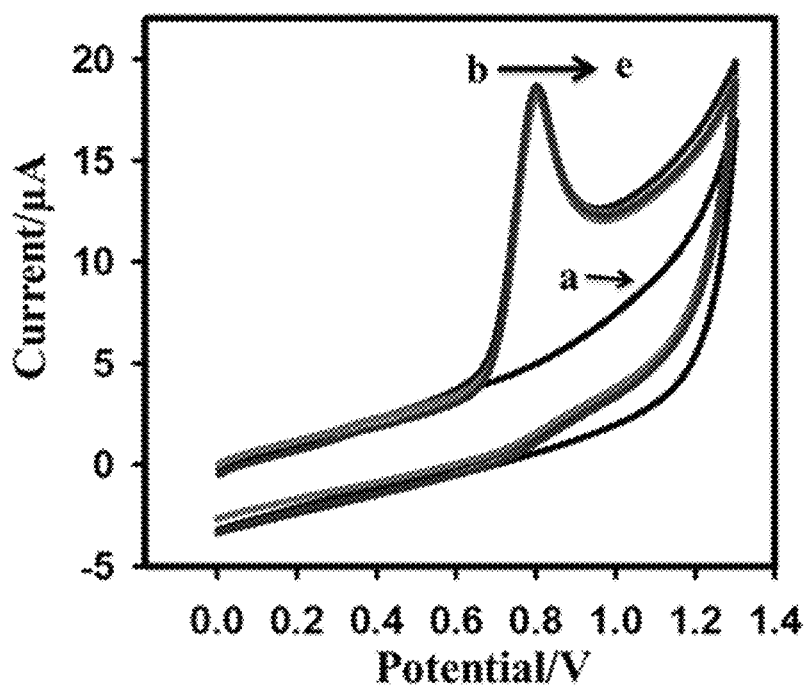
Figure 8D:
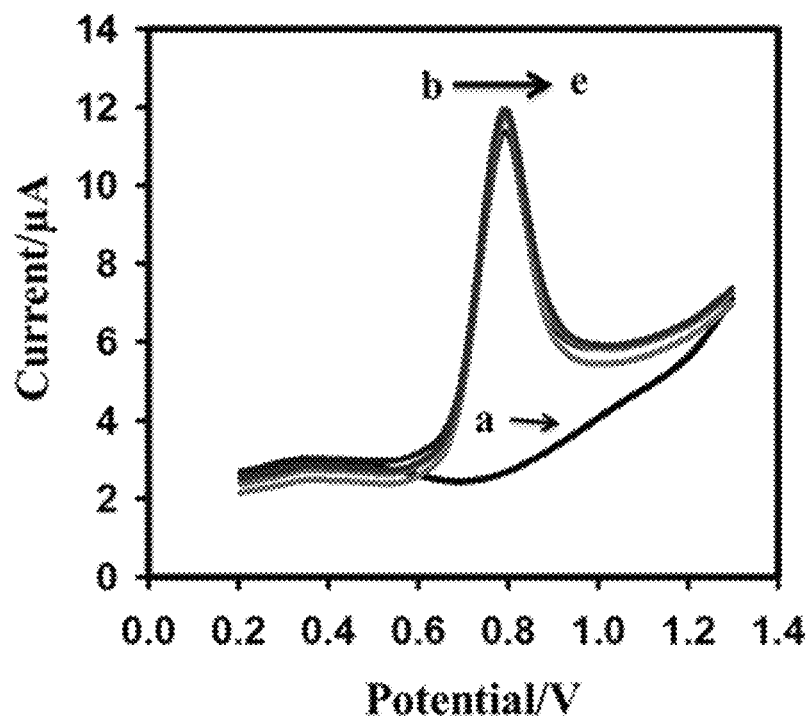

FIG. 8A shows cyclic voltammetry of 100 µM C4 with varying concentrations of lysozyme: (a) buffer blank; (b) C4 alone; (c) C4 and 1 µM lysozyme; (d) C4 and 4 µM lysozyme; and (e) C4 and 10 µM lysozyme, FIG. 8B shows square-wave voltammetry of 100 µM C4 with various concentrations of lysozyme as in FIG. 8A, FIG. 8C shows cyclic voltammetry of 100 µM C4 in control experiments with varying volumes of double-distilled water: (a) buffer blank; (b) 0 µL; (c) 3 µL; (d) 12 µL; and (e) 30 µL and FIG. 8D shows square-wave voltammetry of 100 µM C4 in control experiments with varying volumes of double-distilled water as in FIG. 8C.

Figure 9A:
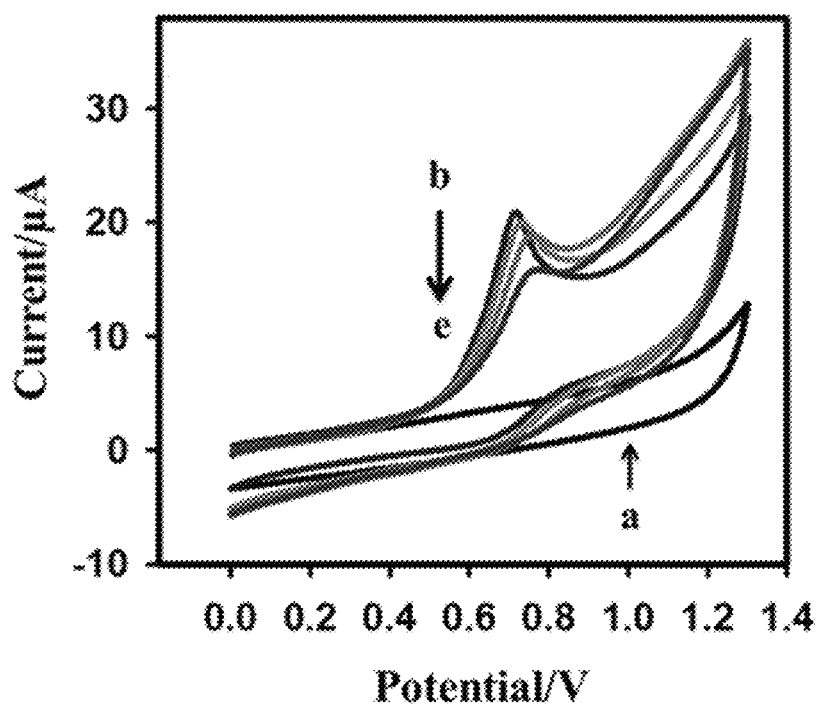
FIGS. 9A-9D are voltammograms for the interaction of complex C5 with 0.5 mM tryptophan in 0.1 M phosphate buffer (pH 6.8) or control experiments (0.5 mM tryptophan alone or C5 alone with varying volumes of ethanol)
Figure 9B:
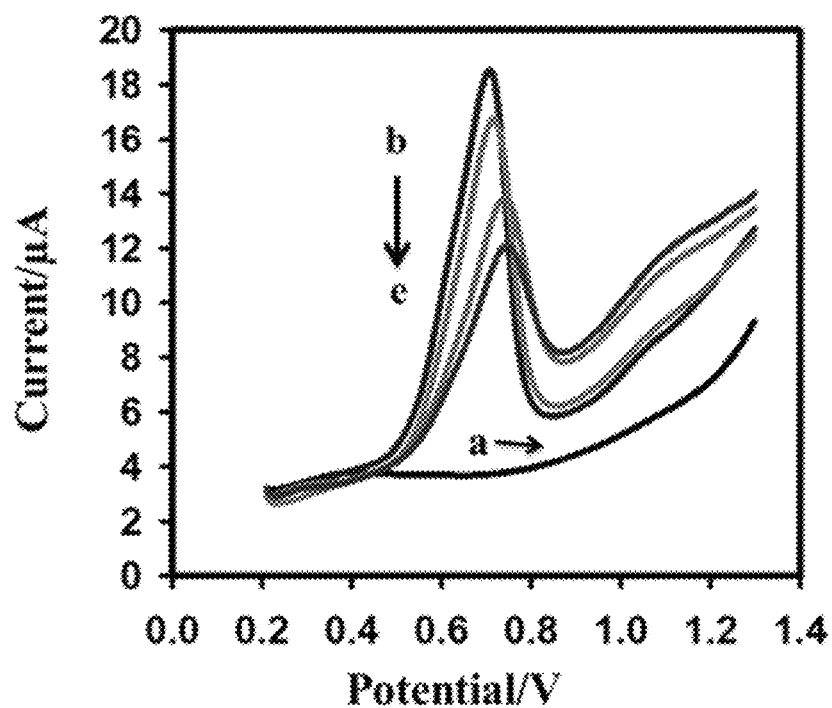
Figure 9C:
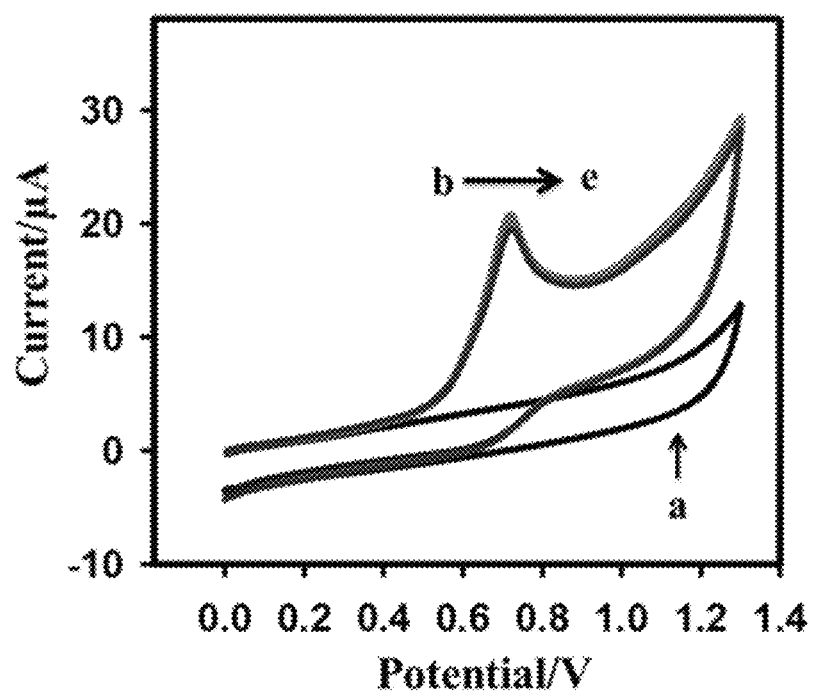
Figure 9D:
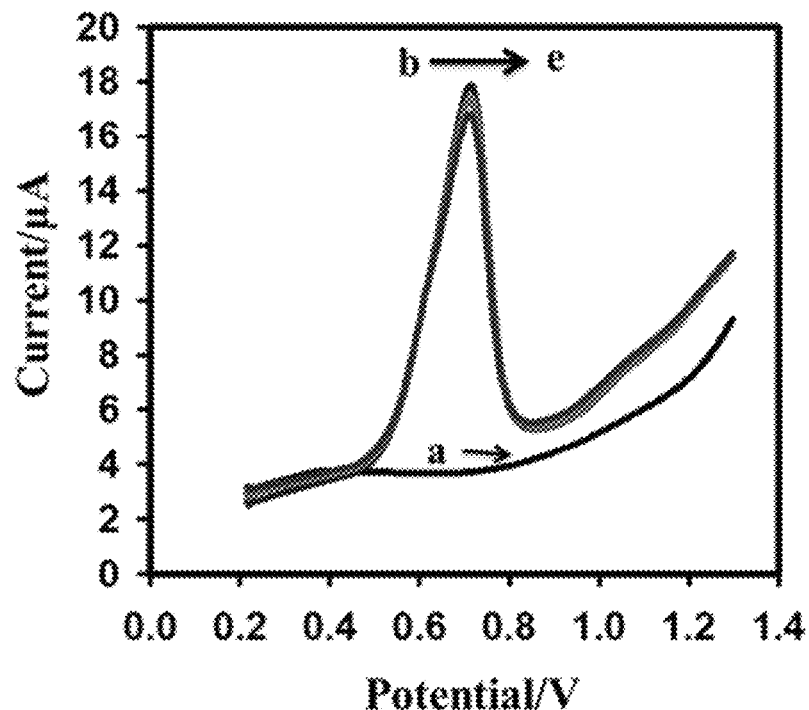

FIG. 9A shows cyclic voltammetry of 0.5 mM tryptophan with varying concentrations of C5: (a) buffer blank; (b) tryptophan alone; (c) tryptophan and 10 µM C5; (d) tryptophan and 40 µM C5; and (e) tryptophan and 100 µM C5, FIG. 9B shows square-wave voltammetry of 0.5 mM tryptophan with varying concentrations of C5 as in FIG. 9A, FIG. 9C shows cyclic voltammetry of 0.5 mM tryptophan in control experiments with varying volumes of ethanol: (a) buffer blank; (b) 0 µL; (c) 15 µL; (d) 60 µL; and (e) 150 µL, and FIG. 9D shows square-wave voltammetry of 100 µM C5 in control experiments with varying volumes of ethanol as in FIG. 9C.

Figure 10A:
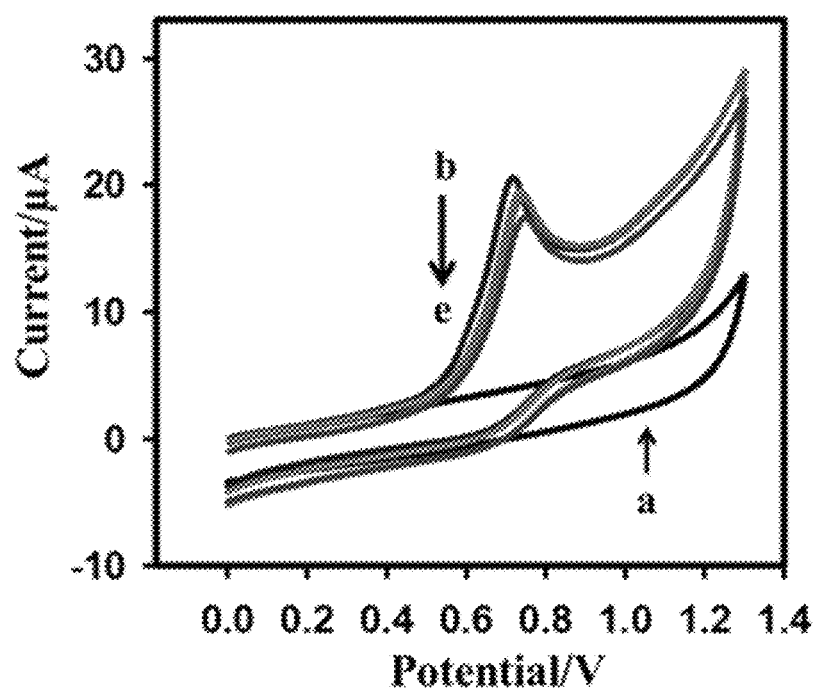
FIGS. 10A-10D are voltammograms for the interaction of complex C6 with 0.5 mM tryptophan in 0.1 M phosphate buffer (pH 6.8) or control experiments (0.5 mM tryptophan alone or C6 alone with varying volumes of ethanol)
Figure 10B:
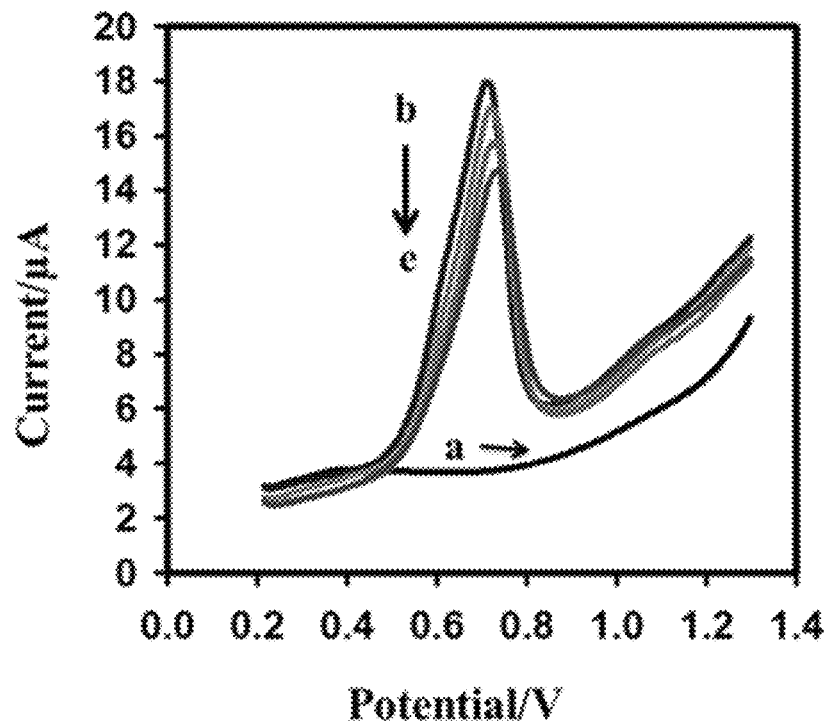
Figure 10C:
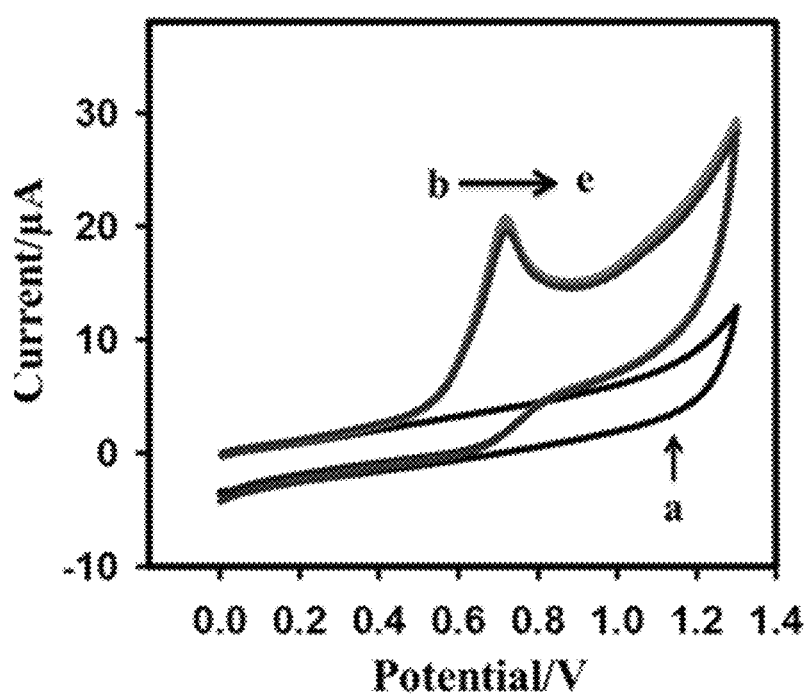
Figure 10D:
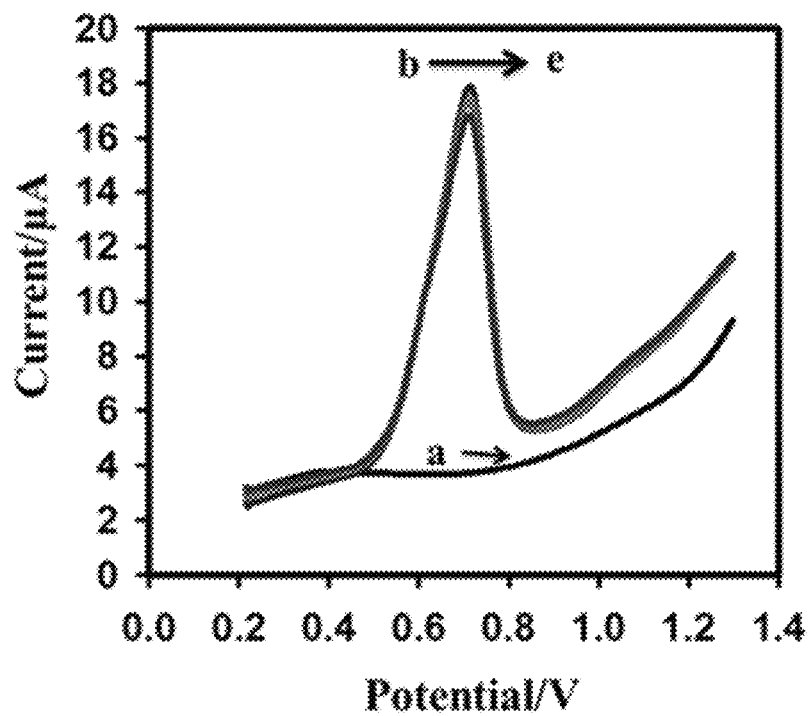

FIG. 10A shows cyclic voltammetry of 0.5 mM tryptophan with varying concentrations of C6: (a) buffer blank; (b) tryptophan alone; (c) tryptophan and 10 µM C6; (d) tryptophan and 40 µM C6; and (e) tryptophan and 100 µM C6. FIG. 10B shows square-wave voltammetry of 0.5 mM tryptophan with varying concentrations of C6 as in FIG. 10A. FIG. 10C shows cyclic voltammetry of 0.5 mM tryptophan in control experiments with varying volumes of ethanol: (a) buffer blank; (b) 0 µL; (c) 15 µL; (d) 60 µL; and (e) 150 µL, and FIG. 10D shows square-wave voltammetry of 100 µM C6 in control experiments with varying volumes of ethanol as in FIG. 10C.

Figure 11A:
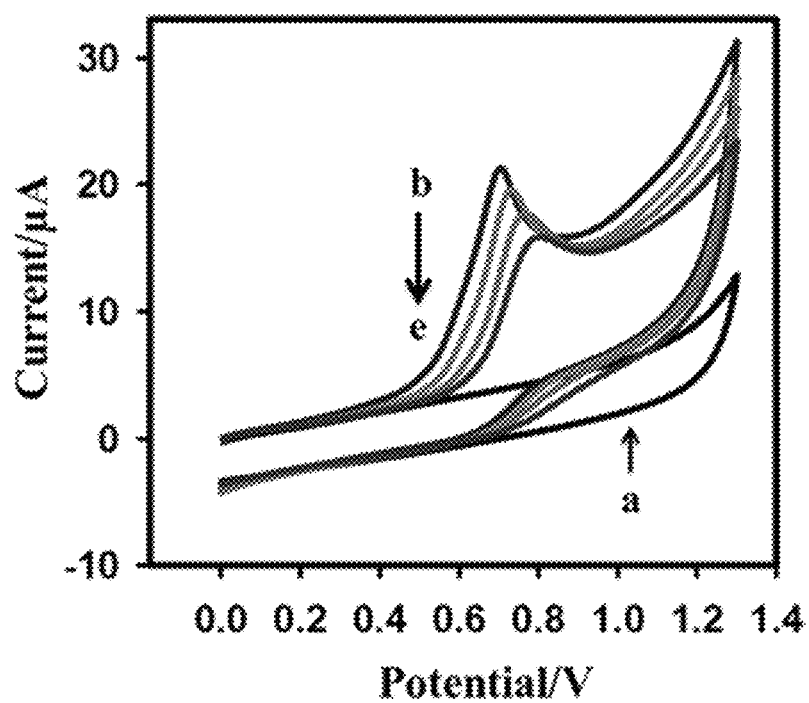
FIGS. 11A-11D are voltammograms for the interaction of complex C7 with 0.5 mM tryptophan in 0.1 M phosphate buffer (pH 6.8) or control experiments (0.5 mM tryptophan alone or C7 alone with varying volumes of ethanol)
Figure 11B:
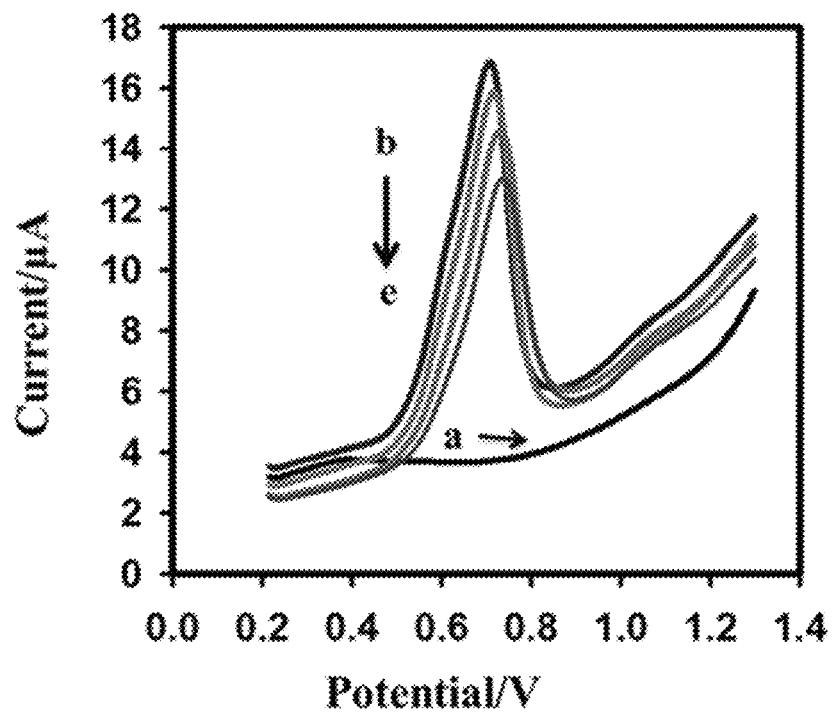
Figure 11C:
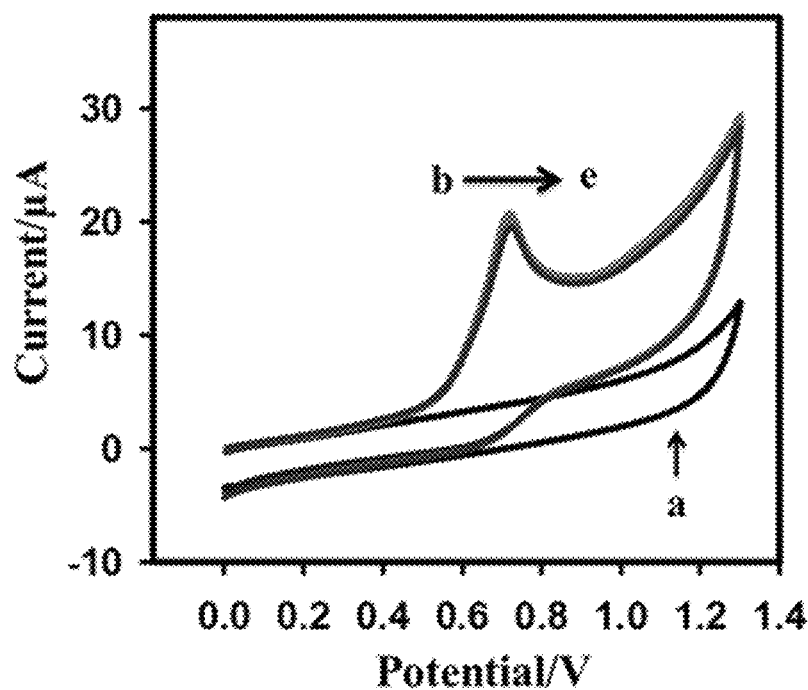
Figure 11D:
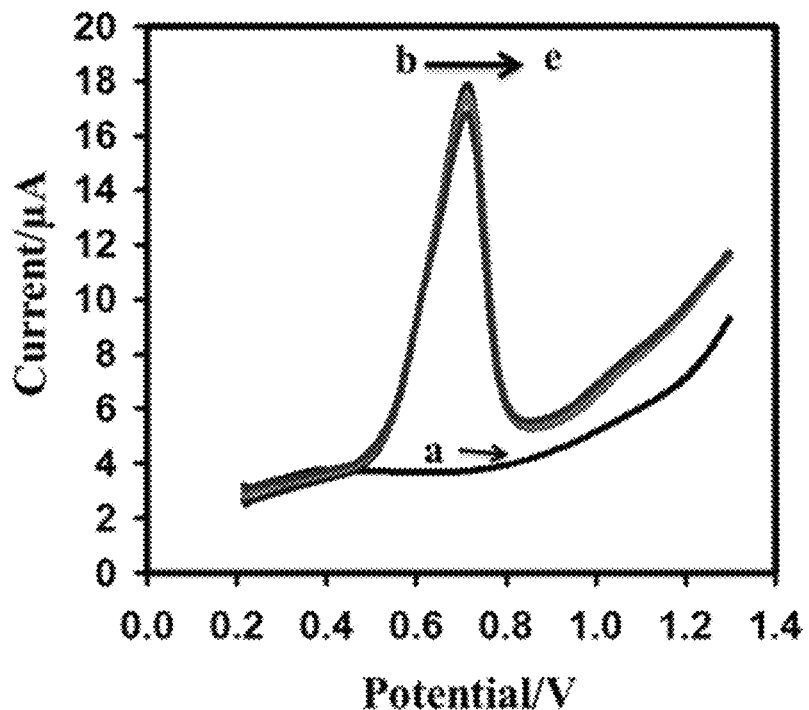

FIG. 11A shows cyclic voltammetry of 0.5 mM tryptophan with varying concentrations of C7: (a) buffer blank; (b) tryptophan alone; (c) tryptophan and 10 µM C7; (d) tryptophan and 40 µM C7; and (e) tryptophan and 100 µM C7, FIG. 11B shows square-wave voltammetry of 0.5 mM tryptophan with varying concentrations of C7 as in FIG. 11A, FIG. 11C shows cyclic voltammetry of 0.5 mM tryptophan in control experiments with varying volumes of ethanol: (a) buffer blank; (b) 0 µL; (c) 15 µL; (d) 60 µL; and (e) 150 µL and FIG. 11D shows square-wave voltammetry of 100 µM C7 in control experiments with varying volumes of ethanol as in FIG. 11C.

Figure 12A:
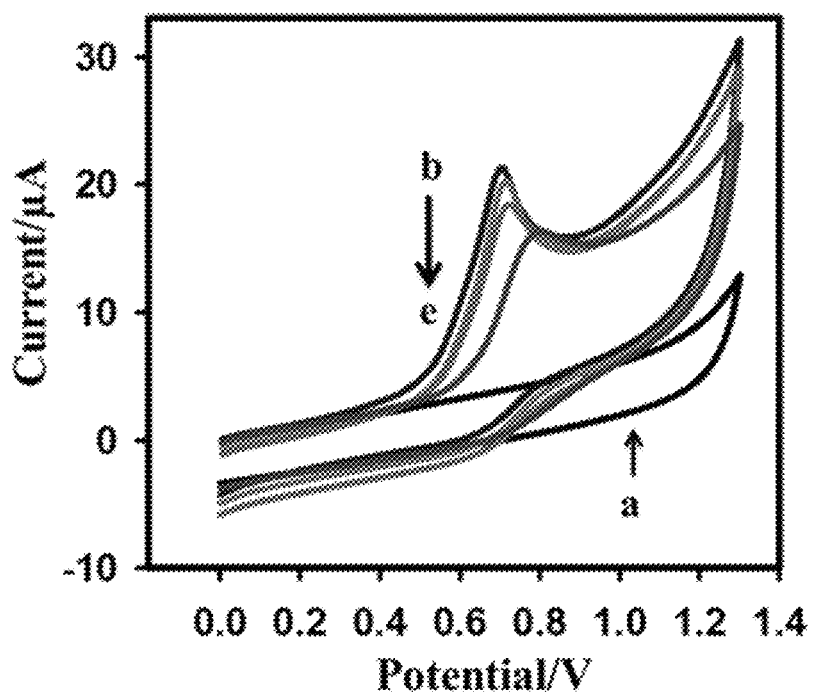
FIGS. 12A-12D are voltammograms for the interaction of complex C8 with 0.5 mM tryptophan in 0.1 M phosphate buffer (pH 6.8) or control experiments (0.5 mM tryptophan alone or C8 alone with varying volumes of ethanol)
Figure 12B:
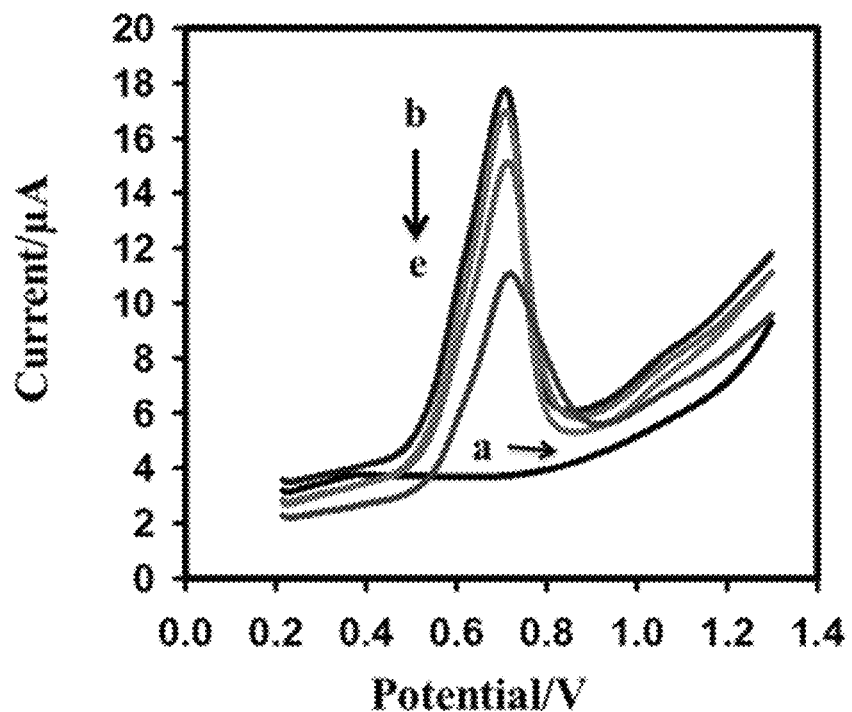
Figure 12C:
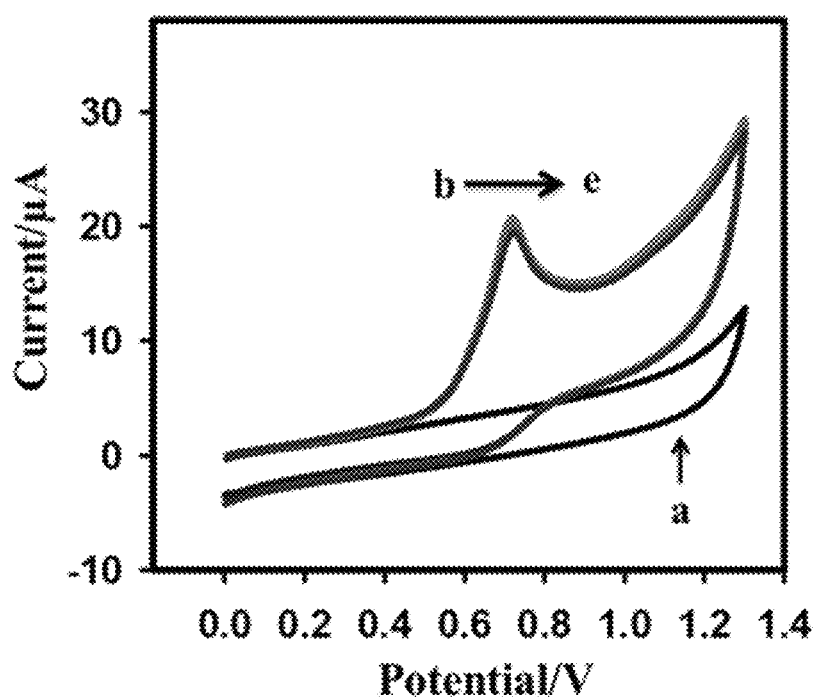
Figure 12D:
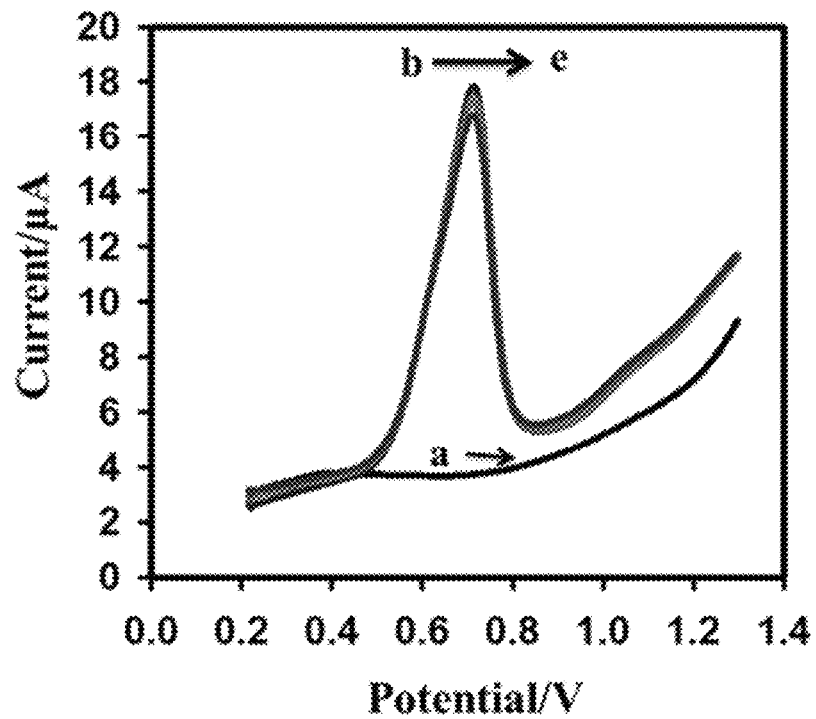

FIG. 12A shows cyclic voltammetry of 0.5 mM tryptophan with varying concentrations of C8: (a) buffer blank; (b) tryptophan alone; (c) tryptophan and 10 µM C8; (d) tryptophan and 40 µM C8; and (e) tryptophan and 100 µM C8, FIG. 12B shows square-wave voltammetry of 0.5 mM tryptophan with varying concentrations of C8 as in FIG. 12A, FIG. 12C shows cyclic voltammetry of 0.5 mM tryptophan in control experiments with varying volumes of ethanol: (a) buffer blank; (b) 0 µL; (c) 15 µL; (d) 60 µL; and (e) 150 µL, and FIG. 12D shows square-wave voltammetry of 100 µM C5 in control experiments with varying volumes of ethanol as in FIG. 12C.

Figure 13A:
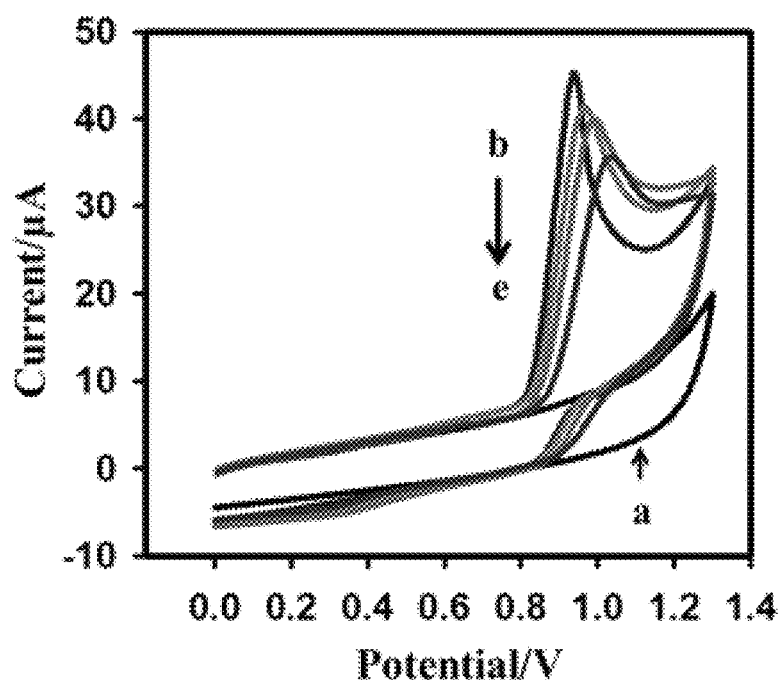
FIGS. 13A-13F are voltammograms for the interaction of complex C1 with 0.5 mM guanine in 0.1 M phosphate buffer (pH 6.8) or control experiments (0.5 mM guanine alone with varying volumes of ethanol or C1 alone)
Figure 13B:
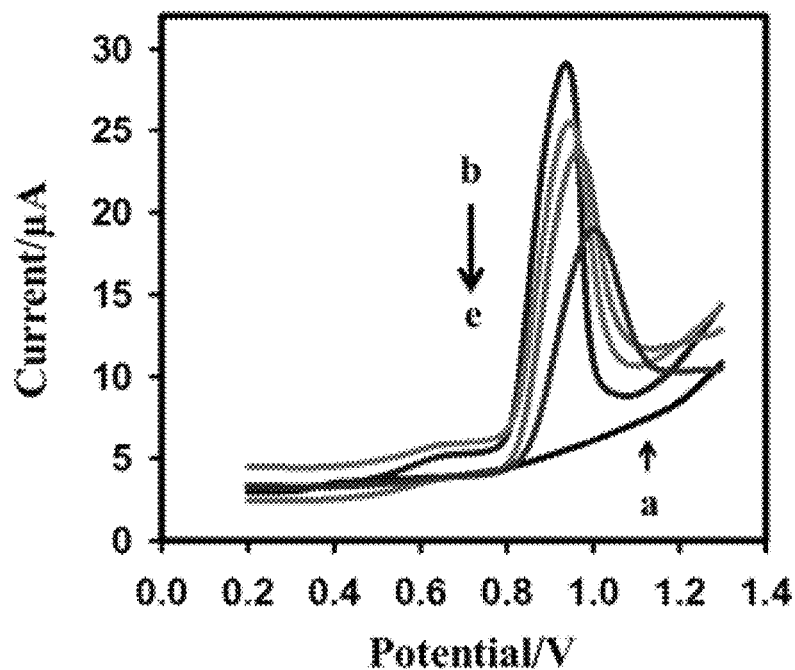
Figure 13C:
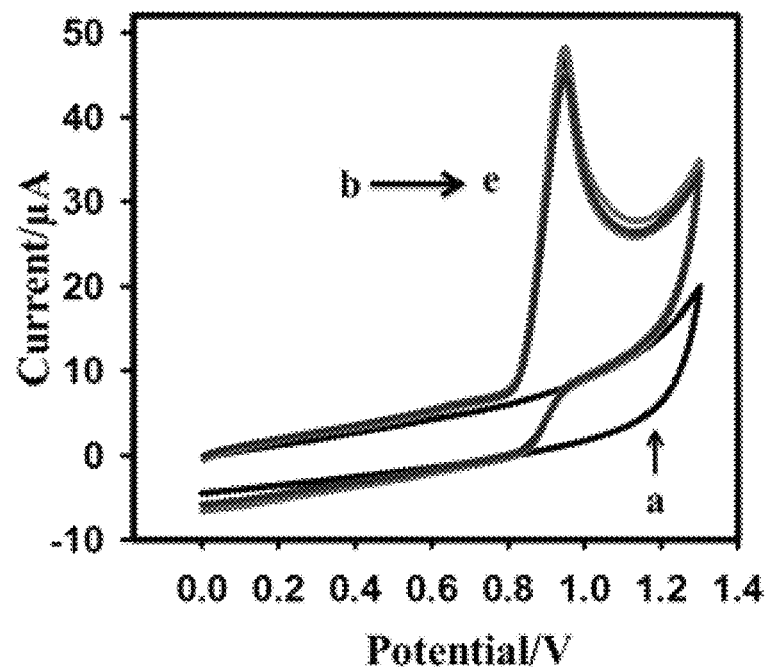
Figure 13D:
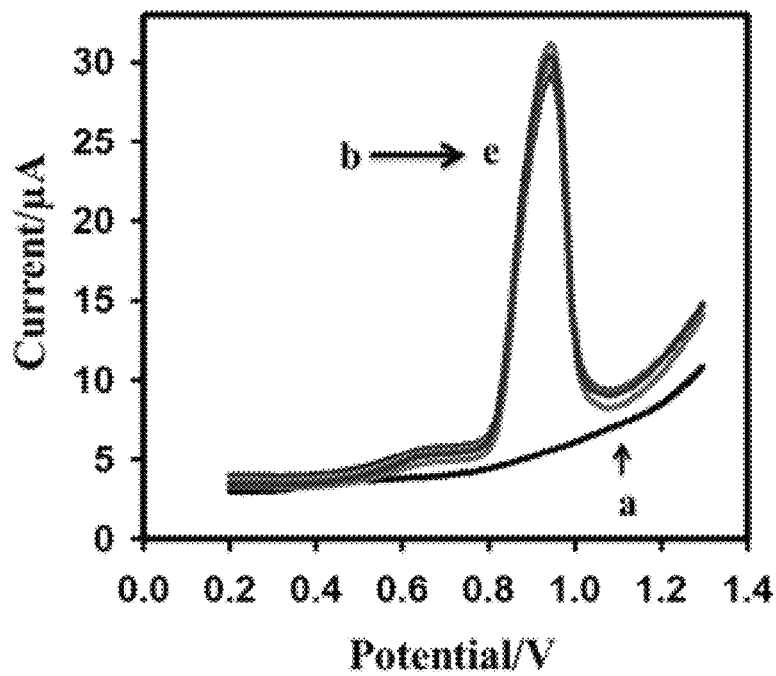
Figure 13E:
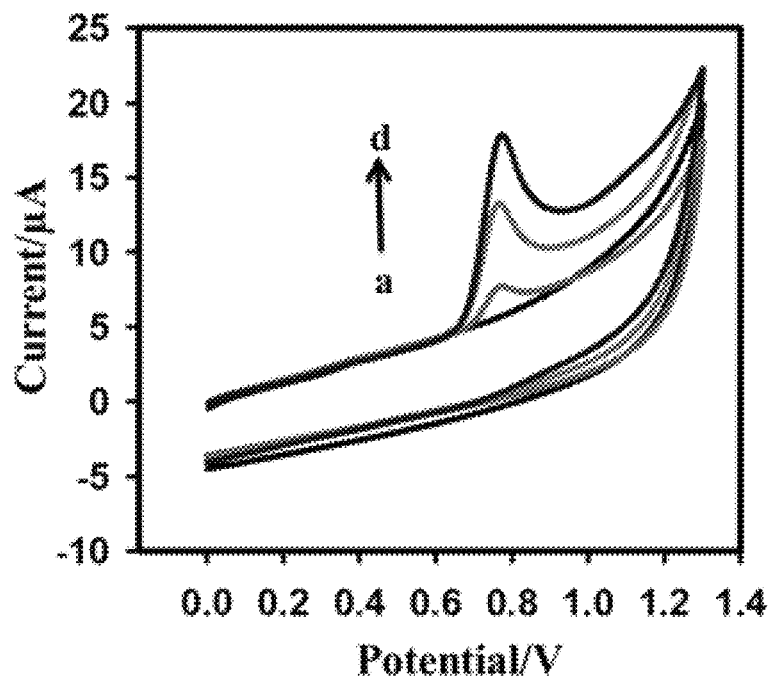
Figure 13F:
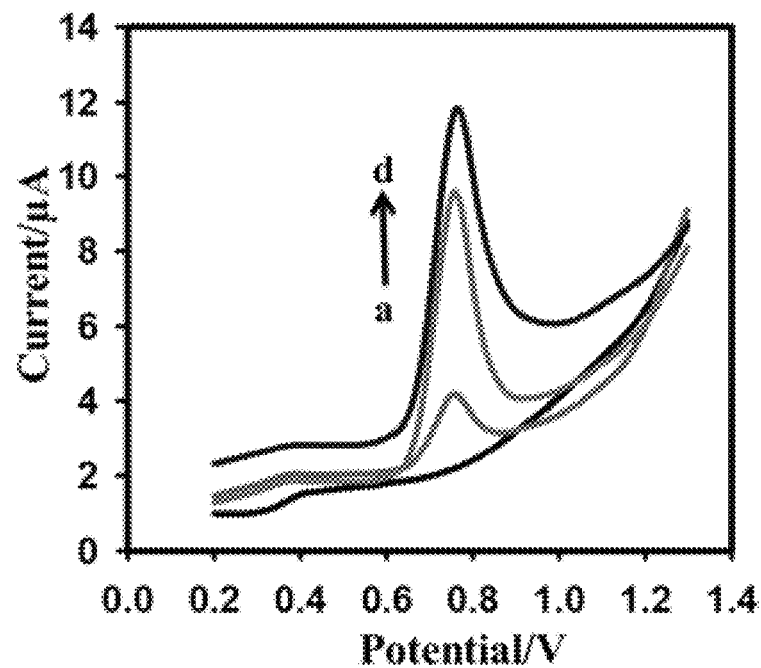

FIG. 13A shows cyclic voltammetry of 0.5 mM guanine with varying concentrations of C1: (a) buffer blank; (b) guanine alone; (c) guanine and 10 µM C1; (d) guanine and 40 µM C1; and (e) guanine and 100 µM C1, FIG. 13B shows square-wave voltammetry of 0.5 mM guanine with varying concentrations of C1 as in FIG. 13A, FIG. 13C shows cyclic voltammetry of 0.5 mM guanine in control experiments with varying volumes of ethanol: (a) buffer blank; (b) 0 µL; (c) 15 µL; (d) 60 µL; and (e) 150 µL, FIG. 13D shows square-wave voltammetry of 0.5 mM guanine in control experiments with varying volumes of ethanol: (a) buffer blank; (b) 0 µL; (c) 15 µL; (d) 60 µL; and (e) 150 µL, FIG. 13E shows cyclic voltammetry of C1 alone at: (a) 0 µM; (b) 10 µM; (c) 40 µM;

and (d) 100 µM, and FIG. 13F shows square-wave voltammetry of C1 alone at: (a) 0 µM; (b) 10 µM; (c) 40 µM; and (d) 100 µM.

Figure 14A:
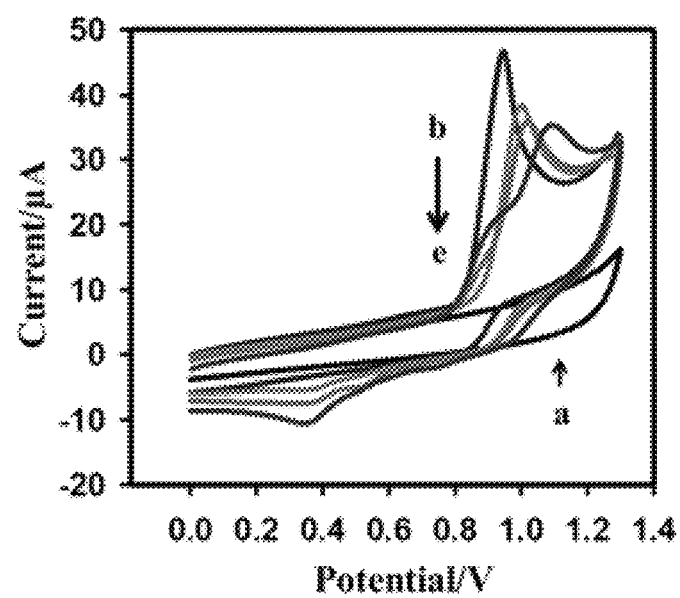
FIGS. 14A-14F are voltammograms for the interaction of complex C5 with 0.5 mM guanine in 0.1 M phosphate buffer (pH 6.8) or control experiments (0.5 mM guanine alone with varying volumes of ethanol or C5 alone)
Figure 14B:
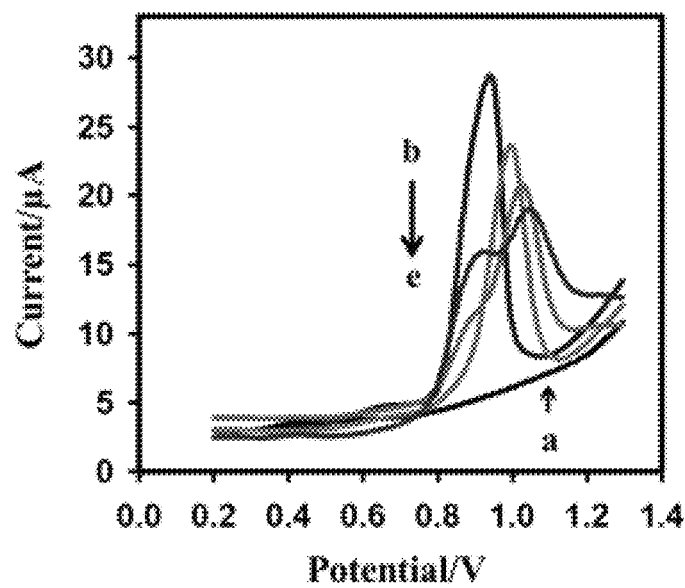
Figure 14C:
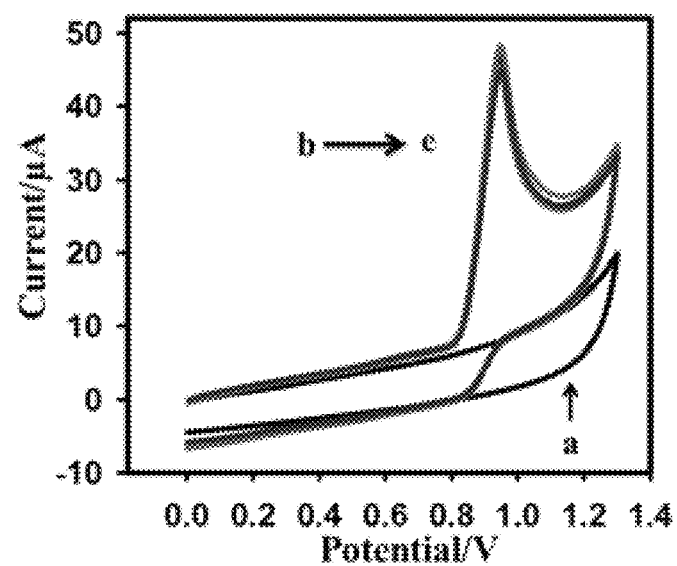
Figure 14D:
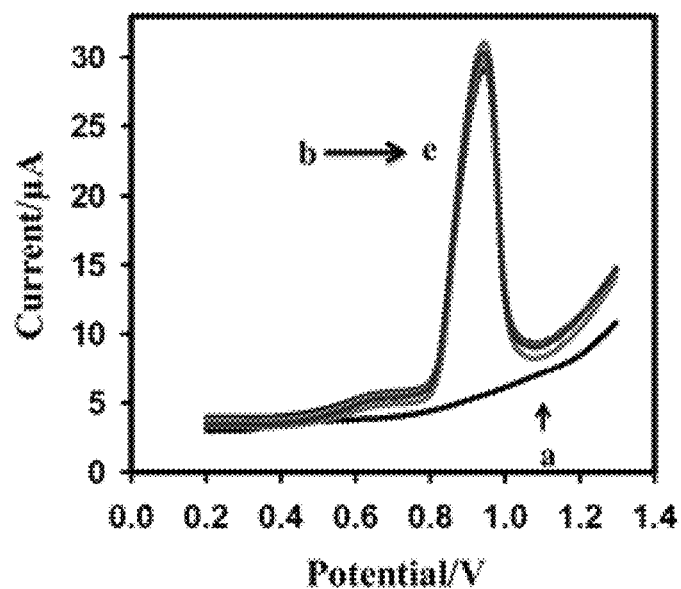
Figure 14E:
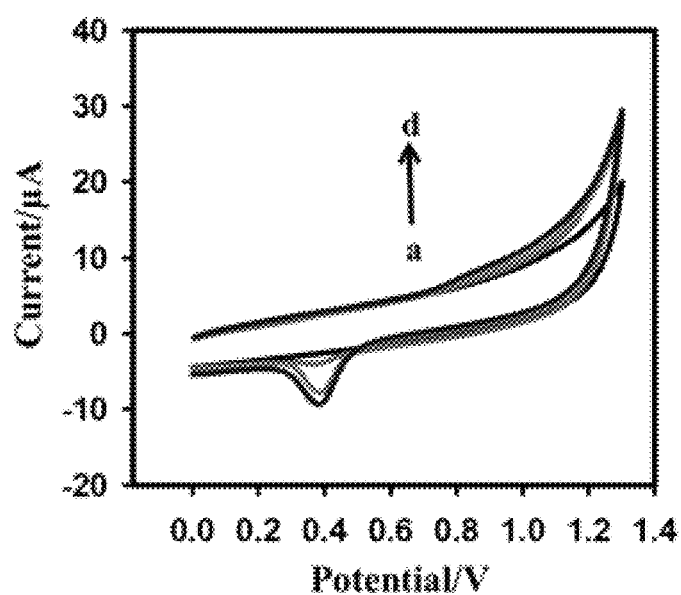
Figure 14F:
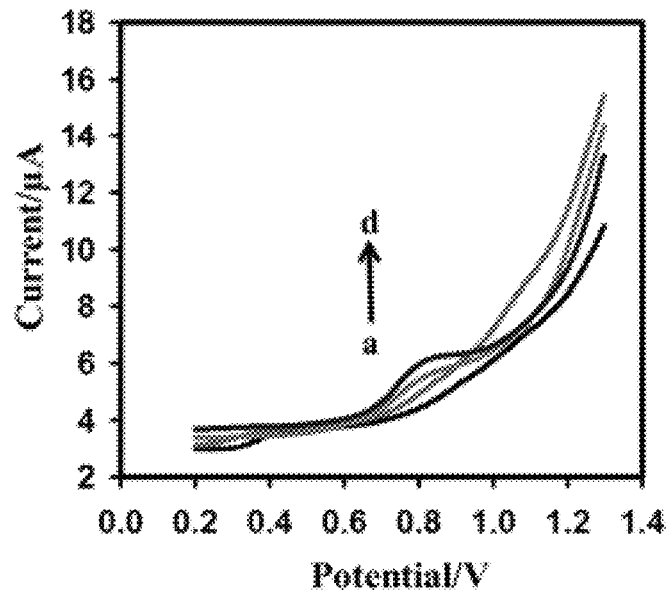

FIG. 14A shows cyclic voltammetry of 0.5 mM guanine with varying concentrations of C5: (a) buffer blank; (b) guanine alone; (c) guanine and 10 µM C5; (d) guanine and 40 µM C5; and (e) guanine and 100 µM C5, FIG. 14B shows square-wave voltammetry of 0.5 mM guanine with varying concentrations of C5 as in FIG. 14A, FIG. 14C shows cyclic voltammetry of 0.5 mM guanine in control experiments with varying volumes of ethanol: (a) buffer blank; (b) 0 µL; (c) 15 µL; (d) 60 µL; and (e) 150 µL, FIG. 14D Square-wave voltammetry of 0.5 mM guanine in control experiments with varying volumes of ethanol: (a) buffer blank; (b) 0 µL; (c) 15 µL; (d) 60 µL; and (e) 150 µL, FIG. 14E shows cyclic voltammetry of C5 alone at: (a) 0 µM; (b) 10 µM; (c) 40 µM; and (d) 100 µM, and FIG. 14F shows square-wave voltammetry of C5 alone at: (a) 0 µM; (b) 10 µM; (c) 40 µM; and (d) 100 µM.

TABLE 4

Voltammetry peak potential (mV) of 100 µM complexes (C1-C4) with 1-10 µM lysozyme

| Compound | Technique | Lysozyme | | | |
|---|---|---|---|---|---|
| | | 0 µM | 1 µM | 4 µM | 10 µM |
| C1 | CV | 0.73898 | 0.81421 | 0.83191 | 0.87616 |
| C1 | SWV | 0.79338 | 0.80345 | 0.8387 | 0.86388 |
| C2 | CV | 0.79208 | 0.80093 | 0.81863 | 0.83191 |
| C2 | SWV | 0.78835 | 0.79338 | 0.80849 | 0.81352 |
| C3 | CV | 0.79651 | 0.80978 | 0.82306 | 0.83633 |
| C3 | SWV | 0.79338 | 0.80345 | 0.81352 | 0.82359 |
| C4 | CV | 0.79651 | 0.80978 | 0.81863 | 0.82748 |
| C4 | SWV | 0.78835 | 0.79338 | 0.80849 | 0.81352 |

CV, cyclic voltammetry;
SWV, square-wave voltammetry

TABLE 5

Voltammetry peak potential (mV) of 0.5 mM tryptophan with 10-100 uM complexes (C5-C8)

| Compound | Technique | Compound | | | |
|---|---|---|---|---|---|
| | | 0 µM | 10 µM | 40 µM | 100 µM |
| C5 | CV | 0.71243 | 0.72571 | 0.74341 | 0.74783 |
| C5 | SWV | 0.70862 | 0.71365 | 0.73883 | 0.7489 |
| C6 | CV | 0.71243 | 0.73013 | 0.73898 | 0.74341 |
| C6 | SWV | 0.70862 | 0.71869 | 0.72372 | 0.72876 |
| C7 | CV | 0.71243 | 0.72571 | 0.75668 | 0.78323 |
| C7 | SWV | 0.70862 | 0.71365 | 0.72876 | 0.7338 |
| C8 | CV | 0.71243 | 0.71686 | 0.72128 | 0.78323 |
| C8 | SWV | 0.70862 | 0.70862 | 0.71365 | 0.71869 |

CV, cyclic voltammetry;
SWV, square-wave voltammetry

TABLE 6

Voltammetry peak potential (mV) of 0.5 mM guanine with 10-100 µM complexes C1 and C5

| Compound | Technique | Compound | | | |
|---|---|---|---|---|---|
| | | 0 µM | 10 µM | 40 µM | 100 µM |
| C1 | CV | 0.93811 | 0.96024 | 0.98236 | 1.0222 |
| C1 | SWV | 0.93437 | 0.94444 | 0.95955 | 0.9948 |
| C5 | CV | 0.93811 | 0.99564 | 1.0133 | 1.0753 |
| C5 | SWV | 0.93437 | 0.9948 | 1.025 | 1.0502 |

CV, cyclic voltammetry;
SWV, square-wave voltammetry

The invention claimed is:

1. A solid pharmaceutical composition in the form of a tablet, comprising:
   a gold (III) complex of formula (I),

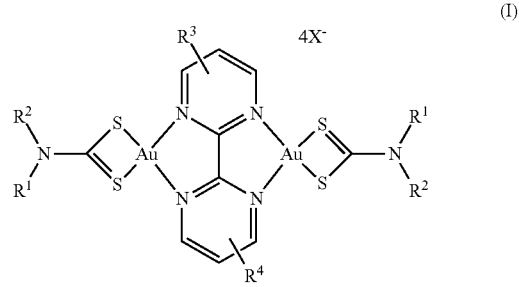

and/or a pharmaceutically acceptable salt thereof, and
   a pharmaceutically acceptable carrier selected from the group consisting of talc magnesium, calcium stearate, zinc stearate, steric acid, lactose, corn starch, sodium carboxymethyl cellulose, ethyl cellulose, and cellulose acetate;
   wherein:
   $R^1$ and $R^2$ are each independently a hydrogen or an optionally substituted arylalkyl;
   $R^3$ and $R^4$ are each independently a hydrogen, an optionally substituted alkoxy, or a hydroxyl; and
   X is Cl or Br.

2. The solid pharmaceutical composition of claim 1, wherein the gold (III) complex of formula (I) $R^1$ and $R^2$ are each independently a $C_7$ to $C_{12}$ arylalkyl.

3. The solid pharmaceutical composition of claim 1, wherein the gold (III) complex of formula (I) $R^1$ and $R^2$ are each benzyl.

4. The solid pharmaceutical composition of claim 1, wherein the gold (III) complex of formula (I) $R^3$ and $R^4$ are each hydrogen.

5. The solid pharmaceutical composition of claim 1, wherein the gold (III) complex of formula (I) X is Cl.

* * * * *